(12) United States Patent
Sun et al.

(10) Patent No.: US 7,919,487 B2
(45) Date of Patent: Apr. 5, 2011

(54) HETEROARYL COMPOUNDS

(75) Inventors: Lijun Sun, Harvard, MA (US); Shijie Zhang, Nashua, NH (US); Keizo Koya, Chestnut Hill, MA (US); Dinesh Chimmanamada, Waltham, MA (US); Hao Li, Brookline, MA (US); David James, Cambridge, MA (US); Elena Kostik, Arlington, MA (US)

(73) Assignee: Synta Pharmaceuticals Corporation, Lexington, MA (US)

( * ) Notice: Subject to any disclaimer, the term of this patent is extended or adjusted under 35 U.S.C. 154(b) by 739 days.

(21) Appl. No.: 11/271,704

(22) Filed: Nov. 10, 2005

(65) Prior Publication Data

US 2006/0122156 A1 Jun. 8, 2006

Related U.S. Application Data

(60) Provisional application No. 60/627,001, filed on Nov. 10, 2004.

(51) Int. Cl.
*A61K 31/397* (2006.01)
*A61K 31/5377* (2006.01)
*A61K 31/50* (2006.01)
*A61K 31/53* (2006.01)
*A61K 31/505* (2006.01)
*C07D 413/14* (2006.01)
*C07D 251/02* (2006.01)
*C07D 401/14* (2006.01)

(52) U.S. Cl. ............ 514/210.01; 514/231.5; 514/241; 514/252.01; 514/256; 544/113; 544/114; 544/122; 544/124; 544/125; 544/129; 544/137; 544/180; 544/238; 544/242; 546/255; 546/268.1

(58) Field of Classification Search .......... 546/255, 546/268.1; 544/113, 114, 122, 124, 129, 544/137, 180, 238, 242; 514/210.01, 231.5, 514/241, 252.01, 256

See application file for complete search history.

(56) References Cited

U.S. PATENT DOCUMENTS

| | | | |
|---|---|---|---|
| 6,174,901 B1 * | 1/2001 | Mantlo et al. | 514/333 |
| 6,362,195 B1 * | 3/2002 | Lowe, III | 514/307 |
| 6,384,032 B1 | 5/2002 | Ono et al. | |
| 6,660,733 B2 | 12/2003 | Sun et al. | |
| 6,858,606 B2 | 2/2005 | Sun et al. | |
| 6,958,332 B2 | 10/2005 | Sun et al. | |
| 7,045,517 B2 | 5/2006 | Ono et al. | |
| 7,067,514 B2 | 6/2006 | Ono et al. | |
| 7,122,665 B2 | 10/2006 | Sun et al. | |
| 7,338,951 B2 | 3/2008 | Ono et al. | |
| 2005/0250770 A1 | 11/2005 | Ono et al. | |
| 2005/0250787 A1 | 11/2005 | Sun et al. | |
| 2005/0282809 A1 | 12/2005 | Ono et al. | |
| 2006/0025409 A1 | 2/2006 | Ono et al. | |
| 2006/0030560 A1 | 2/2006 | Sun et al. | |
| 2006/0063739 A1 | 3/2006 | Sun et al. | |
| 2006/0122209 A1 | 6/2006 | Zhang et al. | |
| 2006/0223996 A1 | 10/2006 | Sun et al. | |
| 2007/0027151 A1 | 2/2007 | Sun et al. | |

FOREIGN PATENT DOCUMENTS

| | | | |
|---|---|---|---|
| WO | WO-00/62778 | 10/2000 | |
| WO | WO-00/78757 | 12/2000 | |
| WO | WO 02/14311 | * 2/2002 | ..... 546/200 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10) (2004) 2394-2404.*
Morissette et al. Advanced Drug Delivery Reviews 2004, 56, 275-300.*
Vippagunta, Sudha R. "Crystalline Solids." Advanced Drug Delivery Reviews 48(2001): 3-26.*
International Search Report and Written Opinion for PCT/US05/40706.
Nishigaki et al. "Synthesis of Iminodipyrimidines", Tetrahedron Letters. 7:539-542 (1969).

* cited by examiner

*Primary Examiner* — Rebecca L Anderson
*Assistant Examiner* — Samantha L Shterengarts
(74) *Attorney, Agent, or Firm* — Edwards Angell Palmer & Dodge LLP; Jeffrey D. Hsi; Mark D. Russett

(57) ABSTRACT

This invention relates to compounds of formula (I):

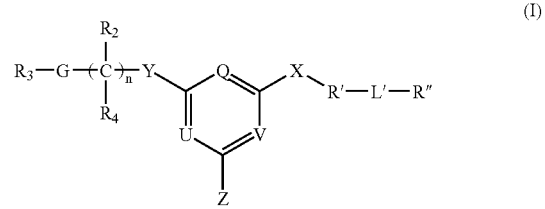

their compositions and methods of use thereof. The compounds (and compositions) are useful in modulating IL-12 production and processes mediated by IL-12.

15 Claims, No Drawings

HETEROARYL COMPOUNDS

RELATED APPLICATION

This application claims the benefit of U.S. provisional patent application Ser. No. 60/627,001, filed Nov. 10, 2004, the disclosure of which is incorporated herein in its entirety by this reference.

BACKGROUND

Interleukin-12 (IL-12) is a heterodimeric cytokine (p70) which plays key roles in immune responses by bridging innate resistance and antigen-specific adaptive immunity. Trinchieri (1993) *Immunol Today* 14: 335. For example, it promotes type 1 T helper cell ($T_H1$) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Interleukin-12 (IL-12) is a di-sulfide linked heterodimeric cytokine (p70) composed of two independently regulated subunits, p35 and p40. IL-12 is produced by phagocytic cells and antigen presenting cells, in particular, macrophages and dendritic cells, upon stimulation with bacteria, bacterial products such as lipopolysaccharide (LPS), and intracellular parasites. The well-documented biological functions of IL-12 are induction of interferon-γ expression from T and NK cells and differentiation toward the $T_H1$ T lymphocyte type. IFN-γ, expression of which is induced by IL-12, is a strong and selective enhancer of IL-12 production from monocytes and macrophages. The cytokine IL-23 is a heterodimer composed of a p19 subunit and the same p40 subunit of IL-12. IL-23, similarly to IL-12, is involved in type 1 immune defenses and induces IFN-γ secretion from T cells. IL-27 is formed by the association of EBI3, a polypeptide related to the p40 subunit of IL-12, and p28, a protein related to the p35 subunit of IL-12. IL-27 promotes the growth of T cells and is thought to play a role in the differentiation of $T_H1$ cells. Pflanz et al., *Immunity* (2002), 16:779-790.

It has been suggested that, particularly in chronic diseases in which there is ongoing production of IFN-γ, IL-12 production is augmented by IFN-γ. It is presumed that after an infective or inflammatory stimulus that provokes IL-12 production, the powerful feedback loop promotes IL-12- and IL-23-induced IFN-γ to further augment IL-12 production, leading to consequent excessive production of pro-inflammatory cytokines. Furthermore, it has been suggested that IL-27 induces the expression of T-bet, a major $T_H1$-specific transcription factor, and it's downstream target IL-12R β2, independently of IFN-γ. In addition, IL-27 suppresses the expression of GATA-3. GATA-3 inhibits $T_H1$ development and causes loss of IL-12 signaling through suppression of IL-12R β2 and Stat4 expression. Lucas et al., *PNAS* (2003), 100: 15047-15052.

IL-12 plays a critical role in multiple-$T_H1$ dominant autoimmune diseases including, but not limited to, multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroditis, autoimmune oophoritis and orchitis, autoimmune disease of the adrenal gland; rheumatoid arthritis, juvenile rheumatoid arthritis, systemic lupus erythematosus, scleroderma, polymyositis, dermatomyositis, spondyloarthropathies, ankylosing spondylitis, Sjogren's syndrome and graft-versus-host disease. See, for example, Gately et al. (1998) *Annu Rev Immunol.* 16: 495; and Abbas et al. (1996) *Nature* 383: 787.

Inhibiting IL-12 overproduction, or inhibiting the production of cytokines such as IL-23 and IL-27 which promote IL-12 production and/or $T_H1$ development is an approach to treating the just-mentioned diseases. Trembleau et al. (1995) *Immmunol. Today* 16: 383; and Adorini et al. (1997) *Chem. Immunol.* 68: 175. For example, overproduction of IL-12 and the resultant excessive $T_H1$ type responses can be suppressed by modulating IL-12, IL-23 and/or IL-27 production. Therefore, compounds that down-regulate IL-12, IL-23 and/or IL-27 production can be used for treating inflammatory diseases. Ma et al. (1998) *Eur Cytokine Netw* 9: 54.

SUMMARY

In one aspect, the invention relates to compounds of formula (I):

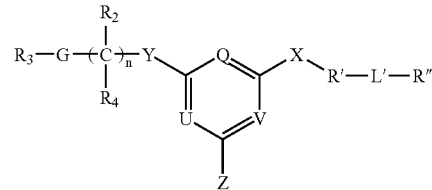

or pharmaceutically acceptable salt, solvate, clathrate, hydrate, or prodrug or polymorph thereof, wherein, each Q, U, and V are independently N or $CR^g$, wherein at least one of Q, U, or V is N;

Z is H, $NR^aR^b$, $OR^f$, $C(O)R^c$, $S(O)_pR^c$, an optionally substituted alkyl, an optionally substituted cycloalkyl, an optionally substituted cyclyl, an optionally substituted aralkyl, an optionally substituted heteroaralkyl, an optionally substituted aryl, an optionally substituted heteroaryl, an optionally substituted heterocyclyl, an optionally substituted heterocyclyl, cyano, nitro, azido, or halo, and with the proviso that Z cannot be:

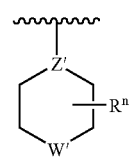

whereby Z' is independently N or CH and W' is independently O, S, S(O), S(O)$_2$, $NR^m$, or $NC(O)R^m$, wherein $R^m$, for each occurrence, is independently —H, alkyl, aryl, heteroaryl, cycloalkyl, heterocycloalkyl, or alkylcarbonyl; $R^n$ is —H, alkyl, alkylcarbonyl, halo, nitro, nitroso, cyano, azido, isothionitro, —$OR^p$ or —$SR^p$; and $R^p$ is —H, alkyl, or alkylcarbonyl;

X is O, S, S(O), S(O)$_2$, $N(R^k)$, C(O), C(S), $C(S)NR^k$, C(NR), $C(NR)NR^k$, $C(O)NR^k$, $C(O)NR^kNR^k$, $C(O)ONR^k$, $C(O)NR^kO$, C(O)O, OC(O), OC(O)O, $(C(R^g)(R^g))_m$, $(C(R^g)(R_g))_mNR^k$, $(C(R^g)(R^g))_mO$, $(C(R^g)(R^g))_mS(O)_p$, $(C(R^g)(R^g))_mN$=$C(R^g)$, $C(R^g)$=N, $C(R^g)$=N—O, $C(R^g)$=N—S $(O)_p$, $C(R^g)=N-NR^k$, $C(R^g)=N-C(CR^g)_2$, $(C(R^g)(R^g))_m$ $C(R^g)=N$, $(C(R^g)(R^g))_m N=N$, $(C(R^g)(R^g))_m C(R^g)=C(R^g)$, $C(R^g)=C(R^g)$, $N=C(R^g)$, $N(R^k)N=C(R^g)$, $N(R^k)C(R^g)=N$, $N(R^k)C(R^g)=C(R^g)$, $N=N$, $N(R^k)N=N$, $NR^kC(O)NR^k$, $NR^kC(S)NR^k$, $NR^kC(O)$, $NR^kC(O)O$, $NR^kC(NR)NR^k$, $NR^kC(S)O$, $NR^kS(O)_pNR^k$, $OC(O)NR^k$, $OC(S)NR^k$, $OC(NR)NR^k$, $OS(O)_pNR^k$, $C(NR)O$, $S(O)_pNR^k$, $S(O)_pNR^kNR^k$;

R, for each occurrence, is independently H, an optionally substituted alkyl, an optionally substituted cycloalkyl, an optionally substituted cyclyl, an optionally substituted heterocycloalkyl, an optionally substituted heterocyclyl, an optionally substituted heteroaryl, an optionally substituted aralkyl, an optionally substituted heteroaralkyl, $-C(O)R^c$, $-OR^k$, $-SR^k$, $-NR^hR^j$, hydroxylalkyl, nitro, cyano, haloalkyl, aminoalkyl, or $-S(O)_2R^c$;

R' is an optionally substituted cycloalkyl, an optionally substituted cyclyl, an optionally substituted heterocycloalkyl, an optionally substituted aryl, an optionally substituted heteroaryl, an optionally substituted aralkyl, an optionally substituted heteroaralkyl, or absent;

L' is O, S, $N(R^k)$, $N(R^k)C(O)$, $C(O)N(R^k)$, C(O)O, or OC(O), or absent; and R" is H, an optionally substituted alkyl, an optionally substituted cycloalkyl, an optionally substituted cyclyl, an optionally substituted heterocycloalkyl, an optionally substituted heterocyclyl, an optionally substituted aryl, an optionally substituted heteroaryl, an optionally substituted aralkyl, an optionally substituted heteroaralkyl, $N(R^k)(CH_2)_nR^g$, $-OR^k$, $-SR^k$, $-NR^hR^j$, hydroxylalkyl, $-C(O)R^c$, $-C(S)R^c$, $-C(NR)R^c$, halo, haloalkyl, aminoalkyl, mercaptoalkyl, cyano, nitro, $-S(O)R^c$, $-S(O)_2R^c$, $-P(O)R^cR^c$, $-P(S)R^cR^c$, or an optionally substituted alkylcarbonylalkyl;

Y is $(CH(R^g))_m$, C(O), C(NR), O, S, S(O), $S(O)_2$, $N(OR^k)$, $N(R^k)$, or absent, $R_3$ is $R^g$, $-C(O)R^c$, $-OC(O)R^c$, $-SC(O)R^c$, $-NR^kC(O)R^c$, $-C(S)R^c$, $-OC(S)R^c$, $-SC(S)R^c$, $-NR^kC(S)R^c$, $-C(NR)R^c$, $-OC(NR)R^c$, $-SC(NR)R^c$, $-NR^kC(NR)R^c$, $-SO_2R^c$, $-S(O)R^c$, $-NR^kSO_2R^c$, $-OS(O)_2R^c$, $-OP(O)R^cR^c$, or $-P(O)R^cR^c$;

$R_2$ and $R_4$ are, independently, H, an optionally substituted alkyl, an optionally substituted alkylcarbonyl, $-OR^k$, $-SR^k$, $-NR^hR^j$, hydroxylalkyl, $-C(O)R^c$, $-OC(O)R^c$, $-SC(O)R^c$, $-NR^kC(O)R^c$, $-C(S)R^c$, $-OC(S)R^c$, $-SC(S)R^c$, $-NR^kC(S)R^c$, $-C(NR)R^c$, $-OC(NR)R^c$, $-SC(NR)R^c$, $-NR^kC(NR)R^c$, $-SO_2R^c$, $-S(O)R^c$, $-NR^kSO_2R^c$, $-OS(O)_2R^c$, $-OP(O)R^cR^c$, $-P(O)R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are $=O$, $=S$, or $=NR$;

$R^a$ and $R^b$, for each occurrence, are independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, $-C(O)R^c$, $-C(S)R^c$, $-C(NR)R^c$, $-NR^hR^j$, $-S(O)R^c$, or $-S(O)^2R^c$; or $R^a$ and $R^b$ taken together with the N to which they are attached is an optionally substituted heterocyclyl, an optionally substituted heterocycloalkyl, or an optionally substituted heteroaryl;

$R^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, $-OR^k$, $-SR^k$, $-NR^hR^j$, hydroxylalkyl, alkylcarbonylalkyl, mercaptoalkyl, aminoalkyl, sulfonylalkyl, sulfonylaryl, or thioalkoxy;

$R^f$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, $-C(O)R^c$, $-C(S)R^c$, $-C(NR)R^c$, $-S(O)R^c$, $-S(O)_2R^c$, $-P(O)R^cR^c$, or $-P(S)R^cR^c$;

$R^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, $-OR^k$, $-SR^k$, $-NR^hR^j$, hydroxylalkyl, alkylcarbonylalkyl, mercaptoalkyl, aminoalkyl, sulfonylalkyl, sulfonylaryl, thioalkoxy, $-C(O)R^c$, $-OC(O)R^c$, $-SC(O)R^c$, $-NR^kC(O)R^c$, $-C(S)R^c$, $-OC(S)R^c$, $-SC(S)R^c$, $-NR^kC(S)R^c$, $-C(NR)R^c$, $-OC(NR)R^c$, $-SC(NR)R^c$, $-NR^kC(NR)R^c$, $-SO_2R^c$, $-S(O)R^c$, $-NR^kSO_2R^c$, $-OS(O)_2R^c$, $-OP(O)R^cR^c$, $-P(O)R^cR^c$, halo, aminoalkyl, mercaptoalkyl, cyano, nitro, nitroso, or azide;

$R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl;

$R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl;

G is: Hydrazide; Hydrazone; Hydrazine; Hydroxylamine; Oxime; Amide; Ester; Carbonate; Carbamate; Thiocarbamate; $-NR^k-C(NR)-NR^k-$; $-NR^k-C(O)-NR^k-$; $-NR^k-C(S)-NR^k-$; $-NR^k-S(O)_2-NR^k-$; Phosphoryl; an optionally substituted -Cyclyl-; an optionally substituted -Heterocyclyl-; an optionally substituted -Aryl-; an optionally substituted -Heteroaryl-; an optionally substituted -Heteroarylalkyl-; an optionally substituted -Heteroaryl-$NR^k$-; an optionally substituted -Heteroaryl-S—; an optionally substituted -Heteroarylalkyl-O—; $-Si(OR^k)_2-$; $-B(OR^k)-$; $-C(NR)-NR^k-$; $-N(R^k)-CR^gR^g-C(O)-$; $-C(O)-ON(R^k)-$; $-C(O)-N(R^k)O-$; $-C(S)-ON(R^k)-$; $-C(S)-N(R^k)O-$; $-C(N(R^k))-ON(R^k)-$;

—C(N(R$^k$))—NR$^k$O—; —OS(O)$_2$—N(R$^k$)N(R$^k$)—; —OC(O)—N(R$^k$)N(R$^k$)—; —OC(S)—N(R$^k$)N(R$^k$)—; —OC(N(R$^k$))—N(R$^k$)N(R$^k$)—; —N(R$^k$)N(R$^k$)S(O)$_2$O—; —N(R$^k$)N(R$^k$)C(S)O—; —N(R$^k$)N(R$^k$)C(N(R$^k$))O—; —OP(O)(R$^c$)O—; —N(R$^k$)P(O)(R$^c$)O—; —OP(O)(R$^c$)N(R$^k$)—; —N(R$^k$)P(O)(R$^c$)N(R$^k$)—; —P(O)(R$^c$)O—; —P(O)(R$^c$)N(R$^k$)—; —N(R$^k$)P(O)(R$^c$)—; —OP(O)(R$^c$)—; —O-alkyl-heterocyclyl-N(R$^k$)—; —N(R$^k$)CHR$^g$C(O)N(R$^k$)CHR$^g$C(O)—; —N(R$^k$)CHR$^g$C(O)—; —N(R$^k$)C(O)CHR$^g$—; —C(O)N(R$^k$)CHR$^g$C(O)—; each of which is optionally substituted; or absent, m, for each occurrence, is independently 1, 2, 3, 4, 5, 6, 7, or 8; n, for each occurrence, is independently 0, 1, 2, 3, 4, 5, 6, or 7; and p, for each occurrence, is independently 0, 1, or 2.

In another aspect, the invention relates to compounds of formula (II):

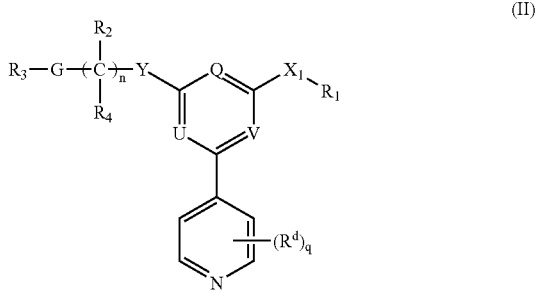

(II)

or a pharmaceutically acceptable salt, solvate, clathrate, hydrate, prodrug or polymorph thereof, wherein:

each Q, U, and V are independently N or CR$^g$, wherein at least one of Q, U, or V is N;

X$_1$ is selected from the group consisting of:

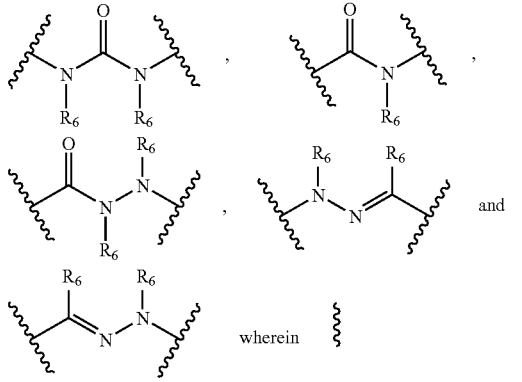

wherein $\xi$ represents the point of attachment;

Y is (CH(R$^g$))$_m$, C(O), C(NR), O, S, S(O), S(O)$_2$, N(OR$^k$), N(R$^k$), or absent;

R$_1$ is a substituted or unsubstituted aryl or a substituted or unsubstituted heteroaryl; in some embodiments R$_1$ is not tetrazolyl, o-methoxyphenyl, 3,4,5-trimethoxyphenyl, a substituted or unsubstituted 4,5-dihydro-1H-benzo[g]indazolyl, a substituted 5-oxo-1,2,3,9b-tetrahydro-pyrrolo[2,1-a]isoindolyl;

R$_3$ is R$^g$, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, or —P(O)R$^c$R$^c$;

R$_2$ and R$_4$ for each occurance, are independently, H, an optionally substituted alkyl, an optionally substituted alkylcarbonyl, —OR$^k$, —SR$^k$, —NR$^h$R$^j$, hydroxylalkyl, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or R$_2$ and R$_4$ taken together are =O, =S, or =NR;

R$_6$ is H or an alkyl;

R$^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, or thioalkoxy;

R$^d$, for each occurrence, is independently, H or a halo;

R$^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the N to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl;

G is a Hydrazide; Hydrazone; Hydrazine; Hydroxylamine; Oxime; Amide; Ester; Carbonate; Carbamate; Thiocarbamate; —NR$^k$—C(NR)—NR$^k$; —NR$^k$—C(O)—NR$^k$—; —NR$^k$—C(S)—NR$^k$—; —NR$^k$—S(O)$_2$—NR$^k$—; Phosphoryl; an optionally substituted -Cyclyl-; an optionally substituted -Heterocyclyl-; an optionally substituted -Aryl-; an optionally substituted -Heteroaryl-; an optionally substituted -Heteroarylalkyl-; an optionally substituted -Heteroaryl-NR$^k$—; an optionally substituted -Heteroaryl-S—; an optionally substituted -Heteroarylalkyl-O—; —Si(OR$^k$)$_2$—; —B(OR$^k$)—; —C(NR)—NR$^k$—; —N(R$^k$)—CR$^g$R$^g$—C(O)—; —C(O)—ON(R$^k$)—; —C(O)—N(R$^k$)O—; —C(S)—ON(R$^k$)—; —C(S)—N(R$^k$)O—; —C(N(R$^k$))—ON(R$^k$)—; —C(N(R$^k$))—NR$^k$O—; —OS(O)$_2$—N(R$^k$)N(R$^k$)—; —OC(O)—N(R$^k$)N(R$^k$)—; —OC(S)—N(R$^k$)N(R$^k$)—; —OC(N(R$^k$))—N(R$^k$)N(R$^k$)—; —N(R$^k$)N(R$^k$)S(O)$_2$O—; —N(R$^k$)N(R$^k$)C(S)O—; —N(R$^k$)N(R$^k$)C(N(R$^k$))O—; —OP(O)(R$^c$)O—; —N(R$^k$)P(O)(R$^c$)O—; —OP(O)(R$^c$)N(R$^k$)—; —N(R$^k$)P(O)(R$^c$)N(R$^k$)—; —P(O)(R$^c$)O—; —P(O)(R$^c$)N(R$^k$)—; —N(R$^k$)P(O)(R$^c$)—; —OP(O)(R$^c$)—; —O-alkyl-heterocyclyl-N(R$^k$)—; —N(R$^k$)CHR$^g$C(O)N(R$^k$)CHR$^g$C(O)—; —N(R$^k$)CHR$^g$C(O)—; —N(R$^k$)C(O)CHR$^g$—; or —C(O)N(R$^k$)CHR$^g$C(O)—; each of which is optionally substituted; or G is absent;

q is 0, 1, 2, 3, or 4; m, for each occurrence, is independently 1, 2, 3, 4, 5, 6, 7, or 8; n, for each occurrence, is independently 0, 1, 2, 3, 4, 5, 6, or 7; and p, for each occurrence, is independently 0, 1, or 2.

In yet another aspect, the invention provides for compounds of formula (III):

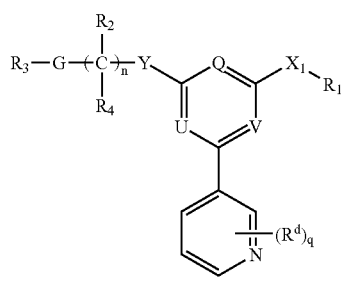

(III)

or a pharmaceutically acceptable salt, solvate, clathrate, hydrate, prodrug or polymorph thereof, wherein:

each Q, U, and V are independently N or CR$^g$, wherein at least one of Q, U, or V is N;

X$_1$ is selected from the group consisting of:

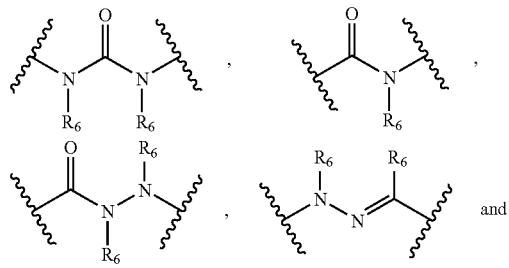

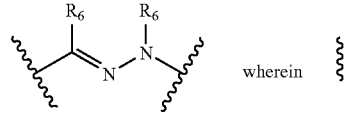 wherein represents the point of attachment;

Y is (CH(R$^g$))$_m$, C(O), C(NR), O, S, S(O), S(O)$_2$, N(OR$^k$), N(R$^k$), or absent;

R$_1$ is a substituted or unsubstituted aryl or a substituted or unsubstituted heteroaryl; in some embodiments R$_1$ is not an unsubstituted pyridinyl or an unsubstituted methanesulfonylphenyl; in other embodiments R$_1$ is not an unsubstituted phenyl, an unsubstituted pyridinyl, 4-methanesulfonylphenyl, tetrazolyl, 4-methoxyphenyl, 4-chlorophenyl, 3-chlorophenyl, or a substituted 5-oxo-1,2,3,9b-tetrahydro-pyrrolo[2,1-a]isoindolyl;

R$_3$ is R$^g$, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, or —P(O)R$^c$R$^c$;

R$_2$ and R$_4$ for each occurance, are independently, H, an optionally substituted alkyl, an optionally substituted alkylcarbonyl, —OR$^k$, —SR$^k$, —NR$^h$R$^j$, hydroxylalkyl, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or R$_2$ and R$_4$ taken together are =O, =S, or =NR;

R$_6$ is H or an alkyl;

R$^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, or thioalkoxy;

R$^d$, for each occurrence, is independently, H or a halo;

R$^g$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, cyano, nitro, nitroso, or azide;

R$^h$ and R$^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or R$^h$ and R$^j$ taken together with the N to which they are attached is an optionally substituted heterocyclyl, an optionally substituted heterocycloalkyl, or an optionally substituted heteroaryl;

R$^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl;

G is a Hydrazide; Hydrazone; Hydrazine; Hydroxylamine; Oxime; Amide; Ester; Carbonate; Carbamate; Thiocarbamate; —NR$^k$—C(NR)—NR$^k$; —NR$^k$—C(O)—NR$^k$—; —NR$^k$—C(S)—NR$^k$—; —NR$^k$—S(O)$_2$—NR$^k$—; Phosphoryl; an optionally substituted -Cyclyl-; an optionally substituted -Heterocyclyl-; an optionally substituted -Aryl-; an optionally substituted -Heteroaryl-; an optionally substituted -Heteroarylalkyl-; an optionally substituted -Heteroaryl-NR$^k$—; an optionally substituted -Heteroaryl-S—; an optionally substituted -Heteroarylalkyl-O—; —Si(OR$^k$)$_2$—; —B(OR$^k$)—; —C(NR)—NR$^k$—; —N(R$^k$)—CR$^g$R$^g$—C(O)—; —C(O)—ON(R$^k$)—; —C(O)—N(R$^k$)O—; —C(S)—ON(R$^k$)—; —C(S)—N(R$^k$)O—; —C(N(R$^k$))—ON(R$^k$)—; —C(N(R$^k$))—NR$^k$O—; —OS(O)$_2$—N(R$^k$)N(R$^k$)—; —OC(O)—N(R$^k$)N(R$^k$)—; —OC(S)—N(R$^k$)N(R$^k$)—; —OC(N(R$^k$))—N(R$^k$)N(R$^k$)—; —N(R$^k$)N(R$^k$)S(O)$_2$O—; —N(R$^k$)N(R$^k$)C(S)O—; —N(R$^k$)N(R$^k$)C(N(R$^k$))O—; —OP(O)(R$^c$)O—; —N(R$^k$)P(O)(R$^c$)O—; —OP(O)(R$^c$)N(R$^k$)—; —N(R$^k$)P(O)(R$^c$)N(R$^k$)—; —P(O)(R$^c$)O—; —P(O)(R$^c$)N(R$^k$)—; —N(R$^k$)P(O)(R$^c$)—; —OP(O)(R$^c$)—; —O-alkyl-heterocyclyl-N(R$^k$)—; —N(R$^k$)CHR$^g$C(O)N(R$^k$)CHR$^g$C(O)—; —N(R$^k$)CHR$^g$C(O)—; —N(R$^k$)C(O)CHR$^g$—; or —C(O)N(R$^k$)CHR$^g$C(O)—; each of which is optionally substituted; or G is absent;

q is 0, 1, 2, 3, or 4; m, for each occurrence, is independently 1, 2, 3, 4, 5, 6, 7, or 8; n, for each occurrence, is independently 0, 1, 2, 3, 4, 5, 6, or 7; and p, for each occurrence, is independently 0, 1, or 2.

In another aspect, this invention features a pharmaceutical composition comprising a pharmaceutically acceptable carrier and a compound of any of the formulae herein or pharmaceutically acceptable salt, solvate, clathrate, hydrate, polymorph, or prodrug thereof.

In another aspect, this invention features a method for treating an interleukin-12 overproduction-related disorder, comprising administering to a subject in need thereof an effective amount of a compound of any of formula (I), formula (II), or formula (III), or pharmaceutically acceptable salt, solvate, clathrate, hydrate, polymorph, or prodrug thereof.

In another aspect, this invention features a method of inhibiting IL-12 production in a subject, comprising administering to the subject an effective amount of a compound of any of the formulae herein or pharmaceutically acceptable salt, solvate, clathrate, hydrate, polymorph, or prodrug thereof.

In another aspect, this invention features a method of inhibiting the proliferation of T$_H$1 lymphocytes in a subject, comprising administering to the subject an effective amount of a compound of any of the formulae herein or pharmaceutically acceptable salt, solvate, clathrate, hydrate, polymorph, or prodrug thereof.

In another aspect, this invention features a method for treating or preventing disorders associated with excessive bone loss, the method comprising administering to a subject in need thereof an effective amount of a compound of any of the formulae herein or pharmaceutically acceptable salt, solvate, clathrate, hydrate, polymorph, or prodrug thereof. The disorder is selected from periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteopetrosis, hypercalcemia of malignancy (HCM), osteolytic bone lesions of multiple myeloma and osteolytic bone metastases of breast cancer, and metastatic cancers.

In another aspect, this invention features a method for inhibiting osteoclast formation in vitro or in vivo, the method comprising contacting a pre-osteoclast cell with an effective amount of a compound of any of the formulae herein or pharmaceutically acceptable salt, solvate, clathrate, hydrate, polymorph, or prodrug thereof.

In another aspect, this invention features a method of treating or preventing a disorder associated with excessive bone resorption by osteoclasts in a subject in need thereof, the method comprising administering to the subject an effective amount of a compound of any of the formulae herein or pharmaceutically acceptable salt, solvate, clathrate, hydrate, polymorph, or prodrug thereof.

In another aspect, this invention features a method of inhibiting IL-23, IL-27, or IL-12 production in a subject, comprising administering to the subject an effective amount of a compound of any of the formulae herein or pharmaceutically acceptable salt, solvate, clathrate, hydrate, polymorph, or prodrug thereof.

Other features, objects, and advantages of the invention will be apparent from the description and from the claims.

DETAILED DESCRIPTION

In one aspect of the invention, the compounds are those of formula I wherein Q, U and V are N. In another aspect of the invention, two of Q, U and V are N, and the other is CR$^g$. In one embodiment, Q and U are N and V is CR$^c$. In another embodiment of the invention, Q and V are N and U is CR$^c$. In another embodiment of the invention, U and V are N and Q is CR$^c$. In another aspect of the invention, one of Q, U, or V is N, and the other two are each CR$^g$. In one embodiment, U is N and Q and V are CR$^c$. In another embodiment of the invention, V is N and Q and U are CR$^c$. In another embodiment of the invention, Q is N and U and V are CR$^c$.

In one aspect of the invention, the compounds are those of formula I wherein Z is NR$^a$R$^b$. In one embodiment, each of R$^a$ and R$^b$ are H, an optionally substituted alkyl, an optionally substituted cyclyl, an optionally substituted cycloalkyl, an optionally substituted heterocyclyl, an optionally substituted heterocycloalkyl, an optionally substituted aryl, an optionally substituted heteroaryl, or —C(O)R$^c$. In a further embodiment of the invention, R$^a$ and R$^b$ are each, independently, H, a lower alkyl, or cycloalkyl. In another embodiment, R$^a$ and R$^b$, together with the nitrogen to which they are attached, form an optionally substituted heterocycloalkyl, an optionally substituted heterocyclyl, or an optionally substituted heteroaryl. In a further embodiment, Z is:

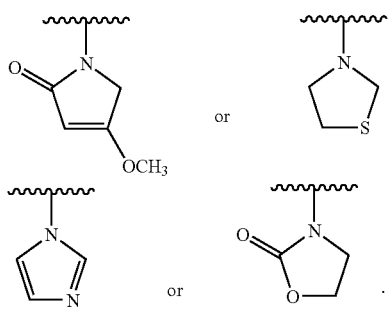

In a further embodiment, Z is selected from the group consisting of:

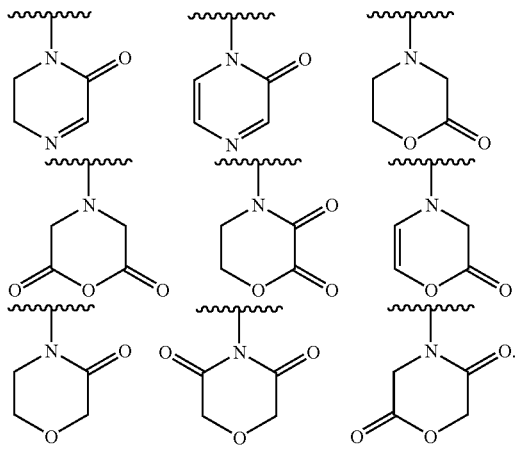

In another aspect of the invention, Z is a group represented by the following structural formula

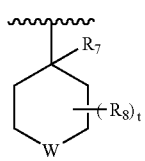

wherein:
W is O, S(O)p, NR$^k$; R$_7$ is an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, cyano, nitro, nitroso, or azide; R$_8$, for each occurrence, is, independently, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, cyano, nitro, nitroso, azide, =O, =S, or =NR; t is 0 or an integer from 1 to 8.

In another aspect, Z is selected from the group consisting of:

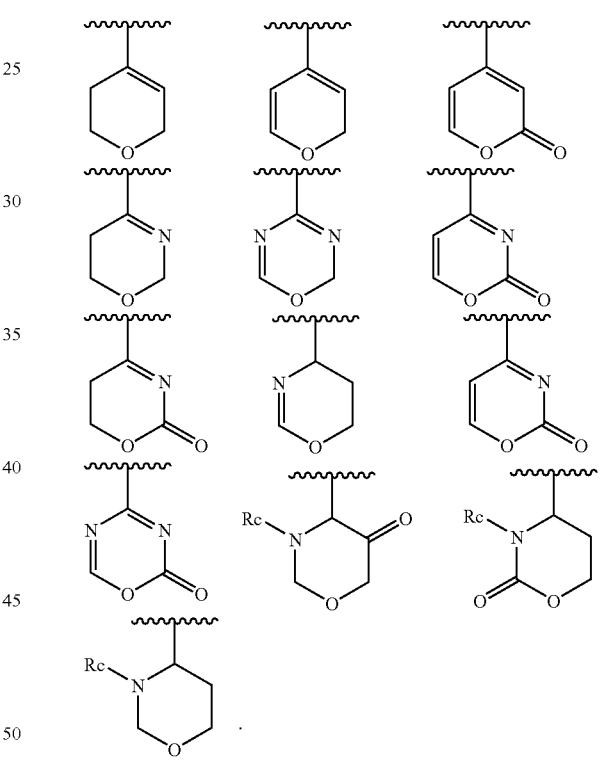

In another aspect of the invention, Z is represented by the following structural formula:

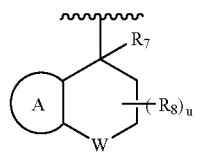

wherein:
Ring A is an optionally substituted 3- to 9-membered cycloalkyl, 3- to 9-membered cyclyl, 3- to 9-membered heterocycloalkyl, 3- to 9-membered heterocyclyl, or 5- to 9-membered aryl, 5- to 9-heteroaryl; W is O, S(O)p, NR$^k$; R$_7$ is an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, cyano, nitro, nitroso, or azide; R$_8$, for each occurrence, is, independently, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaralkyl, an optionally substituted aryl, an optionally substituted heteroaryl, haloalkyl, —OR$^k$, —SR$^k$, —NR$^h$R$^j$, hydroxylalkyl, alkylcarbonylalkyl, mercaptoalkyl, aminoalkyl, sulfonylalkyl, sulfonylaryl, thioalkoxy, —C(O)R$^c$, —OC(O)R$^c$, —SC(O)R$^c$, —NR$^k$C(O)R$^c$, —C(S)R$^c$, —OC(S)R$^c$, —SC(S)R$^c$, —NR$^k$C(S)R$^c$, —C(NR)R$^c$, —OC(NR)R$^c$, —SC(NR)R$^c$, —NR$^k$C(NR)R$^c$, —SO$_2$R$^c$, —S(O)R$^c$, —NR$^k$SO$_2$R$^c$, —OS(O)$_2$R$^c$, —OP(O)R$^c$R$^c$, —P(O)R$^c$R$^c$, halo, cyano, nitro, nitroso, azide, =O, =S, or =NR; u is 0, 1, 2, 3, 4.

In one embodiment, Ring A is an optionally substituted 5- to 6-membered heteroaryl or an optionally substituted 5- to 6-membered aryl. In another embodiment, Ring A is an optionally substituted 5- to 6-membered heterocycloalkyl, an optionally substituted 5- to 6-membered heterocyclyl, an optionally substituted 5- to 6-membered cycloalkyl, or an optionally substituted 5- to 6-membered cyclyl.

In another aspect of the invention, Z is a group represented by the following formula:

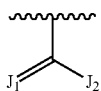

wherein J$_1$ is O, S or NR; and J$_2$ is —OR$^k$, —SR$^k$, or —NR$^h$R$^j$. In a further embodiment, Z is:

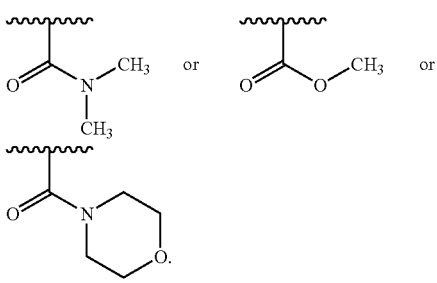

In another aspect of the invention, the compounds are those of formula I wherein Z is OR$^f$. In one embodiment, R$^f$ is H. In another aspect of the invention, the compounds are those of any of the formulae herein wherein Z is H.

In another aspect of the invention, the compounds are those of formula I wherein Z is an optionally substituted aryl or an optionally substituted heteroaryl. In one embodiment, Z is:

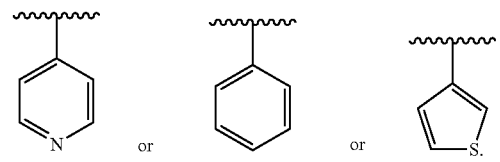

In another aspect of the invention, the compounds are those of any of formula I wherein Z is an optionally substituted alkyl. In one embodiment, Z is a lower alkyl or lower haloalkyl.

In another aspect of the invention, the compounds are those of formula I wherein Z is halogen. In one embodiment, Z is Cl.

In one aspect of the invention, the compounds are those of formula I wherein X is N(R$^k$), N=C(R$^g$), N(R$^k$)N=C(R$^g$), N(R$^k$)C(R$^g$)=N, N(R$^k$)C(R$^g$)=C(R$^g$), N=N, N(R$^k$)N=N, or C(O)NR$^k$. In one embodiment, R$^k$ and R$^g$ are each, independently, H or an alkyl. In a further embodiment, X is N(R$^k$)N=C(R$^g$) or C(R$^g$)=N—N(R$^k$). In a further embodiment, X is N(R$^k$). In a further embodiment, X is C(O)NR$^k$.

In one aspect of the invention, the compounds are those of any of formula I wherein R' and L' are absent. In one embodiment, R" is R" is an optionally substituted aryl, an optionally substituted heteroaryl, an optionally substituted heteroaralkyl, an optionally substituted cycloalkyl, an optionally substituted cyclyl, an optionally substituted heterocycloalkyl or an optionally substituted heterocyclyl. In a further embodiment, R" is an optionally substituted aryl or heteroaryl. In a further embodiment, R" is an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4] pyrimidinyl, or an optionally substituted benzo(b)thienyl.

In one aspect of the invention, the compounds are those of any of formula I wherein Y is $(CH(R^g))_m$, O, $N(OR^k)$, $NR^k$, or absent. In one embodiment, Y is $(CH(R^g))_m$ and $R^g$ is H. In another embodiment, Y is $NR^k$ and $R^k$ is H. In another embodiment, Y is $N(OR^k)$ and $R^k$ is H or a lower alkyl. In another embodiment, m is independently 1, 2, 3, or 4.

In one aspect of the invention, the compounds are those of any of formula I wherein each of $R_2$ and $R_4$ is independently, H, an optionally substituted alkyl, an optionally substituted alkylcarbonyl, an optionally substituted aryl, an optionally substituted heteroaryl, an optionally substituted cyclyl, an optionally substituted heterocyclyl, halo, cyano, hydroxyl, or an optionally substituted alkoxy. In one embodiment, each of $R_2$ and $R_4$ is, independently, H or methyl.

In one aspect of the invention, the compounds are those of formula I wherein $R_3$ is an optionally substituted alkyl, an optionally substituted aryl, an optionally substituted heteroaryl, an optionally substituted cycloalkyl, an optionally substituted cyclyl, an optionally substituted heterocycloalkyl, an optionally substituted heterocyclyl, cyano, halo, $OR^k$, or $NR^hR^j$.

In one embodiment, $R_3$ is an optionally substituted aryl or an optionally substituted heteroaryl. In a further embodiment, $R_3$ is an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl.

In one embodiment, $R_3$ is an optionally substituted heterocycloalkyl. In a further embodiment, $R_3$ is an optionally substituted piperidinyl, an optionally substituted piperazinyl, an optionally substituted 2-oxopiperazinyl, an optionally substituted 2-oxopiperidinyl, an optionally substituted 2-oxopyrrolidinyl, an optionally substituted 4-piperidonyl, an optionally substituted tetrahydropyranyl, an optionally substituted oxazolidinyl, an optionally substituted 2-oxo-oxazolidinyl, an optionally substituted tetrahydrothiopyranyl, an optionally substituted tetrahydrothiopyranyl sulfone, an optionally substituted morpholinyl, an optionally substituted thiomorpholinyl, an optionally substituted thiomorpholinyl sulfoxide, an optionally substituted thiomorpholinyl sulfone, an optionally substituted 1,3-dioxolane, tetrahydrofuranyl, or an optionally substituted tetrahydrothienyl.

In another embodiment, $R_3$ is —$OR^k$ or —$NR^hR^j$, and $R^f$, $R^h$ and $R^j$ are each, independently, H or alkyl.

In one aspect of the invention, the compounds are those of formula I wherein n is independently 0, 1, or 2.

In one aspect of the invention, the compounds are those of formula I wherein G is —C(O)NHNH—, —NHNHC(O)—, —C(O)$NR^kNR^k$—, —$NR^kNR^k$C(O)—, —CH=N—NH—, —NH—N=CH—, —$CR^g$=N—$NR^k$—, —$NR^k$—N=$CR^g$—, —NHNH—, —$NR^kNR^k$—, —NHO—, —O—NH—, —O—$NR^k$—, —$NR^k$—O—, —CH=N—O—, —O—N=CH—, —$CR^g$=N—O—, —O—N=$CR^g$—, —O—C(O)—NH—, —O—C(O)—$NR^k$—, —O—C(S)—NH—, —NH—C(S)—O—, —O—C(S)—$NR^k$—, —$NR^k$—C(S)—O—, —NH—C(NH)—NH—, —$NR^k$—C(NH)—NH—, —$NR^k$—C(NR)—NH—, —NH—C(N(CN))—NH—, —NH—C($NSO_2R^c$)—NH—, —$NR^k$—C($NSO_2R^c$)—NH—, —NH—C($NNO_2$)—NH—, —NH—C(NC(O)$R^c$)—NH—, —NH—C(O)—NH—, —$NR^kC$(O)—$NR^k$—, —NH—C(S)—NH— and —$NR^k$—C(S)—$NR^k$—, —NH—S(O)$_2$—NH—, —$NR^k$—S(O)$_2$—$NR^k$—, —$NR^k$—S(O)$_2$—O—, —P(O)($R^c$)—, —P(O)($R^c$)—O—, —P(O)($R^c$)—$NR^k$—, -Cyclyl-, -Heterocyclyl-, -Aryl-, -Heteroaryl-, -Heteroarylalkyl-, -Heteroaryl-NH—, -Heteroaryl-S—, -Heteroarylalkyl-O—, —C(N—CN)—NH—, —Si(OH)$_2$—, —B(OH)—, —C(NH)—$NR^k$—, —$NR^k$—$CH_2$—C(O)—, —C(O)—$ONR^k$—, —C(O)—$NR^kO$—, —C(S)—$ONR^k$—, —C(S)—$NR^kO$—, —C(NR)—$ONR^k$—, —C(NR)—$NR^kO$—, —OS(O)$_2$—$NR^kNR^k$—, —OC(O)—$NR^kNR^k$—, —OC(S)—$NR^kNR^k$—, —OC(NR)—$NR^kNR^k$—, —$NR^kN$-$R^kS$(O)$_2O$—, —$NR^kNR^kC$(S)O—, —$NR^kNR^kC$(NR)O—, —OP(O)($R^c$)O—, —$NR^kP$(O)($R^c$)O—, —OP(O)($R^c$)N($R^k$)—, —$NR^kP$(O)($R^c$)N($R^k$)—, —P(O)($R^c$)O—, —P(O)($R^c$)$NR^k$—, —$NR^kP$(O)($R^c$)—, —OP(O)($R^c$)—, —O-alkyl-heterocyclyl-N($R^c$)—, —$NR^kCHR^gC$(O)$NR^kCHR^gC$(O)—, —$NR^gCHR^gC$(O)—, —$NR^kC$(O)$CHR^g$—, —C(O) $NR^kCHR^gC$(O)—, or absent.

In one embodiment, G is —C(O)NHNH—, —NHNHC(O)—, —CH=N—NH—, —NH—N=CH—, —NHNH—, —NHO—, —O—NH—, —$NR^k$—O—, —CH=N—O—, —O—N=CH—, —O—C(S)—NH—, or —NH—C(S)—O—. In another embodiment, G is —O—C(O)—NH—, —NH—C(NH)—NH—, —$NR^k$—C(NH)—NH—, —$NR^k$—C(NR)—NH—, —NH—C(N(CN))—NH—, —NH—C($NSO_2R^c$)—NH—, —$NR^k$—C($NSO_2R^c$)—NH—, —NH—C($NNO_2$)—NH—, NH—C(NC(O)$R^k$)—NH—, —NH—C(O)—NH—, or —NH—C(S)—NH—. In another embodiment, G is —NH—S(O)$_2$—NH—, —$NR^k$—S(O)$_2$—O—, —P(O)($R^c$)—, —P(O)($R^c$)—O—, or —P(O)($R^c$)—$NR^k$—.

In another embodiment, G is an optionally substituted cyclyl, an optionally substituted cycloalkyl, an optionally substituted heterocycloalkyl or an optionally substituted heterocyclyl. In a preferred embodiment, G is an optionally substituted cyclopropyl, an optionally substituted cyclobutyl, an optionally substituted cyclopentyl, an optionally substituted cyclohexyl, an optionally substituted cycloheptyl, an optionally substituted aziridinyl, an optionally substituted oxiranyl, an optionally substituted azetidinyl, an optionally substituted oxetanyl, an optionally substituted morpholinyl, an optionally substituted piperazinyl or an optionally substituted piperidinyl.

In another embodiment, G is an optionally substituted aryl, an optionally substituted heteroaryl, an optionally substituted heteroarylalkyl, —C(N═CN)—NH—, —Si(OH)$_2$—, —C(NH)—NR$^k$—, or —NR$^k$—CH$_2$—C(O)—. In a preferred embodiment, G is an optionally substituted imidazolyl, an optionally substituted imidazolidinone, an optionally substituted imidazolidineamine, an optionally substituted pyrrolidinyl, an optionally substituted pyrrolyl, an optionally substituted furanyl, an optionally substituted thienyl, an optionally substituted thiazolyl, an optionally substituted triazolyl, an optionally substituted oxadiazolyl, an optionally substituted thiadiazolyl, an optionally substituted pyrazolyl, an optionally substituted tetrazolyl, an optionally substituted oxazolyl, an optionally substituted isoxazolyl, an optionally substituted phenyl, an optionally substituted pyridyl, an optionally substituted pyrimidyl, an optionally substituted indolyl, or an optionally substituted benzothiazolyl.

Preferred embodiments of the present invention include the compounds of formula I, wherein Z is NR$^a$R$^b$, OR$^f$, H, an optionally substituted aryl, an optionally substituted heteroaryl, halogen, or an optionally substituted alkyl, X is NR$^k$, N═C(R$^g$), N(R$^k$)N═C(R$^g$), N(R$^k$)C(R$^g$)═N, N(R$^k$)C(R$^g$)═C(R$^g$), N═N, N(R$^k$)N═N, or C(O)NR$^k$, and Y is (CH(R$^g$))$_m$, O, N(OR$^k$), NR$^k$, or absent. In a further preferred embodiment, X is N(R$^k$), N(R$^k$)N═C(R$^g$), or C(O)NR$^k$. In another preferred embodiment, Y is (CH(R$^g$))$_m$, or O.

Preferred embodiments of the present invention include the compounds of formula I wherein R' and L' are absent, R'' is an optionally substituted aryl, an optionally substituted heteroaryl, an optionally substituted heteroaralkyl, optionally substituted heterocycloalkyl, or an optionally substituted cycloalkyl; each of R$_2$ and R$_4$ is independently, H, an optionally substituted alkyl, an optionally substituted alkylcarbonyl, an optionally substituted aryl, an optionally substituted heteroaryl, an optionally substituted cyclyl, an optionally substituted cycloalkyl, an optionally substituted heterocycloalkyl, or an optionally substituted heterocyclyl; and R$_3$ is an optionally substituted alkyl, an optionally substituted aryl, an optionally substituted heteroaryl, an optionally substituted cycloalkyl, an optionally substituted heterocycloalkyl, OR$^k$, or NR$^h$R$^j$. In a preferred embodiment, R'' is an optionally substituted aryl, an optionally substituted heteroaryl, an optionally substituted heterocycloalkyl, or an optionally substituted cycloalkyl. In another preferred embodiment, each of R$_2$ and R$_4$ is independently, H or alkyl.

In one aspect, the invention provides for compounds of formula (II), wherein Q, U and V are N. In another aspect, the invention provides a compound of formula (II), wherein two of Q, U and V are N, and the other is CR$^g$. In one embodiment, Q and U are N and V is CR$^g$. In another embodiment, Q and V are N and U is CR$^g$. In still another embodiment, U and V are N and Q is CR$^g$. In another aspect, the invention provides for compounds of formula (II), wherein one of Q, U and V is N, and the other two are each CR$^g$. In one embodiment, U is N and Q and V are CR$^g$. In another embodiment, V is N and Q and U are CR$^g$. In yet another embodiment, Q is N and U and V are CR$^g$.

In another aspect, the invention provides for compounds of formula (II), wherein R$_1$ is an optionally substituted naphthyl, an optionally substituted anthracenyl, an optionally substituted indanyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl; or R$_1$ is a phenyl group which is optionally substituted with one or more substituents selected from the group consisting of a halo, hydroxyl, amino, alkylamino, arylamino, dialkylamino, diarylamino, cyano, nitro, mercapto, mercapto, imino, formyl, carbamido, carbamyl, carboxyl, thioureido, thiocyanato, sulfoamido, sulfonylalkyl, sulfonylaryl, alkyl, alkenyl, alkynyl, cycloalkyl, cyclyl, aryl, aralkyl, heterocycloalkyl, heterocyclyl, heteroaryl, heteroaralkyl, haloalkyl, aryloxy, hydroxyl, hydroxylalkyl, alkylcarbonyl, alkylcarbonylalkyl, alkoxycarbonyl, alkylcarbonyloxy, aryloxycarbonyl, heteroaryloxy, heteroaryloxycarbonyl, mercaptoalkyl, arylsulfonyl, aminoalkyl, alkylcarbonylamino, alkylaminocarbonyl, alkoxycarbonylamino, arylamino-substituted aryl, arylalkylamino, aralkylaminocarbonyl, amido, alkylaminosulfonyl, arylaminosulfonyl, dialkylaminosulfonyl, alkylsulfonylamino, arylsulfonylamino, mercaptoalkoxy, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, S(O)R$^{17}$, or S(O)$_2$R$^{17}$, wherein each alkyl, alkenyl, alkynyl, cycloalkyl, cyclyl, aryl, aralkyl, heterocycloalkyl, heterocyclyl, heteroaryl, or heteroaralkyl, of each phenyl substituent of R$_1$ may be optionally substituted with alkyl, aryl, heteroaryl, halogen, hydroxyl, amino, mercapto, cyano, nitro, oxo (═O), thioxo (═S), or imino (═NR); R$^{15}$ is independently hydrogen, C$_1$-C$_6$ alkyl optionally substituted with cycloalkyl, aryl, heterocyclyl, or heteroaryl; R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl; and R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl; wherein each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halo, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

In one embodiment, R$_1$ is a phenyl group which is optionally substituted with one to five substituents selected from the group consisting of a lower alkyl, a hydroxyl, a halo, an amino, cyano, nitro, a lower alkylamino, a lower dialkylamino, mercapto, lower alkylmercapto, a lower alkenyl, and a lower alkynyl. In a further embodiment, R$_1$ is m-methylphenyl, a 2-hydroxy-5-methylphenyl, or 3,4-dimethylphenyl.

In another aspect, R₁ is an optionally substituted indanyl, an optionally substituted indolyl, an optionally substituted thienyl, an optionally substituted 2,3,4,9-tetrahydro-1H-carbazolyl. Preferably, R₁ is 2,3-dimethyl-1H-indol-5-yl, 4,5-dimethyl-thien-2-yl, or 2,3,4,9-tetrahydro-1H-carbazol-6-yl.

In another aspect, X₁ is a group represented by the following formula:

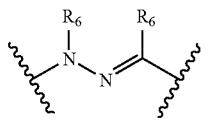

In another aspect, X₁ is a group represented by the following formula:

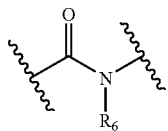

In another aspect, X₁ is a group represented by the following formula:

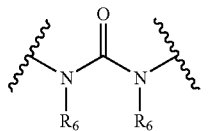

In another aspect, the invention provides for compounds of formula (II), wherein Y is $(CH(R^g))_m$, O, $N(OR^k)$, $NR^k$, or absent. In one embodiment, Y is $(CH(R^g))_m$ and $R^g$ is H. Preferably, m is 0, 1, 2, 3, or 4. In another embodiment, Y is $NR^k$ and $R^k$ is H or a lower alkyl. In another embodiment, Y is $N(OR^k)$ and $R^k$ is H or a lower alkyl. In a further embodiment, each of R₂ and R₄ is independently, H or an alkyl.

In another aspect, R₃ is H, an optionally substituted alkyl, an optionally substituted aryl, an optionally substituted heteroaryl, an optionally substituted cycloalkyl, an optionally substituted cyclyl, an optionally substituted heterocycloalkyl, an optionally substituted heterocyclyl, cyano, halo, $OR^k$, or $NR^hR^j$. In one embodiment, R₃ is an optionally substituted aryl or an optionally substituted heteroaryl. Preferably, R₃ is an optionally substituted phenyl, an optionally substituted naphthyl, an optionally substituted anthracenyl, an optionally substituted indanyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl. In one embodiment, R₃ is an optionally substituted pyridinyl.

In another embodiment, R₃ is an optionally substituted heterocycloalkyl. Preferably, R₃ is an optionally substituted piperidinyl, an optionally substituted piperazinyl, an optionally substituted 2-oxopiperazinyl, an optionally substituted 2-oxopiperidinyl, an optionally substituted 2-oxopyrrolidinyl, an optionally substituted 4-piperidonyl, an optionally substituted tetrahydropyranyl, an optionally substituted oxazolidinyl, an optionally substituted 2-oxo-oxazolidinyl, an optionally substituted tetrahydrothiopyranyl, an optionally substituted tetrahydrothiopyranyl sulfone, an optionally substituted morpholinyl, an optionally substituted thiomorpholinyl, an optionally substituted thiomorpholinyl sulfoxide, an optionally substituted thiomorpholinyl sulfone, an optionally substituted 1,3-dioxolane, tetrahydrofuranyl, or an optionally substituted tetrahydrothienyl. Preferably, R₃ is an optionally substituted morpholinyl.

In another embodiment, R₃ is $—OR^k$ or $—NR^hR^j$, and $R^f$, $R^h$ and $R^j$ are each, independently, H or alkyl.

In certain embodiment, n is 0, 1, 2, or 3. In other certain embodiment, G is —C(O)NHNH—, —NHNHC(O)—, —C(O)NR$^k$NR$^k$—, —NR$^k$NR$^k$C(O)—, —CH=N—NH—, —NH—N=CH—CR$^g$=N—NR$^k$—, —NR$^k$—N=CR$^g$—, —NHNH—, —NR$^k$NR$^k$—, —NHO— —O—NH—, —O—NR$^k$—, —NR$^k$—O—, —CH=N—O—, —O—N=CH—, —CR$^g$=N—O—, —O—N=CR$^g$—, —O—C(O)—NH—, —O—C(O)—NR$^k$—, —O—C(S)—NH—, —NH—C(S)—O—, —O—C(S)—NR$^k$—, —NR$^k$—C(S)—O—, —NH—C(NH)—NH—, —NR$^k$—C(NH)—NH—, —NR$^k$—C(NR)—NH—, —NH—C(N(CN))—NH—, —NH—C(NSO₂R$^c$)—NH—, —NR$^k$—C(NSO₂R$^c$)—NH—, —NH—C(NNO₂)—NH—, —NH—C(NC(O)R$^c$)—NH—, —NH—C(O)—NH—, —NR$^k$—C(O)—NR$^k$—, —NH—C(S)—NH— and —NR$^k$—C(S)—NR$^k$—, —NH—S(O)₂—NH—, —NR$^k$—S(O)₂—NR$^k$—, —NR$^k$—S(O)₂—O—, —P(O)(R$^c$)—, —P(O)(R$^c$)—O—, —P(O)(R$^c$)—NR$^k$—, -Cyclyl-, -Heterocyclyl-, -Aryl-, -Heteroaryl-, -Heteroarylalkyl-, -Heteroaryl-NH—, -Heteroaryl-S—, -Heteroarylalkyl-O—, —C(N=CN)—NH—, —Si(OH)₂—, —B(OH)—, —C(NH)—NR$^k$—, —NR$^k$—CH₂—C(O)—, —C(O)—ONR$^k$—, —C(O)—NR$^k$O—, —C(S)—ONR$^k$—, —C(S)—NR$^k$O—, —C(NR)—ONR$^k$—, —C(NR)—NR$^k$O—, —OS(O)₂—NR$^k$NR$^k$—, —OC(O)—NR$^k$NR$^k$—, —OC(S)—NR$^k$NR$^k$—, —OC(NR)—NR$^k$NR$^k$—, —NR$^k$NR$^k$S(O)₂O—, —NR$^k$NR$^k$C(S)O—, —NR$^k$NR$^k$C(NR)O—, —OP(O)(R$^c$)O—, —NR$^k$P(O)(R$^c$)O—, —OP(O)(R$^c$)N(R$^k$)—, —NR$^k$P(O)(R$^c$)N(R$^k$)—, —P(O)(R$^c$)O—, —P(O)(R$^c$)NR$^k$—, —NR$^k$P(O)(R$^c$)—, —OP(O)(R$^c$)—, —O-alkyl-heterocyclyl-N(R$^c$)—, —NR$^k$CHR$^g$C(O)NR$^k$CHR$^g$C(O)—, —NR$^g$CHR$^g$C(O)—, —NR$^k$C(O)CHR$^g$—, —C(O)NR$^k$CHR$^g$C(O)—, or absent. In a further embodiment, G is —C(O)NHNH—, —NHNHC(O)—, —CH=N—NH—, —NH—N=CH—, —NHNH—, —NHO—, —O—NH—, —NR$^k$—O—, —CH=N—O—, —O—N=CH—, —O—C(S)—NH—, or —NH—C(S)—O—. In another preferred embodiment, G is —O—C(O)—NH—, —NH—C(NH)—NH—, —NR$^k$—C(NH)—NH—, —NR$^k$—C(NR)—NH, —NH—C(N(CN))—NH—, —NH—C(NSO$_2$R$^c$)—NH—, —NR$^k$—C(NSO$_2$R$^c$)—NH—, —NH—C(NNO$_2$)—NH—, NH—C(NC(O)R$^k$)—NH—, —NH—C(O)—NH—, or —NH—C(S)—NH—. In yet another preferred embodiment, G is —NH—S(O)$_2$—NH—, —NR$^k$—S(O)$_2$—O—, —P(O)(R$^c$)—, —P(O)(R$^c$)—O—, or —P(O)(R$^c$)—NR$^k$—.

In another embodiment, G is an optionally substituted cyclyl, an optionally substituted cycloalkyl, an optionally substituted heterocycloalkyl or an optionally substituted heterocyclyl. Preferably, G is an optionally substituted cyclopropyl, an optionally substituted cyclobutyl, an optionally substituted cyclopentyl, an optionally substituted cyclohexyl, an optionally substituted cycloheptyl, an optionally substituted aziridinyl, an optionally substituted oxiranyl, an optionally substituted azetidinyl, an optionally substituted oxetanyl, an optionally substituted morpholinyl, an optionally substituted piperazinyl or an optionally substituted piperidinyl.

In another embodiment, G is an optionally substituted aryl, an optionally substituted heteroaryl, an optionally substituted heteroarylalkyl, —C(N=CN)—NH—, —Si(OH)$_2$—, —C(NH)—NR$^k$—, or —NR$^k$—CH$_2$—C(O)—. Preferably, G is an optionally substituted imidazolyl, an optionally substituted imidazolidinone, an optionally substituted imidazolidineamine, an optionally substituted pyrrolidinyl, an optionally substituted pyrrolyl, an optionally substituted furanyl, an optionally substituted thienyl, an optionally substituted thiazolyl, an optionally substituted triazolyl, an optionally substituted oxadiazolyl, an optionally substituted thiadiazolyl, an optionally substituted pyrazolyl, an optionally substituted tetrazolyl, an optionally substituted oxazolyl, an optionally substituted isoxazolyl, an optionally substituted phenyl, an optionally substituted pyridyl, an optionally substituted pyrimidyl, an optionally substituted indolyl, or an optionally substituted benzothiazolyl.

In another embodiment, G is absent. In a preferred embodiment, Y is absent, n is 0, and R$_3$ is H.

In one aspect, the invention provides for compounds of formula (III), wherein Q, U and V are N. In another aspect, the invention provides for compounds of formula (III) wherein two of Q, U and V are N, and the other is CR$^g$. In one embodiment, Q and U are N and V is CR$^g$. In another embodiment, Q and V are N and U is CR$^g$. In still another embodiment, U and V are N and Q is CR$^g$. In another aspect, the invention provides for compounds of fomula (III) wherein one of Q, U and V is N, and the other two are each CR$^g$. In one embodiment, U is N and Q and V are CR$^g$. In another embodiment, V is N and Q and U are CR$^g$. In yet another embodiment, Q is N and U and V are CR$^g$.

In another aspect, the invention provides for compounds of formula (III), wherein R$_1$ is an optionally substituted naphthyl, an optionally substituted anthracenyl, an optionally substituted indanyl, an optionally substituted fluorenyl, an optionally substituted indenyl, an optionally substituted azulenyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl; or R$_1$ is a phenyl or pyridinyl group which can be optionally substituted with one or more substituents selected from the group consisting of a fluoro, bromo, iodo, hydroxyl, amino, alkylamino, arylamino, dialkylamino, diarylamino, cyano, nitro, mercapto, mercapto, imino, formyl, carbamido, carbamyl, carboxyl, thioureido, thiocyanato, sulfoamido, sulfonylalkyl, sulfonylaryl, alkyl, alkenyl, alkynyl, cycloalkyl, cyclyl, aryl, aralkyl, heterocycloalkyl, heterocyclyl, heteroaryl, heteroaralkyl, haloalkyl, aryloxy, hydroxyl, hydroxylalkyl, alkylcarbonyl, alkylcarbonylalkyl, alkoxycarbonyl, alkylcarbonyloxy, aryloxycarbonyl, heteroaryloxy, heteroaryloxycarbonyl, mercaptoalkyl, arylsulfonyl, aminoalkyl, alkylcarbonylamino, alkylaminocarbonyl, alkoxycarbonylamino, arylamino-substituted aryl, arylalkylamino, aralkylaminocarbonyl, amido, alkylaminosulfonyl, arylaminosulfonyl, dialkylaminosulfonyl, alkylsulfonylamino, arylsulfonylamino, mercaptoalkoxy, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, or S(O)R$^{17}$, wherein each alkyl, alkenyl, alkynyl, cycloalkyl, cyclyl, aryl, aralkyl, heterocycloalkyl, heterocyclyl, heteroaryl, or heteroaralkyl, of each phenyl substituent of R$_1$ may be optionally substituted with alkyl, aryl, heteroaryl, halogen, hydroxyl, amino, mercapto, cyano, nitro, oxo (=O), thioxo (=S), or imino (=NR); R$^{15}$ is independently hydrogen, C$_1$-C$_6$ alkyl optionally substituted with cycloalkyl, aryl, heterocyclyl, or heteroaryl; R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl; and R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl; wherein each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halo, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

In a further embodiment, R$_1$ is a phenyl group which is substituted with one to five substituents selected from the group consisting of a lower alkyl, a hydroxyl, fluoro, bromo, iodo, an amino, cyano, nitro, a lower alkylamino, a lower dialkylamino, mercapto, lower alkylmercapto, a lower alkenyl, and a lower alkynyl. Preferably, R$_1$ is m-methylphenyl, a 2-hydroxy-5-methylphenyl, or 3,4-dimethylphenyl.

In another embodiment, R$_1$ is an optionally substituted indanyl, an optionally substituted indolyl, an optionally substituted thienyl, an optionally substituted 2,3,4,9-tetrahydro- 1H-carbazolyl. Preferably, $R_1$ is 2,3-dimethyl-1H-indol-5-yl, 4,5-dimethyl-thien-2-yl, or 2,3,4,9-tetrahydro-1H-carbazol-6-yl.

In one embodiment, $X_1$ is a group represented by the following formula:

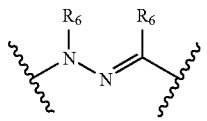

In another embodiment, $X_1$ is a group represented by the following formula:

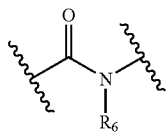

In another embodiment, $X_1$ is a group represented by the following formula:

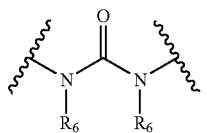

In certain embodiments, Y is $(CH(R^g))_m$, O, $N(OR^k)$, $NR^k$, or absent. In a further embodiment, Y is $(CH(R^g))_m$ and $R^g$ is H. Preferably, m is 0, 1, 2, 3, or 4. In another embodiment, Y is $NR^k$ and $R^k$ is H or a lower alkyl. In another embodiment, Y is $N(OR^k)$, and $R^k$ is H or a lower alkyl. In another embodiment, each of $R_2$ and $R_4$ is independently, H or an alkyl.

In another embodiment, $R_3$ is H, an optionally substituted alkyl, an optionally substituted aryl, an optionally substituted heteroaryl, an optionally substituted cycloalkyl, an optionally substituted cyclyl, an optionally substituted heterocycloalkyl, an optionally substituted heterocyclyl, cyano, halo, $OR^k$, or $NR^hR^j$. Preferably, $R_3$ is an optionally substituted aryl or an optionally substituted heteroaryl. In a further embodiment, $R_3$ is an optionally substituted phenyl, an optionally substituted naphthyl, an optionally substituted anthracenyl, an optionally substituted indanyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl.

In certain embodiments, $R_3$ is an optionally substituted pyridinyl. In another embodiment, $R_3$ is an optionally substituted heterocycloalkyl. Preferably, $R_3$ is an optionally substituted piperidinyl, an optionally substituted piperazinyl, an optionally substituted 2-oxopiperazinyl, an optionally substituted 2-oxopiperidinyl, an optionally substituted 2-oxopyrrolidinyl, an optionally substituted 4-piperidonyl, an optionally substituted tetrahydropyranyl, an optionally substituted oxazolidinyl, an optionally substituted 2-oxo-oxazolidinyl, an optionally substituted tetrahydrothiopyranyl, an optionally substituted tetrahydrothiopyranyl sulfone, an optionally substituted morpholinyl, an optionally substituted thiomorpholinyl, an optionally substituted thiomorpholinyl sulfoxide, an optionally substituted thiomorpholinyl sulfone, an optionally substituted 1,3-dioxolane, tetrahydrofuranyl, or an optionally substituted tetrahydrothienyl. Preferably, $R_3$ is an optionally substituted morpholinyl.

In another further embodiment, $R_3$ is $—OR^k$ or $—NR^hR^j$, and $R^f$, $R^h$ and $R^j$ are each, independently, H or alkyl. In a further embodiment, n is 0, 1, 2, or 3.

In another embodiment, G is —C(O)NHNH—, —NHNHC(O)—, —C(O)NR$^k$NR$^k$—, —NR$^k$NR$^k$C(O)—, —CH=N—NH—, —NH—N=CH—CR$^g$=N—NR$^k$—, —NR$^k$—N=CR$^g$—, —NHNH—, —NR$^k$NR$^k$, —NHO— —O—NH—, —O—NR$^k$—, —NR$^k$—O—, —CH=N—O—, —O—N=CH—, —CR$^g$=N—O—, —O—N=CR$^g$—, —O—C(O)—NH—, —O—C(O)—NR$^k$—, —O—C(S)—NH—, —NH—C(S)—O—, —O—C(S)—NR$^k$—, —NR$^k$—C(S)—O—, —NH—C(NH)—NH—, —NR$^k$—C(NH)—NH—, —NR$^k$—C(NR)—NH—, —NH—C(N(CN))—NH—, —NH—C(NSO$_2$R$^c$)—NH—, —NR$^k$—C(NSO$_2$R$^c$)—NH—, —NH—C(NNO$_2$)—NH—, —NH—C(NC(O)R$^c$)—NH—, —NH—C(O)—NH—, —NR$^k$—C(O)—NR$^k$—, —NH—C(S)—NH— and —NR$^k$—C(S)—NR$^k$—, —NH—S(O)$_2$—NH—, —NR$^k$—S(O)$_2$—NR$^k$—, —NR$^k$—S(O)$_2$—O—, —P(O)(R$^c$)—, —P(O)(R$^c$)—O—, —P(O)(R$^c$)—NR$^k$, -Cyclyl-, -Heterocyclyl-, -Aryl-, -Heteroaryl-, -Heteroarylalkyl-, -Heteroaryl-NH—, -Heteroaryl-S—, -Heteroarylalkyl-O—, —C(N—CN)—NH—, —Si(OH)$_2$—, —B(OH)—, —C(NH)—NR$^k$—, —NR$^k$—CH$_2$—C(O)—, —C(O)—ONR$^k$—, —C(O)—NR$^k$O—, —C(S)—ONR$^k$—, —C(S)—NR$^k$O—, —C(NR)—ONR$^k$—, —C(NR)—NR$^k$O—, —OS(O)$_2$—NR$^k$NR$^k$—, —OC(O)—NR$^k$NR$^k$—, —OC(S)—NR$^k$NR$^k$—, —OC(NR)—NR$^k$NR$^k$—, —NR$^k$NR$^k$S(O)$_2$O—, —NR$^k$N-R$^k$C(S)O—, —NR$^k$NR$^k$C(NR)O—, —OP(O)(R$^c$)O—, —NR$^k$P(O)(R$^c$)O—, —OP(O)(R$^c$)N(R$^k$)—, —NR$^k$P(O)(R$^c$)N(R$^k$)—, —P(O)(R$^c$)O—, —P(O)(R$^c$)NR$^k$—, —NR$^k$P(O)(R$^c$)—, —OP(O)(R$^c$)—, —O-alkyl-heterocyclyl-N(R$^c$)—, —NR$^k$CHR$^g$C(O)NR$^k$CHR$^g$C(O)—, —NR$^g$CHR$^g$C(O)—, —NR$^k$C(O)CHR$^g$—, —C(O)NR$^k$CHR$^g$C(O)—, or absent. In a further embodiment, G is —C(O)NHNH—, —NHNHC(O)—, —CH=N—NH—, —NH—N=CH—, —NHNH—, —NHO—, —O—NH—, —NR$^k$—O—, —CH=N—O—, —O—N=CH—, —O—C(S)—NH—, or —NH—C(S)—O—. In a further embodiment, G is —O—C(O)—NH—, —NH—C(NH)—NH—, —NR$^k$—C(NH)—NH—, —NR$^k$—C(NR)—NH—, —NH—C(N(CN))—NH—, —NH—C(NSO$_2$R$^c$)—NH—, —NR$^k$—C(NSO$_2$R$^c$)—NH—, —NH—C(NNO$_2$)—NH—, NH—C(NC(O)R$^k$)—NH—, —NH—C(O)—NH—, or —NH—C(S)—NH—. In a further embodiment, G is —NH—S(O)$_2$—NH—, —NR$^k$—S(O)$_2$—O—, —P(O)(R$^c$)—, —P(O)(R$^c$)—O—, or —P(O)(R$^c$)—NR$^k$—.

In one embodiment, G is an optionally substituted cyclyl, an optionally substituted cycloalkyl, an optionally substituted heterocycloalkyl or an optionally substituted heterocyclyl. In a further embodiment, G is an optionally substituted cyclopropyl, an optionally substituted cyclobutyl, an optionally substituted cyclopentyl, an optionally substituted cyclohexyl, an optionally substituted cycloheptyl, an optionally substituted aziridinyl, an optionally substituted oxiranyl, an optionally substituted azetidinyl, an optionally substituted oxetanyl, an optionally substituted morpholinyl, an optionally substituted piperazinyl or an optionally substituted piperidinyl.

In another embodiment, G is an optionally substituted aryl, an optionally substituted heteroaryl, an optionally substituted heteroarylalkyl, —C(N—CN)—NH—, —Si(OH)$_2$—, —C(NH)—NR$^k$—, or —NR$^k$—CH$_2$—C(O)—. In a further embodiment, G is an optionally substituted imidazolyl, an optionally substituted imidazolidinone, an optionally substituted imidazolidineamine, an optionally substituted pyrrolidinyl, an optionally substituted pyrrolyl, an optionally substituted furanyl, an optionally substituted thienyl, an optionally substituted thiazolyl, an optionally substituted triazolyl, an optionally substituted oxadiazolyl, an optionally substituted thiadiazolyl, an optionally substituted pyrazolyl, an optionally substituted tetrazolyl, an optionally substituted oxazolyl, an optionally substituted isoxazolyl, an optionally substituted phenyl, an optionally substituted pyridyl, an optionally substituted pyrimidyl, an optionally substituted indolyl, or an optionally substituted benzothiazolyl.

In another embodiment, G is absent. In a further embodiment, Y is absent, n is 0, and R$_3$ is H.

Preferred compounds of the present invention include:

(1) Diisopropyl-{4-methoxy-6-[N'-(1-methyl-1H-indol-3-ylmethylene)-hydrazino]-[1,3,5]triazin-2-yl}-amine

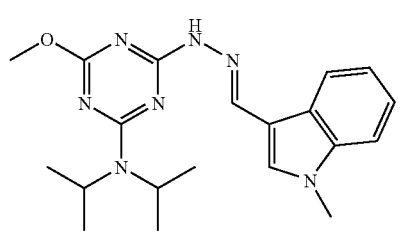

(2) {4-[N'-(1H-Indol-3-ylmethylene)-hydrazino]-6-methoxy-[1,3,5]triazin-2-yl}-diisopropyl-amine

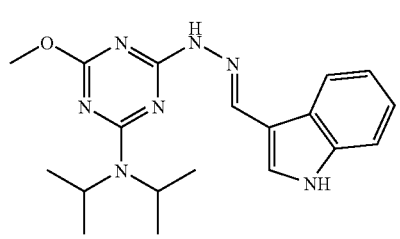

(3) Diisopropyl-{4-methoxy-6-[N'-(7-methyl-1H-indol-3-ylmethylene)-hydrazino]-[1,3,5]triazin-2-yl}-amine

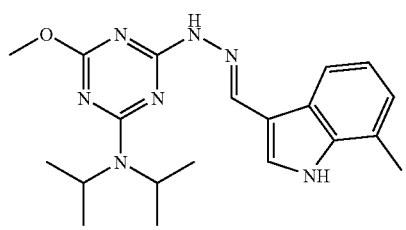

(4) {4-[N'-(5-Fluoro-1H-indol-3-ylmethylene)-hydrazino]-6-methoxy-[1,3,5]triazin-2-yl}-diisopropyl-amine

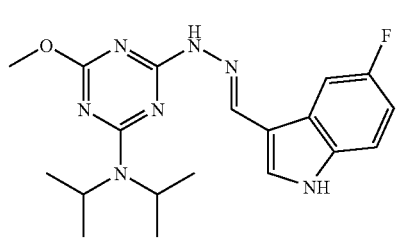

(5) 1-{3-[(4-Diisopropylamino-6-methoxy-[1,3,5]triazin-2-yl)-hydrazonomethyl]-indol-1-yl}-ethanone

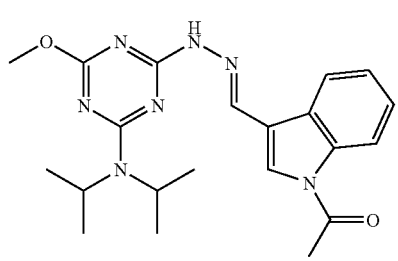

(6) [4-[N'-(1H-Indol-3-ylmethylene)-hydrazino]-6-(2-pyridin-2-yl-ethoxy)-[1,3,5]triazin-2-ylamino]-acetic acid methyl ester

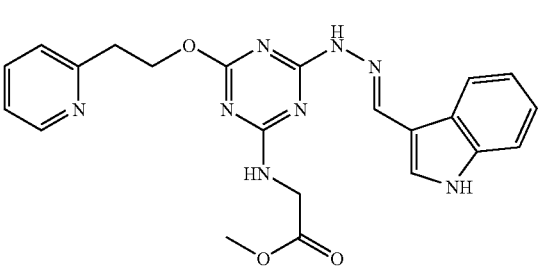

(7) N-{4-[2-(3,4-Dimethoxy-phenyl)-ethoxy]-6-thiazolidin-3-yl-[1,3,5]triazin-2-yl}-N'-(1H-indol-3-ylmethylene)-hydrazine

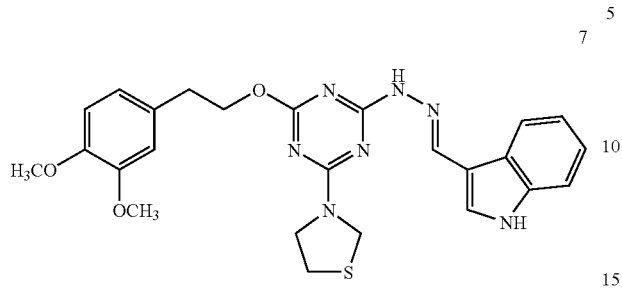

(8) N-[4-(1,4-Dioxa-8-aza-spiro[4.5]dec-8-yl)-6-(2-pyridin-2-yl-ethoxy)-[1,3,5]triazin-2-yl]-N'-(1H-indol-3-ylmethylene)-hydrazine

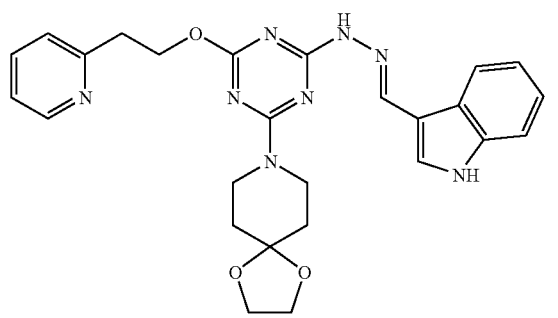

(9) [4-[N'-(1H-Indol-3-ylmethylene)-hydrazino]-6-(2-pyridin-2-yl-ethoxy)-[1,3,5]triazin-2-ylamino]-acetonitrile

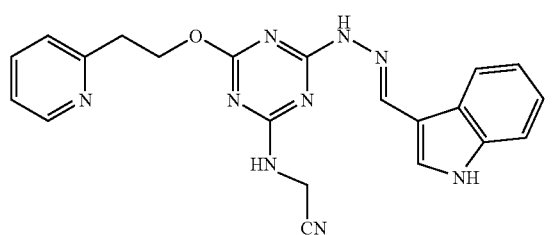

(10) N-(1H-Indol-3-ylmethylene)-N'-[4-(2-pyridin-2-yl-ethoxy)-6-(tetrahydro-pyran-4-yloxy)-[1,3,5]triazin-2-yl]-hydrazine

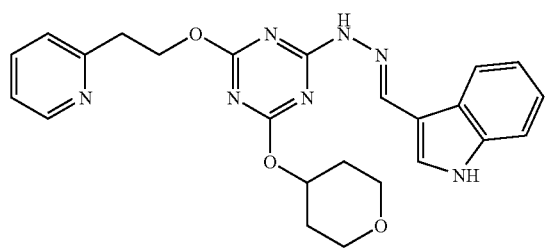

(11) 1-[4-[N'-(1H-Indol-3-ylmethylene)-hydrazino]-6-(2-pyridin-2-yl-ethoxy)-[1,3,5]triazin-2-yl]-piperidin-4-one

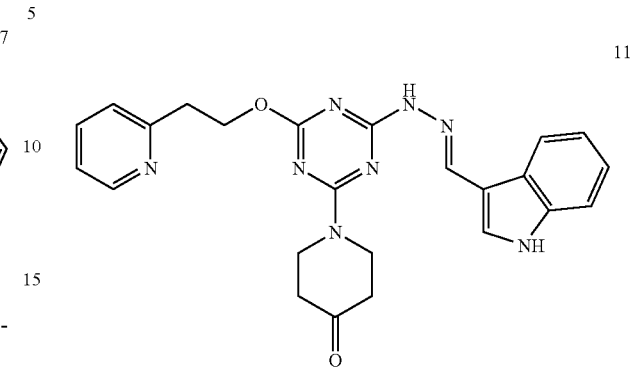

(12) N-(3-Methyl-benzylidene)-N'-[6-piperidin-1-yl-2-(2-pyridin-2-yl-ethoxy)-pyrimidin-4-yl]-hydrazine

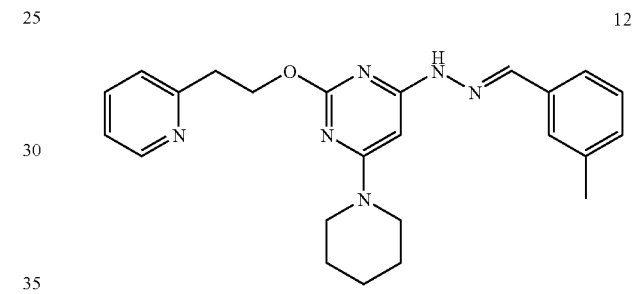

(13) Bis-(2-methoxy-ethyl)-[6-[N'-(3-methyl-benzylidene)-hydrazino]-2-(2-pyridin-2-yl-ethoxy)-pyrimidin-4-yl]-amine

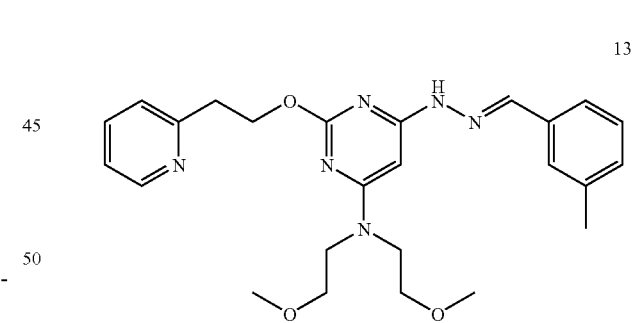

(14) [2-(3,4-Dimethoxy-phenyl)-ethyl]-{4-methyl-6-[N'-(3-methyl-benzylidene)-hydrazino]-pyrimidin-2-yl}-amine

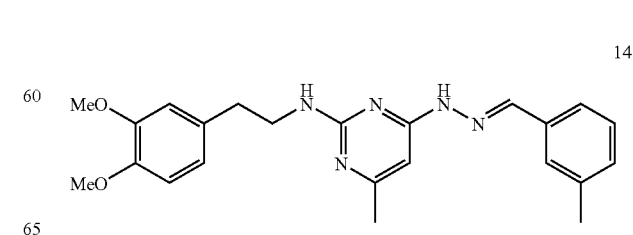

(15) {2-[2-(3,4-Dimethoxy-phenyl)-ethoxy]-6-[N'-(3-methyl-benzylidene)-hydrazino]-pyrimidin-4-yl}-dimethyl-amine

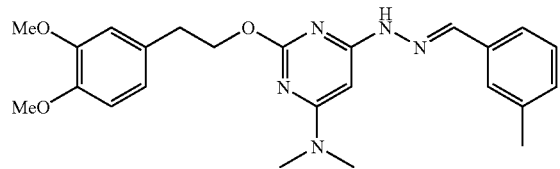

(16) {6-[2-(3,4-Dimethoxy-phenyl)-ethoxy]-2-[N'-(3-methyl-benzylidene)-hydrazino]-pyrimidin-4-yl}-dimethyl-amine

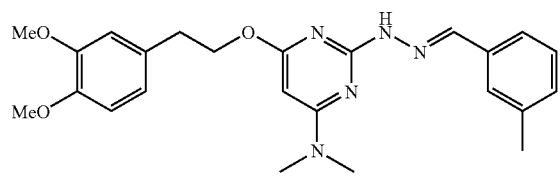

(17) [2-(3,4-Dimethoxy-phenyl)-ethyl]-{4-[N'-(3-methyl-benzylidene)-hydrazino]-pyrimidin-2-yl}-amine

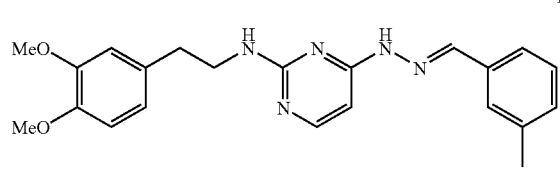

(18) Dimethyl-[2-[N'-(3-methyl-benzylidene)-hydrazino]-6-(2-morpholin-4-yl-ethoxy)-pyridin-4-yl]-amine

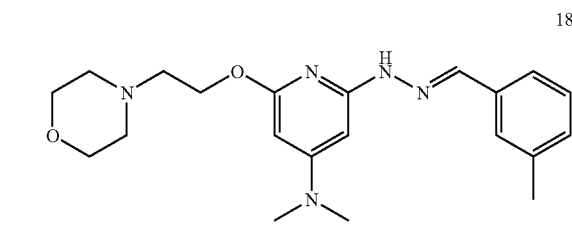

(19) 2,6-Bis-[N'-(3-methyl-benzylidene)-hydrazino]-pyrimidin-4-ylamine

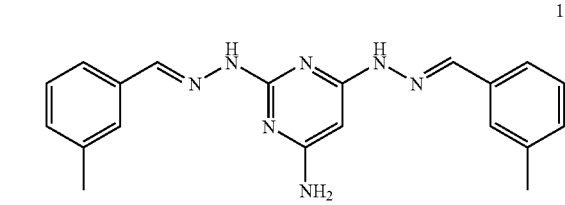

(20) N-{4-[2-(3,4-Dimethoxy-phenyl)-ethoxy]-6-thiophen-3-yl-[1,3,5]triazin-2-yl}-N'-isopropylidene-hydrazine

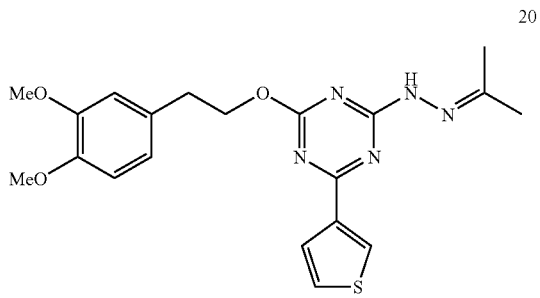

(21) N-{4-[2-(3,4-Dimethoxy-phenyl)-ethoxy]-6-imidazol-1-yl-[1,3,5]triazin-2yl}-N'-(3-methyl-benzylidene)-hydrazine

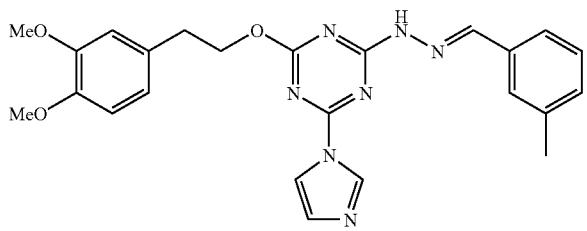

(22) N-{4-Chloro-6-[2-(3,4-dimethoxy-phenyl)-ethoxy]-[1,3,5]triazin-2-yl}-N'-(3-methyl-benzylidene)-hydrazine

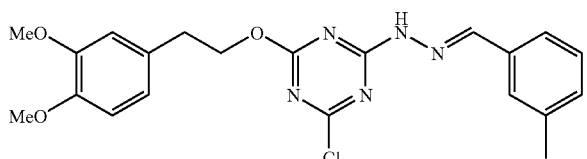

(23) N-{4-[2-(3,4-Dimethoxy-phenyl)-ethoxy]-6-phenyl-[1,3,5]triazin-2-yl}-N'-(3-methyl-benzylidene)-hydrazine

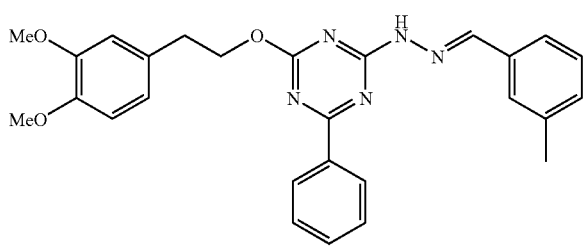

(24) N-{4-[2-(3,4-Dimethoxy-phenyl)-ethoxy]-6-thiophen-3-yl-[1,3,5]triazin-2-yl}-N'-(3-methyl-benzylidene)-hydrazine

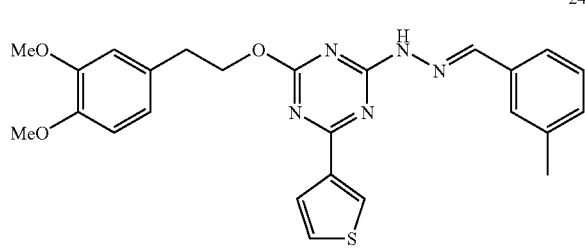

(25) N-(3-Methyl-benzylidene)-N'-[2-(2-pyridin-2-yl-ethoxy)-6-pyrrolidin-1-yl-pyrimidin-4-yl]-hydrazine

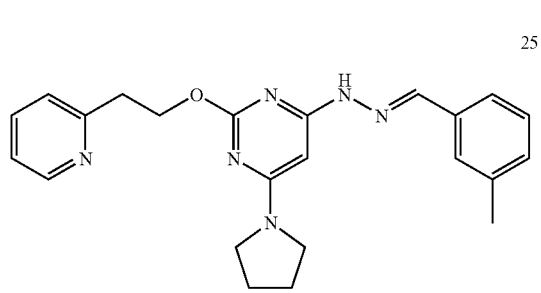

(26) N-[6-Azetidin-1-yl-2-(2-pyridin-2-yl-ethoxy)-pyrimidin-4-yl]-N'-(3-methyl-benzylidene)-hydrazine

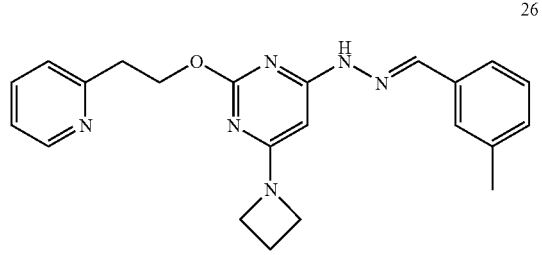

(27) 3-{6-Dimethylamino-2-[N'-(3-methyl-benzylidene)-hydrazino]-pyrimidin-4-yl}-propan-1-ol

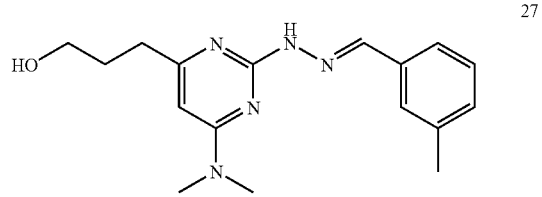

(28) (4-Nitro-phenyl)-carbamic acid 3-{6-dimethylamino-2-[N'-(3-methyl-benzylidene)-hydrazino]-pyrimidin-4-yl}-propyl ester

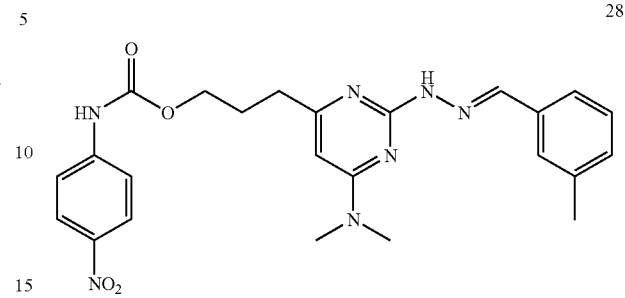

(29) (4-Trifluoromethyl-phenyl)-carbamic acid 3-{6-dimethylamino-2-[N'-(3-methyl-benzylidene)-hydrazino]-pyrimidin-4-yl}-propyl ester

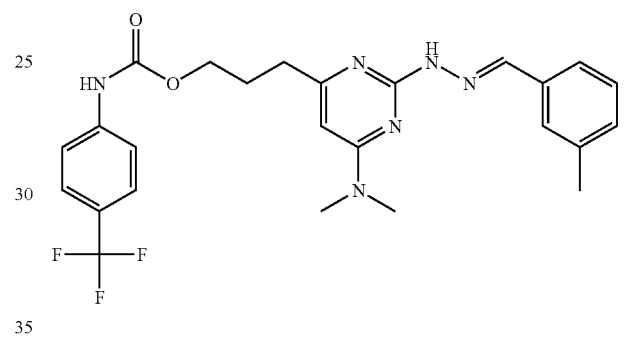

(30) Diethyl-[6-[N'-(3-methyl-benzylidene)-hydrazino]-2-(2-morpholin-4-yl-ethoxy)-pyrimidin-4-yl]-amine

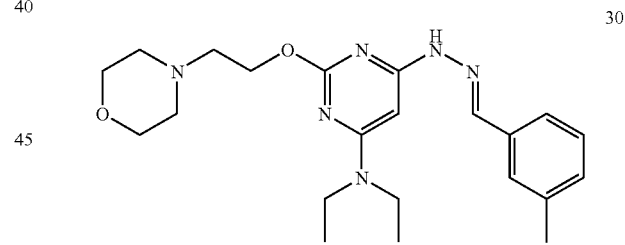

(31) (2-Methoxy-ethyl)-methyl-[6-[N'-(3-methyl-benzylidene)-hydrazino]-2-(2-morpholin-4-yl-ethoxy)-pyrimidin-4-yl]-amine

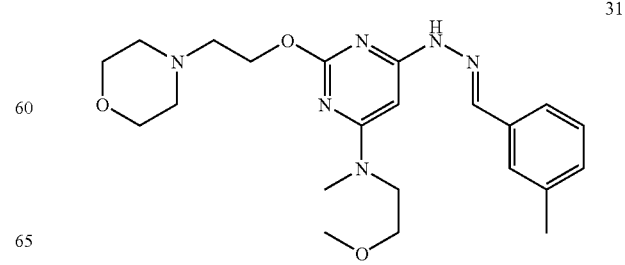

(32) 6-(2,3-Dimethyl-1H-indol-5-ylamino)-2-(2-morpholin-4-yl-ethoxy)-pyrimidine-4-carboxylic acid methyl ester

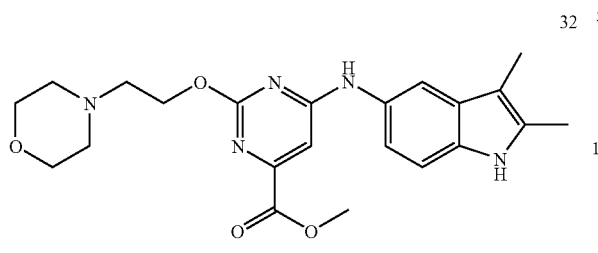

(33) 6-(2,3-Dimethyl-1H-indol-5-ylamino)-2-(2-morpholin-4-yl-ethoxy)-pyrimidine-4-carboxylic acid dimethylamide

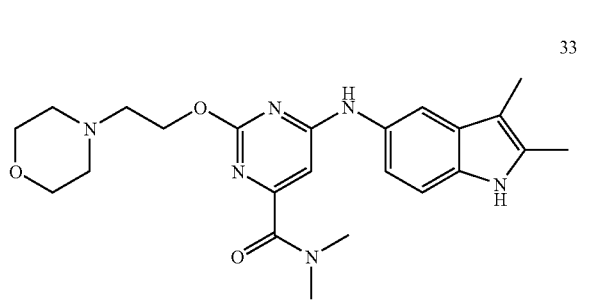

(34) [6-(2,3-Dimethyl-1H-indol-5-ylamino)-2-(2-morpholin-4-yl-ethoxy)-pyrimidin-4-yl]-morpholin-4-yl-methanone

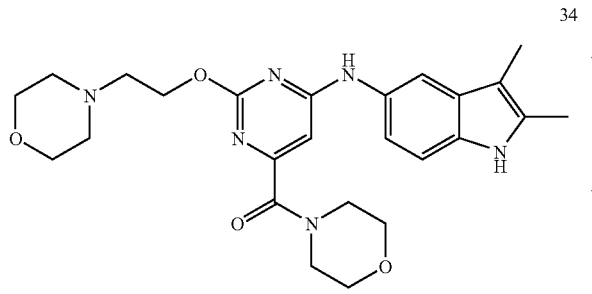

(35) 4-(2,3-Dimethyl-1H-indol-5-ylamino)-6-(2-morpholin-4-yl-ethoxy)-pyrimidine-2-carboxylic acid methyl ester

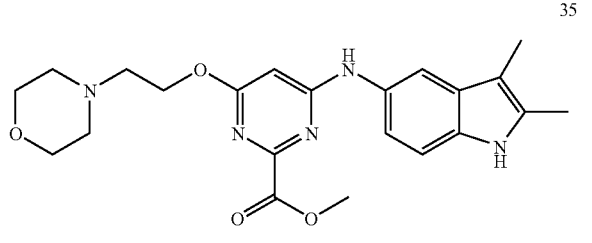

(36) N-(1H-Indol-3-ylmethylene)-N'-[2-(2-pyridin-2-yl-ethoxy)-6-thiazolidin-3-yl-pyrimidin-4-yl]-hydrazine

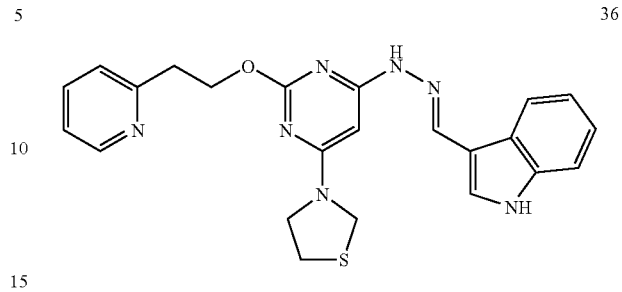

(37) N-(1H-Indol-3-ylmethylene)-N'-[2-(2-morpholin-4-yl-ethoxy)-6-thiazolidin-3-yl-pyrimidin-4-yl]-hydrazine

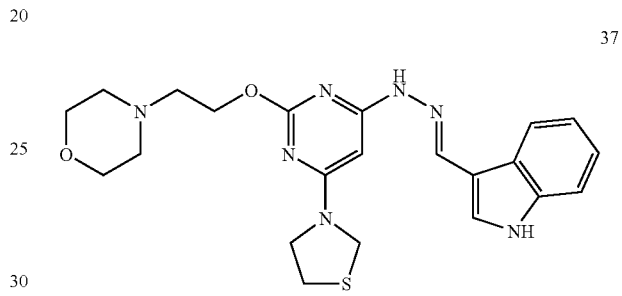

(38) N-(3-Methyl-benzylidene)-N'-[2-(2-morpholin-4-yl-ethoxy)-6-thiazolidin-3-yl-pyrimidin-4-yl]-hydrazine

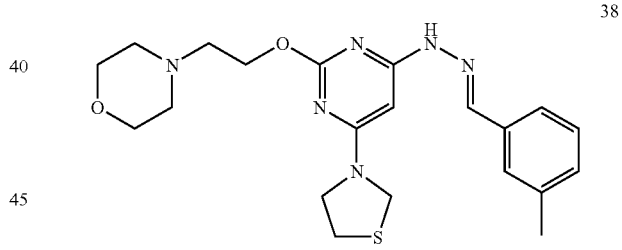

(39) 3-(2-{4-[N'-(3-Methyl-benzylidene)-hydrazino]-6-thiazolidin-3-yl-pyrimidin-2-yloxy}-ethyl)-oxazolidin-2-one

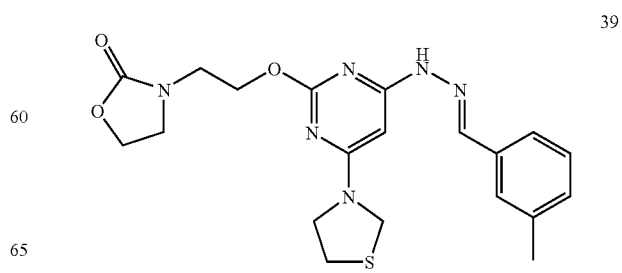

(40) 4-Methyl-2-{[2-(2-methylamino-ethoxy)-6-thiazolidin-3-yl-pyrimidin-4-yl]-hydrazonomethyl}-phenol

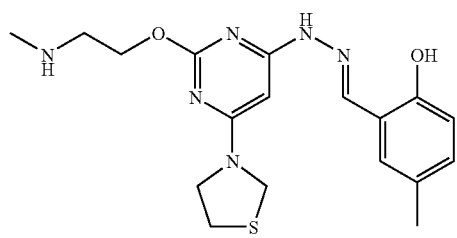

(41) N-(3-Methyl-benzylidene)-N'-[6-(2-morpholin-4-yl-ethoxy)-4-thiazolidin-3-yl-pyridin-2-yl]-hydrazine

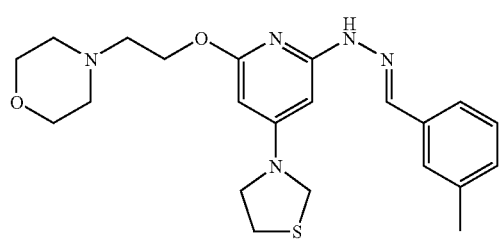

(42) N-(3-Methyl-benzylidene)-N'-[2-(2-morpholin-4-yl-ethoxy)-6-thiazolidin-3-yl-pyridin-4-yl]-hydrazine

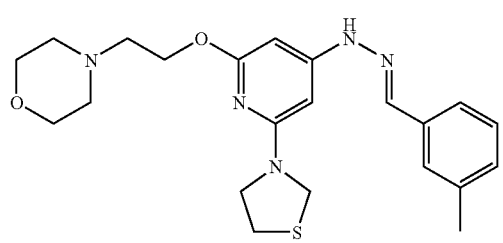

(43) (2,3-Dimethyl-1H-indol-6-yl)-[2-(2-morpholin-4-yl-ethoxy)-6-thiazolidin-3-yl-pyrimidin-4-yl]-amine

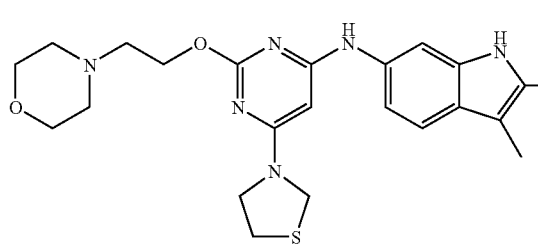

(44) 2-(2-Morpholin-4-yl-ethoxy)-6-thiazolidin-3-yl-pyrimidine-4-carboxylic acid(2,3-dimethyl-1H-indol-5-yl)-amide

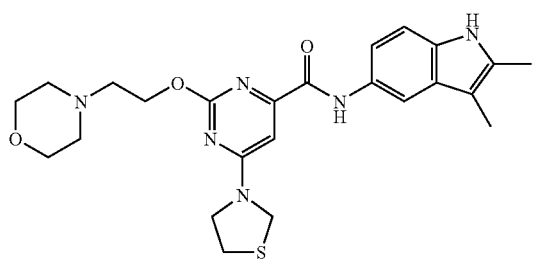

(45) 3-(2-{4-Diethylamino-6-[N'-(3-methyl-benzylidene)-hydrazino]-pyrimidin-2-yloxy}-ethyl)-oxazolidin-2-one

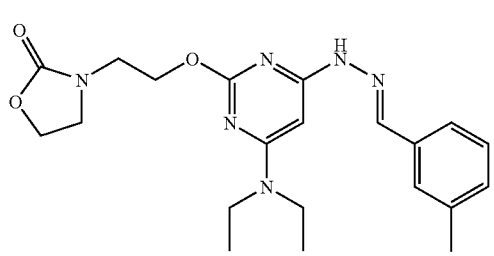

(46) Diethyl-{2-(2-methylamino-ethoxy)-6-[N'-(3-methyl-benzylidene)-hydrazino]-pyrimidin-4-yl}-amine

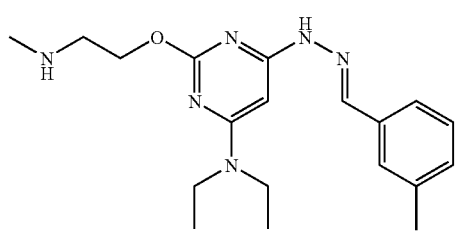

(47) 1-{4-Diethylamino-6-[N'-(3-methyl-benzylidene)-hydrazino]-pyrimidin-2-yloxy}-2-methyl-propan-2-ol

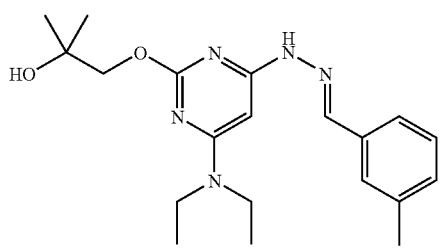

(48) Diethyl-[6-[N'-(3-methyl-benzylidene)-hydrazino]-2-(2-pyridin-2-yl-ethoxy)-pyrimidin-4-yl]-amine

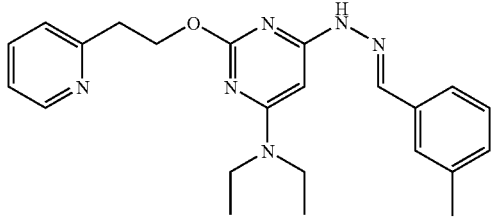

(49) 2-{[6-Diethylamino-2-(2-morpholin-4-yl-ethoxy)-pyrimidin-4-yl]-hydrazonomethyl}-4-methyl-phenol

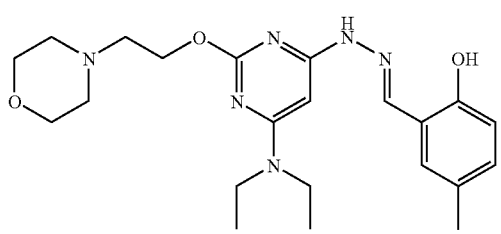

(50) Diethyl-[6-[N'-(1H-indol-3-ylmethylene)-hydrazino]-2-(2-morpholin-4-yl-ethoxy)-pyrimidin-4-yl]-amine

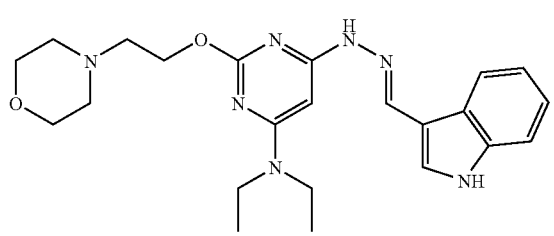

(51) Diethyl-[4-[N'-(3-methyl-benzylidene)-hydrazino]-6-(2-morpholin-4-yl-ethoxy)-[1,3,5]triazin-2-yl]-amine

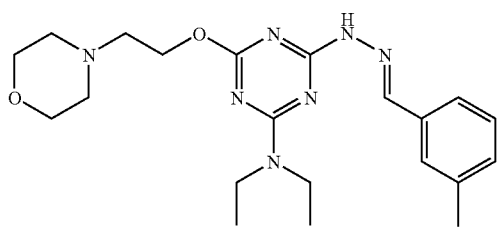

(52) Diethyl-[2-[N'-(3-methyl-benzylidene)-hydrazino]-6-(2-morpholin-4-yl-ethoxy)-pyridin-4-yl]-amine

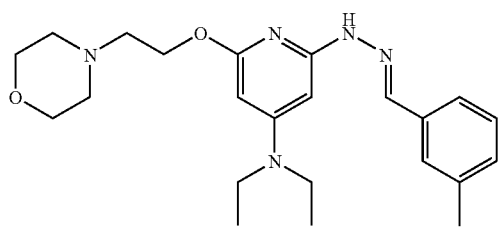

(53) Diethyl-[6-[N'-(3-methyl-benzylidene)-hydrazino]-4-(2-morpholin-4-yl-ethoxy)-pyridin-2-yl]-amine

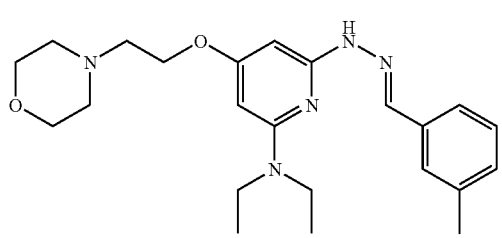

(54) 6-Diethylamino-2-(2-morpholin-4-yl-ethoxy)-pyrimidine-4-carboxylic acid(2,3-dimethyl-1H-indol-5-yl)-amide

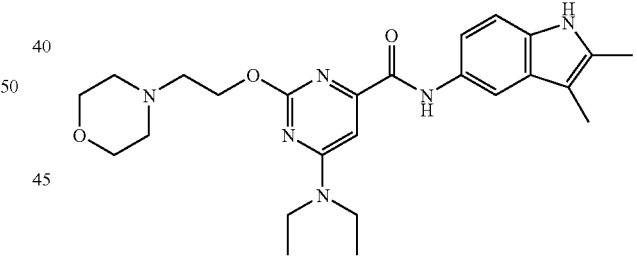

(55) 6-Diethylamino-2-(2-morpholin-4-yl-ethoxy)-4-[(2,3-dimethyl-1H-indol-5-yl)-amino]-pyrimidine

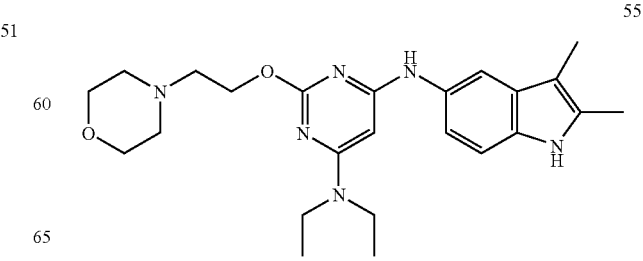

(56) 3-(2-{4-[(2-Methoxy-ethyl)-methyl-amino]-6-[N'-(3-methyl-benzylidene)-hydrazino]-pyrimidin-2-yloxy}-ethyl)-oxazolidin-2-one

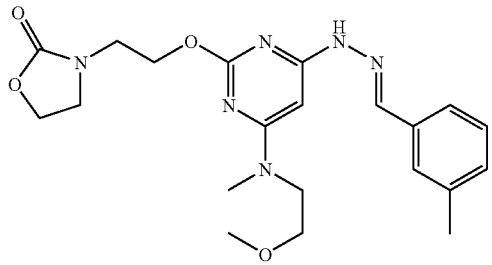

(57) (2-Methoxy-ethyl)-methyl-{2-(2-methylamino-ethoxy)-6-[N'-(3-methyl-benzylidene)-hydrazino]-pyrimidin-4-yl}-amine

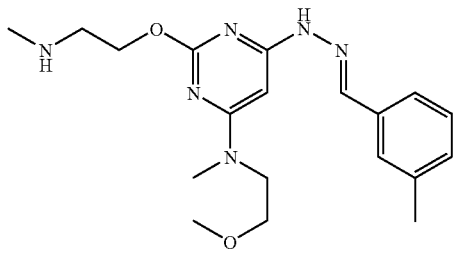

(58) 1-{4-[(2-Methoxy-ethyl)-methyl-amino]-6-[N'-(3-methyl-benzylidene)-hydrazino]-pyrimidin-2-yloxy}-2-methyl-propan-2-ol

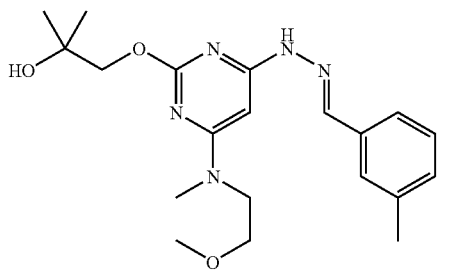

(59) (2-Methoxy-ethyl)-methyl-[4-[N'-(3-methyl-benzylidene)-hydrazino]-6-(2-morpholin-4-yl-ethoxy)-[1,3,5]triazin-2-yl]-amine

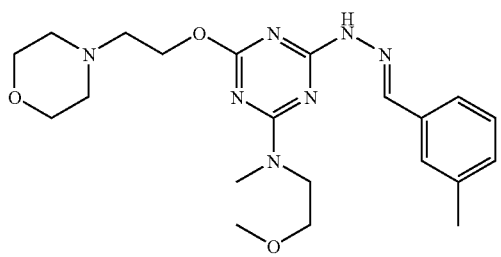

(60) (2-Methoxy-ethyl)-methyl-[2-[N'-(3-methyl-benzylidene)-hydrazino]-6-(2-morpholin-4-yl-ethoxy)-pyridin-4-yl]-amine

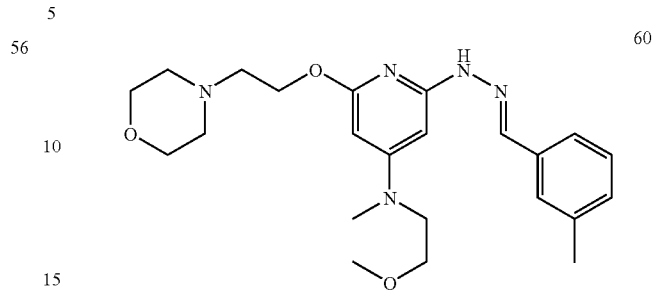

(61) (2-Methoxy-ethyl)-methyl-[6-[N'-(3-methyl-benzylidene)-hydrazino]-4-(2-morpholin-4-yl-ethoxy)-pyridin-2-yl]-amine

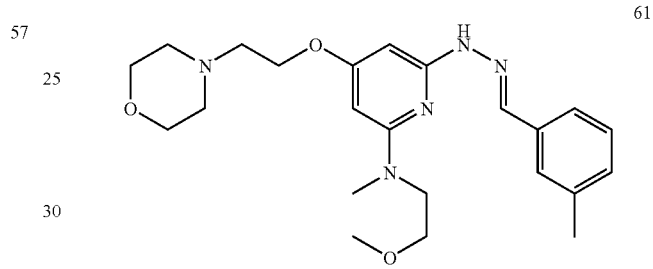

(62) 2-{[6-[(2-Methoxy-ethyl)-methyl-amino]-2-(2-morpholin-4-yl-ethoxy)-pyrimidin-4-yl]-hydrazonomethyl}-4-methyl-phenol

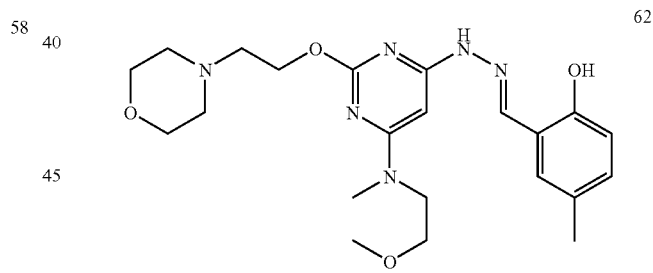

(63) [6-[N'-(1H-Indol-3-ylmethylene)-hydrazino]-2-(2-morpholin-4-yl-ethoxy)-pyrimidin-4-yl]-(2-methoxy-ethyl)-methyl-amine

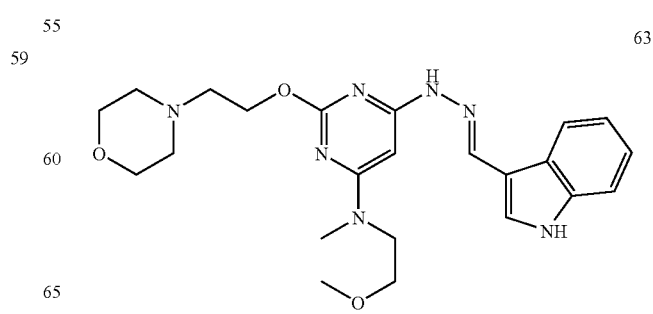

(64) 4-[(2-Methoxy-ethyl)-methyl-amino]-6-(2-morpholin-4-yl-ethoxy)-[1,3,5]triazine-2-carboxylic acid(2,3-dimethyl-1H-indol-5-yl)-amide

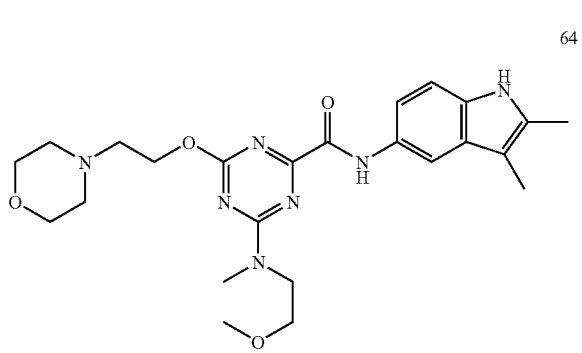

(65) N-(2,3-Dimethyl-1H-indol-5-yl)-N'-(2-methoxy-ethyl)-N'-methyl-6-(2-morpholin-4-yl-ethoxy)-[1,3,5]triazine-2,4-diamine

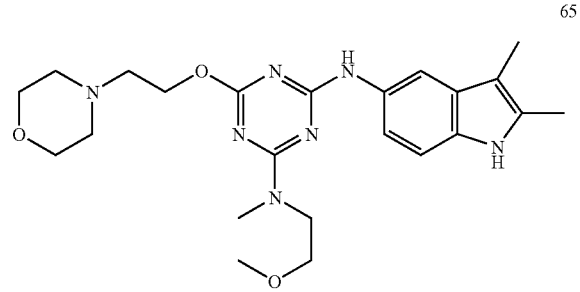

(66) Dimethyl-[6-[N'-(3-methyl-benzylidene)-hydrazino]-2-(2-morpholin-4-yl-ethoxy)-pyrimidin-4-yl]-amine

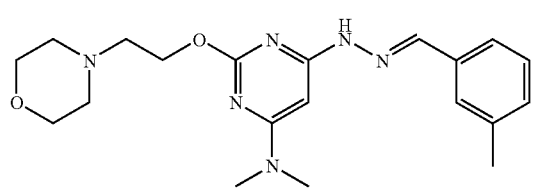

(67) 3-(2-{4-Dimethylamino-6-[N'-(3-methyl-benzylidene)-hydrazino]-pyrimidin-2-yloxy}-ethyl)-oxazolidin-2-one

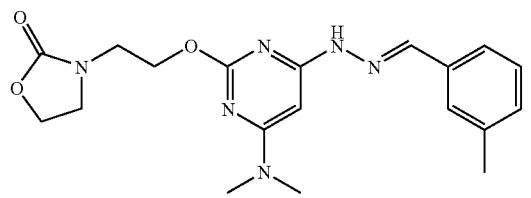

(68) Dimethyl-{2-(2-methylamino-ethoxy)-6-[N'-(3-methyl-benzylidene)-hydrazino]-pyrimidin-4-yl}-amine

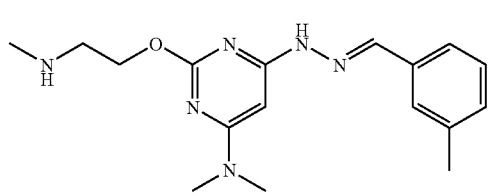

(69) 1-{4-Dimethylamino-6-[N'-(3-methyl-benzylidene)-hydrazino]-pyrimidin-2-yloxy}-2-methyl-propan-2-ol

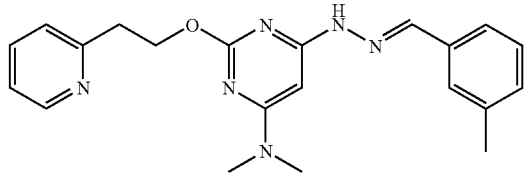

(70) Dimethyl-[6-[N'-(3-methyl-benzylidene)-hydrazino]-2-(2-pyridin-2-yl-ethoxy)-pyrimidin-4-yl]-amine

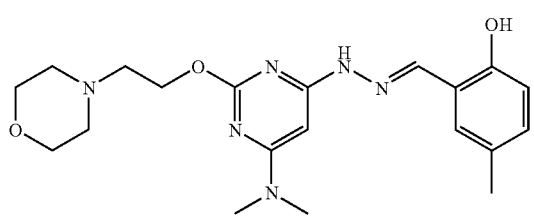

(71) 2-{[6-Dimethylamino-2-(2-morpholin-4-yl-ethoxy)-pyrimidin-4-yl]-hydrazonomethyl}-4-methyl-phenol

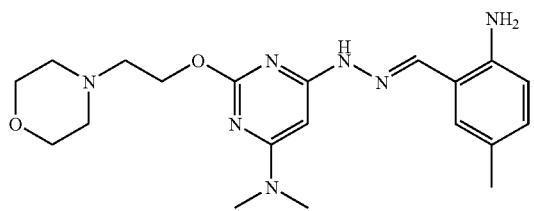

(72) [6-[N'-(2-Amino-5-methyl-benzylidene)-hydrazino]-2-(2-morpholin-4-yl-ethoxy)-pyrimidin-4-yl]-dimethyl-amine

(73) [6-[N'-(1H-Indol-3-ylmethylene)-hydrazino]-2-(2-morpholin-4-yl-ethoxy)-pyrimidin-4-yl]-dimethyl-amine

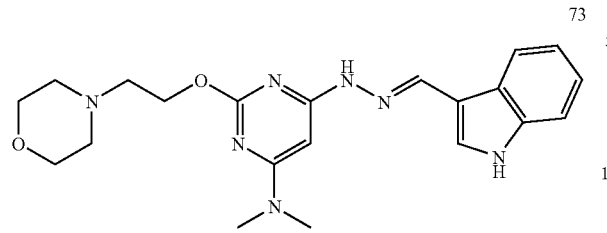

(74) Dimethyl-[4-[N'-(3-methyl-benzylidene)-hydrazino]-6-(2-morpholin-4-yl-ethoxy)-[1,3,5]triazin-2-yl]-amine

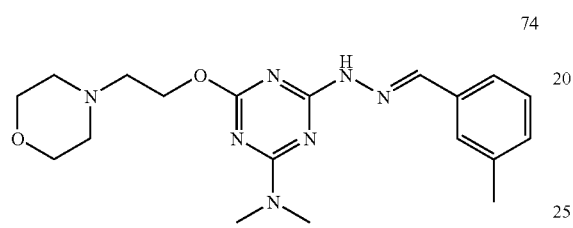

(75) Dimethyl-[6-[N'-(3-methyl-benzylidene)-hydrazino]-4-(2-morpholin-4-yl-ethoxy)-pyridin-2-yl]-amine

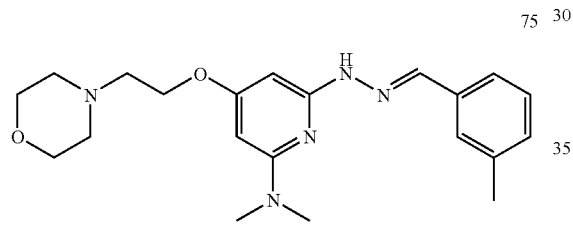

(76) 6-Dimethylamino-2-(2-morpholin-4-yl-ethoxy)-pyrimidine-4-carboxylic acid(2,3-dimethyl-1H-indol-5-yl)-amide

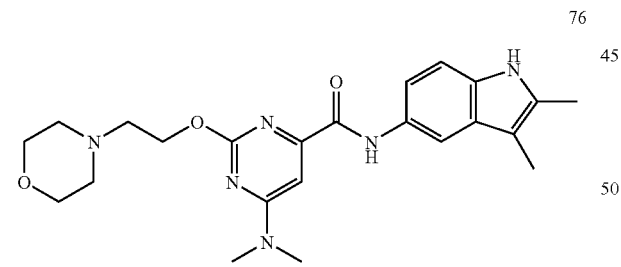

(77) 6-Dimethylamino-2-(2-morpholin-4-yl-ethoxy)-4-[(2,3-dimethyl-1H-indol-5-yl)-amino]pyrimidine

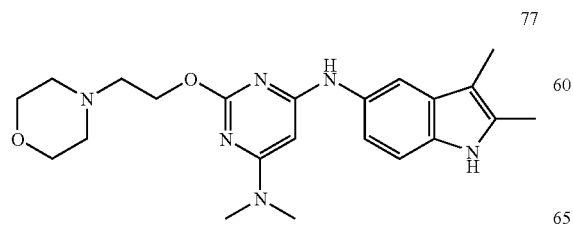

(78) 6-[N'-(3-Methyl-benzylidene)-hydrazino]-2-(2-morpholin-4-yl-ethoxy)-pyrimidin-4-ylamine

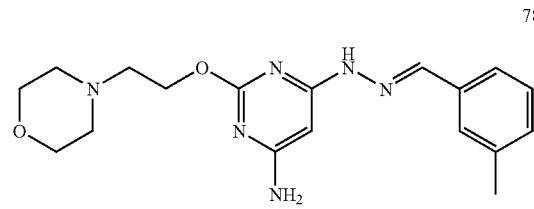

(79) 3-(2-{4-Amino-6-[N'-(3-methyl-benzylidene)-hydrazino]-pyrimidin-2-yloxy}-ethyl)-oxazolidin-2-one

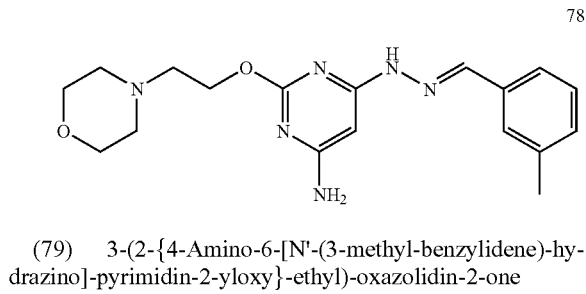

(80) 2-(2-Methylamino-ethoxy)-6-[N'-(3-methyl-benzylidene)-hydrazino]-pyrimidin-4-ylamine

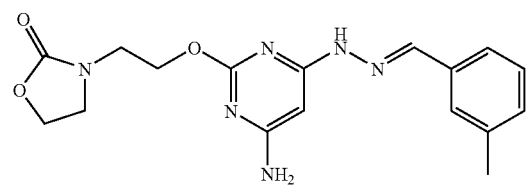

(81) 6-[N'-(3-Methyl-benzylidene)-hydrazino]-2-(2-pyridin-2-yl-ethoxy)-pyrimidin-4-ylamine

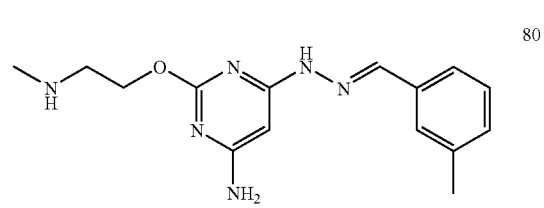

(82) 2-{[6-Amino-2-(2-morpholin-4-yl-ethoxy)-pyrimidin-4-yl]-hydrazonomethyl}-4-methyl-phenol

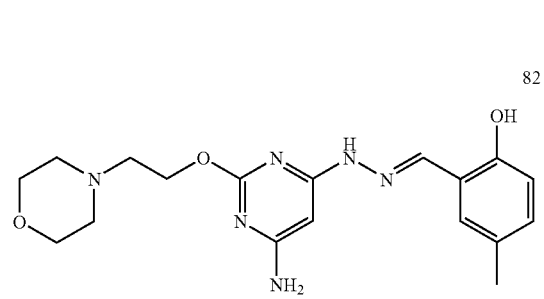

(83) 6-[N'-(2-Amino-5-methyl-benzylidene)-hydrazino]-2-(2-morpholin-4-yl-ethoxy)-pyrimidin-4-ylamine

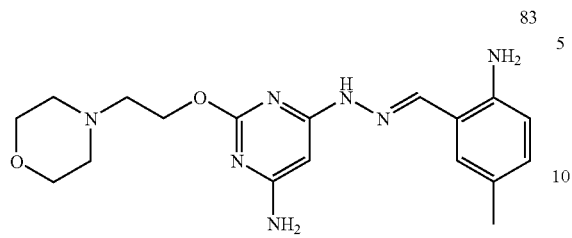

(84) 6-[N'-(1H-Indol-3-ylmethylene)-hydrazino]-2-(2-morpholin-4-yl-ethoxy)-pyrimidin-4-ylamine

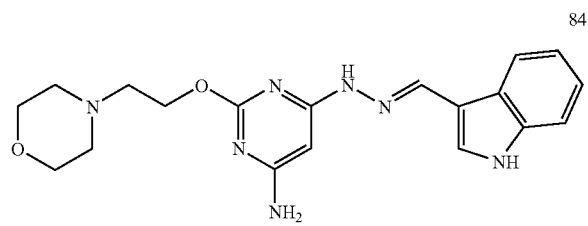

(85) 1-{4-Amino-6-[N'-(3-methyl-benzylidene)-hydrazino]-pyrimidin-2-yloxy}-2-methyl-propan-2-ol

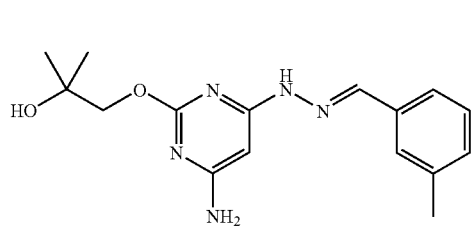

(86) 2-[N'-(3-Methyl-benzylidene)-hydrazino]-6-(2-morpholin-4-yl-ethoxy)-pyridin-4-ylamine

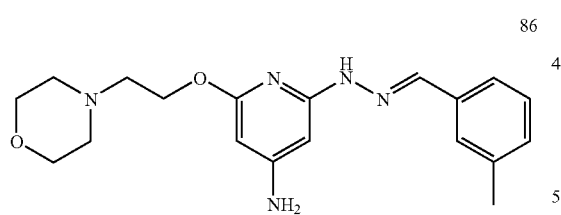

(87) 6-[N'-(3-Methyl-benzylidene)-hydrazino]-4-(2-morpholin-4-yl-ethoxy)-pyridin-2-ylamine

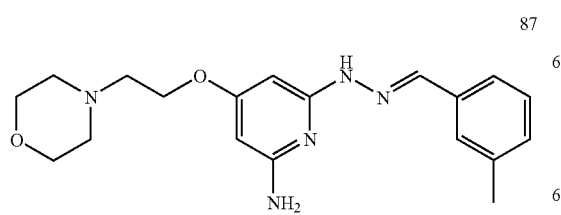

(88) 4-[N'-(3-Methyl-benzylidene)-hydrazino]-6-(2-morpholin-4-yl-ethoxy)-[1,3,5]triazin-2-ylamine

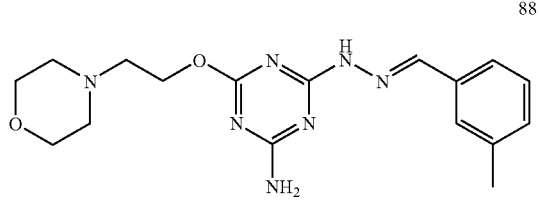

(89) 2-Amino-6-(2-morpholin-4-yl-ethoxy)-pyrimidine-4-carboxylic acid (2,3-dimethyl-1H-indol-5-yl)-amide

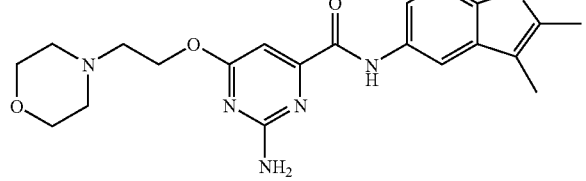

(90) N4-(2,3-Dimethyl-1H-indol-5-yl)-6-(2-morpholin-4-yl-ethoxy)-pyrimidine-2,4-diamine

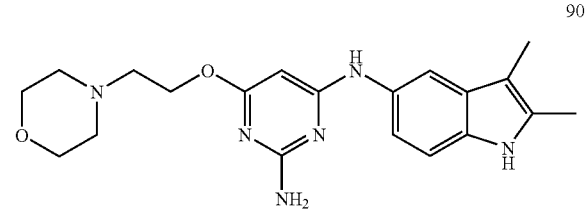

(91) N-[4-Imidazol-1-yl-6-(2-morpholin-4-yl-ethoxy)-[1,3,5]triazin-2-yl]-N'-(3-methyl-benzylidene)-hydrazine

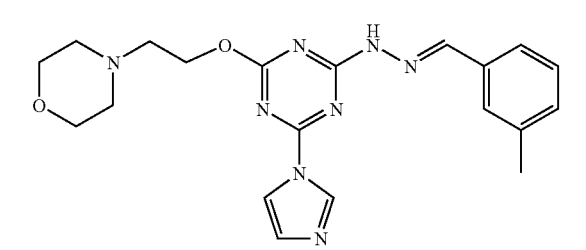

(92) 3-(2-{4-Imidazol-1-yl-6-[N'-(3-methyl-benzylidene)-hydrazino]-pyrimidin-2-yloxy}-ethyl)-oxazolidin-2-one

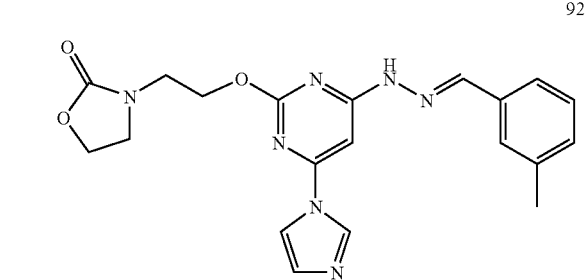

(93) (2-{4-Imidazol-1-yl-6-[N'-(3-methyl-benzylidene)-hydrazino]-pyrimidin-2-yloxy}-ethyl)-methyl-amine

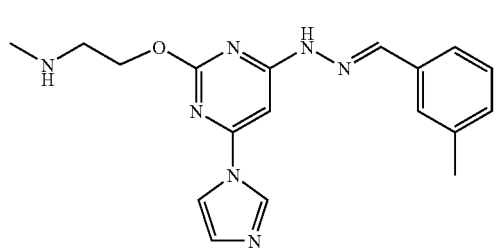

(94) 1-{4-Imidazol-1-yl-6-[N'-(3-methyl-benzylidene)-hydrazino]-pyrimidin-2-yloxy}-2-methyl-propan-2-ol

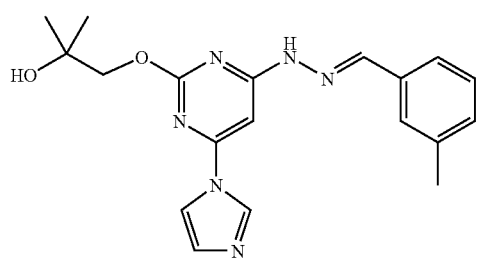

(95) N-[4-Imidazol-1-yl-6-(2-morpholin-4-yl-ethoxy)-pyridin-2-yl]-N'-(3-methyl-benzylidene)-hydrazine

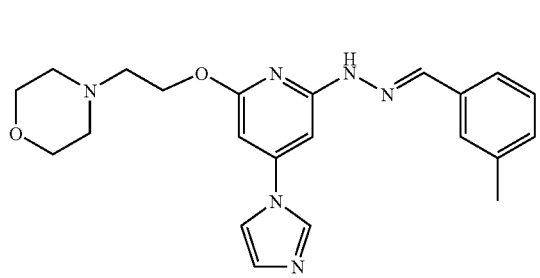

(96) 2-{[6-Imidazol-1-yl-2-(2-morpholin-4-yl-ethoxy)-pyrimidin-4-yl]-hydrazonomethyl}-4-methyl-phenol

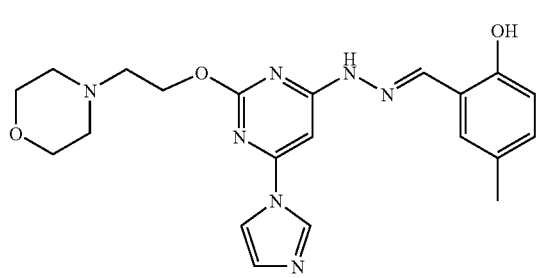

(97) N-[6-Imidazol-1-yl-2-(2-morpholin-4-yl-ethoxy)-pyrimidin-4-yl]-N'-(1H-indol-3-ylmethylene)-hydrazine

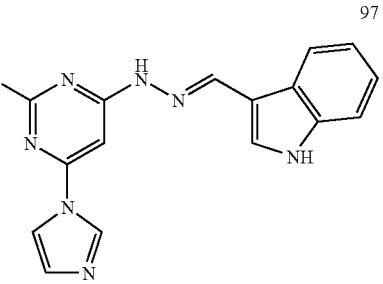

(98) 2-Imidazol-1-yl-6-(2-morpholin-4-yl-ethoxy)-pyrimidine-4-carboxylic acid(2,3-dimethyl-1H-indol-5-yl)-amide

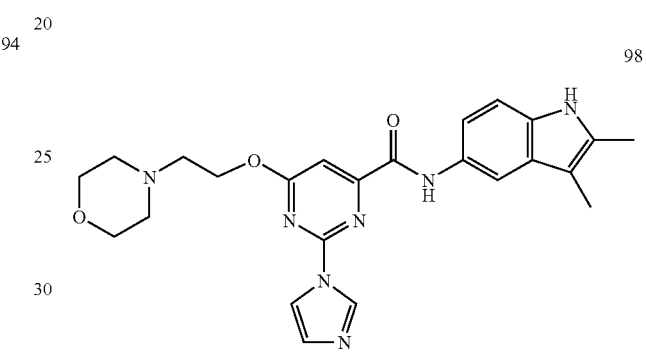

(99) (2,3-Dimethyl-1H-indol-5-yl)-[2-imidazol-1-yl-6-(2-morpholin-4-yl-ethoxy)-pyrimidin-4-yl]-amine

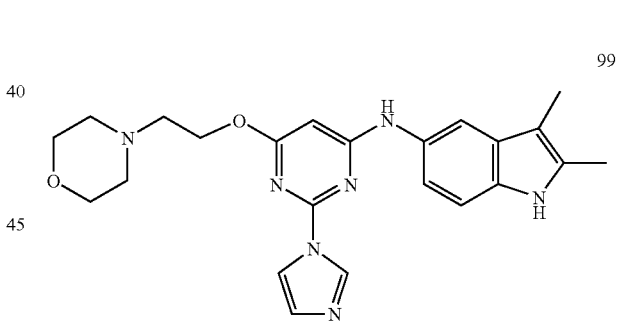

(100) 1-[2,4']Bipyridinyl-6-yl-3-indan-5-yl-urea

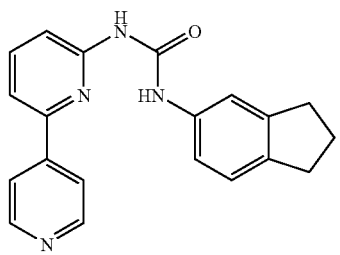

(101) 4-(2-Morpholin-4-yl-ethoxy)-[2,4']bipyridinyl-6-carboxylic acid (2,3-dimethyl-1H-indol-5-yl)-amide

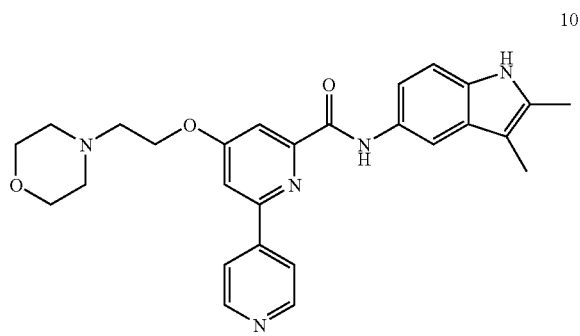

(102) 4-[(2-Methoxy-ethyl)-methyl-amino]-[2,4']bipyridinyl-6-carboxylic acid(2,3-dimethyl-1H-indol-5-yl)-amide

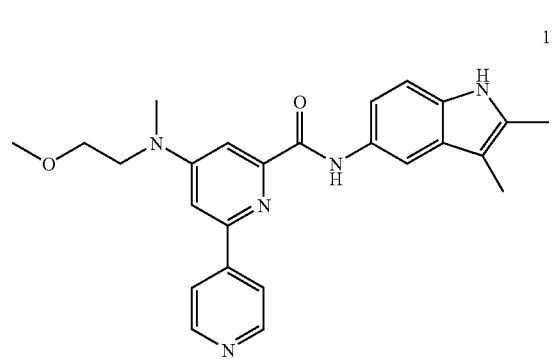

(103) 3'-Fluoro-[2,4']bipyridinyl-6-carboxylic acid(2,3-dimethyl-1H-indol-5-yl)-amide

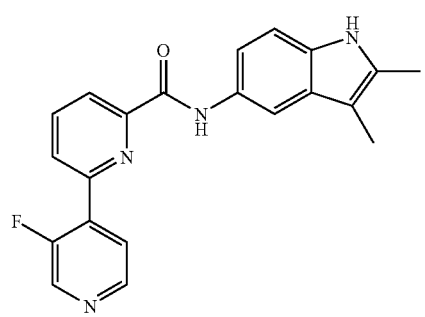

(104) 6-Pyrimidin-5-yl-pyridine-2-carboxylic acid(2,3-dimethyl-1H-indol-5-yl)-amide

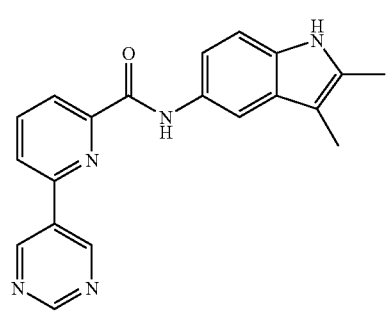

(105) 6-Thiophen-3-yl-pyridine-2-carboxylic acid(2,3-dimethyl-1H-indol-5-yl)-amide

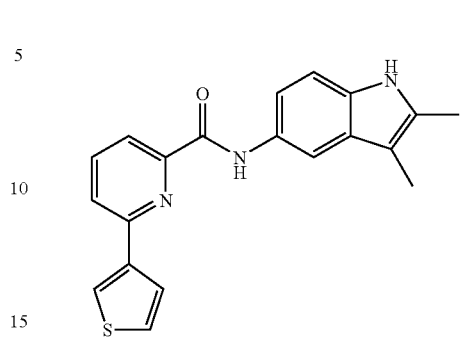

(106) [2,3']Bipyridinyl-6-carboxylic acid(2,3-dimethyl-1H-indol-5-yl)-amide

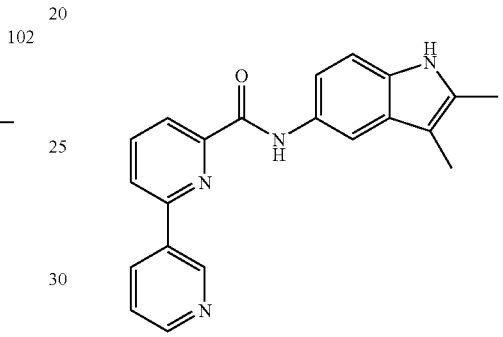

(107) 2'-Fluoro-[2,4']bipyridinyl-6-carboxylic acid(2,3-dimethyl-1H-indol-5-yl)-amide

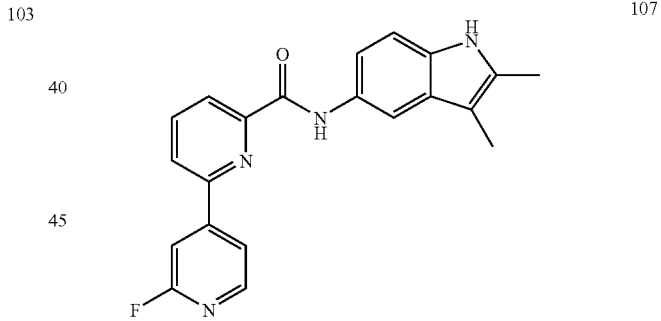

(108) 6-(1H-Pyrazol-4-yl)-pyridine-2-carboxylic acid(2,3-dimethyl-1H-indol-5-yl)-amide

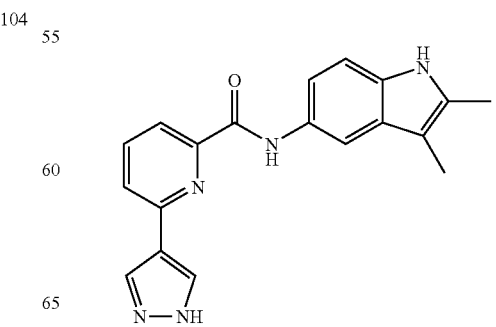

(109) (E)-4-(2-(4-(2-(3-methylbenzylidene)hydrazinyl)-6-(pyridin-4-yl)pyrimidin-2-yloxy)ethyl)morpholine

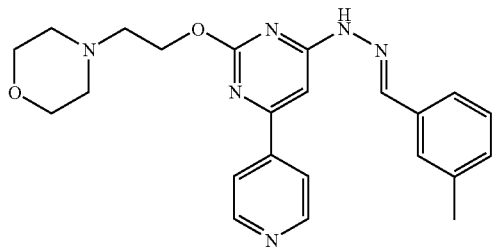

(110) (E)-4-methyl-2-((2-(2-(2-morpholinoethoxy)-6-(pyridin-4-yl)pyrimidin-4-yl)hydrazono)methyl)phenol

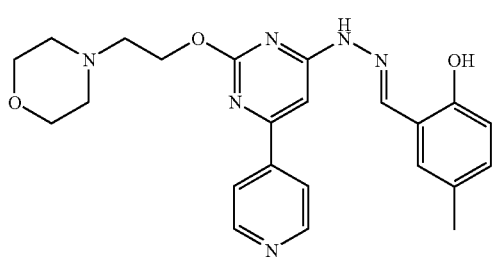

(111) (E)-4-(2-(4-(2-(3,4-dimethylbenzylidene)hydrazinyl)-6-(pyridin-4-yl)pyrimidin-2-yloxy)ethyl)morpholine

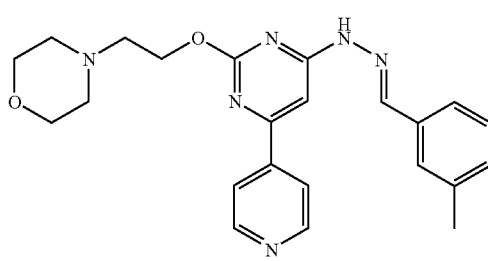

(112) (E)-4-(2-(4-(2-((4,5-dimethylthiophen-2-yl)methylene)hydrazinyl)-6-(pyridin-4-yl)pyrimidin-2-yloxy)ethyl)morpholine

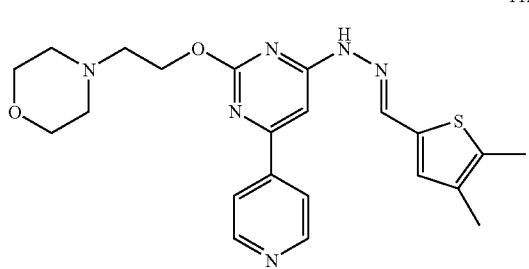

(113) (E)-N-(2-methoxyethyl)-N-methyl-4-(2-(3-methylbenzylidene)hydrazinyl)-6-(pyridin-4-yl)pyrimidin-2-amine

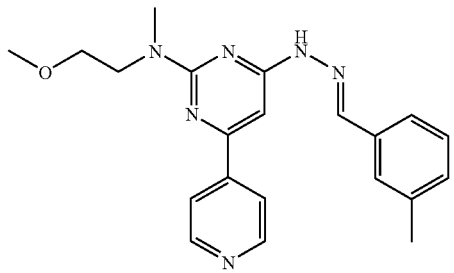

(114) (E)-2-((2-(2-((2-methoxyethyl)(methyl)amino)-6-(pyridin-4-yl)pyrimidin-4-yl)hydrazono)methyl)-4-methylphenol

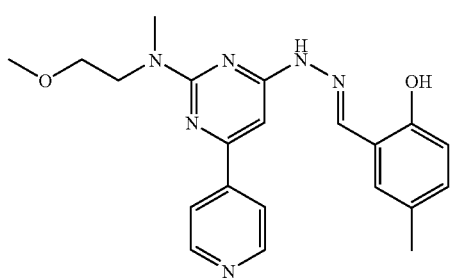

(115) (E)-4-(2-(3,4-dimethylbenzylidene)hydrazinyl)-N-(2-methoxyethyl)-N-methyl-6-(pyridin-4-yl)pyrimidin-2-amine

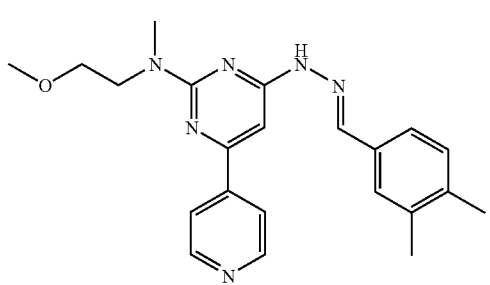

(116) (E)-4-(2-((4,5-dimethylthiophen-2-yl)methylene)hydrazinyl)-N-(2-methoxyethyl)-N-methyl-6-(pyridin-4-yl)pyrimidin-2-amine

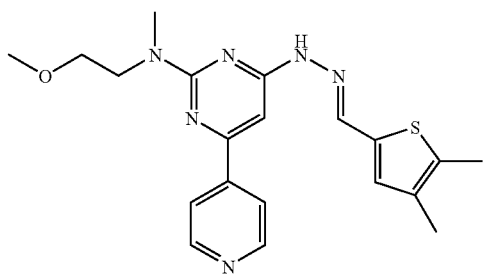

(117) (E)-2-(methyl(4-(2-(3-methylbenzylidene)hydrazinyl)-6-(pyridin-4-yl)pyrimidin-2-yl)amino)ethanol

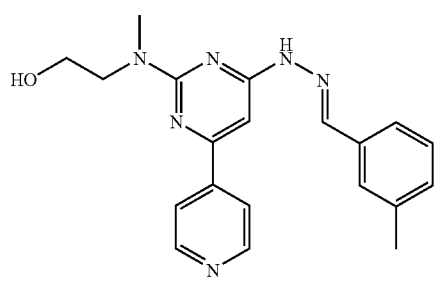

(118) (E)-2-((4-(2-(3,4-dimethylbenzylidene)hydrazinyl)-6-(pyridin-4-yl)pyrimidin-2-yl)(methyl)amino)ethanol

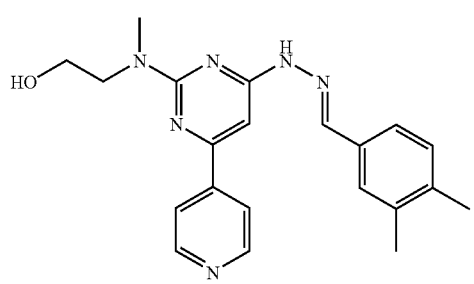

(119) (E)-2-((2-(2-((2-hydroxyethyl)(methyl)amino)-6-(pyridin-4-yl)pyrimidin-4-yl)hydrazono)methyl)-4-methylphenol

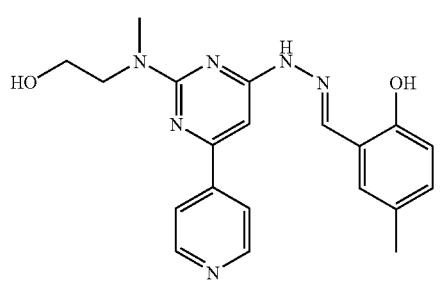

(120) (E)-2-((4-(2-((4,5-dimethylthiophen-2-yl)methylene)hydrazinyl)-6-(pyridin-4-yl)pyrimidin-2-yl)(methyl)amino)ethanol

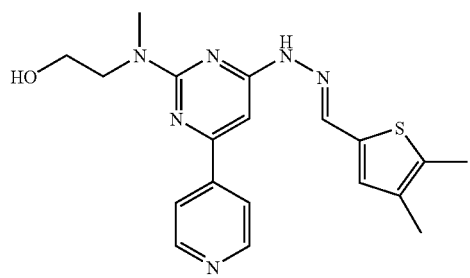

(121) (E)-O-methyl-N-(4-(2-(3-methylbenzylidene)hydrazinyl)-6-(pyridin-4-yl)pyrimidin-2-yl)hydroxylamine

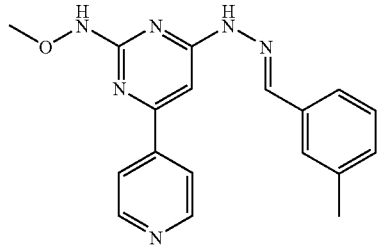

(122) (E)-N-(4-(2-(3,4-dimethylbenzylidene)hydrazinyl)-6-(pyridin-4-yl)pyrimidin-2-yl)-O-methylhydroxylamine

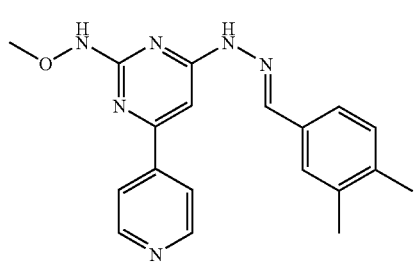

(123) (E)-2-((2-(2-(methoxyamino)-6-(pyridin-4-yl)pyrimidin-4-yl)hydrazono)methyl)-4-methylphenol

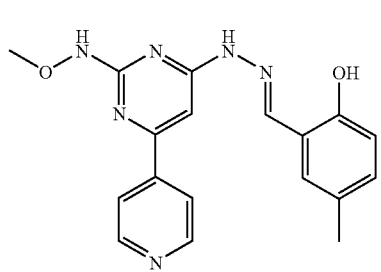

(124) (E)-N-(4-(2-((4,5-dimethylthiophen-2-yl)methylene)hydrazinyl)-6-(pyridin-4-yl)pyrimidin-2-yl)-O-methylhydroxylamine

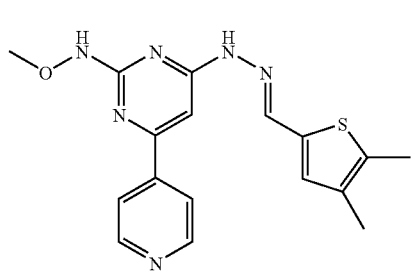

(125) (E)-4-(2-(3-methylbenzylidene)hydrazinyl)-2-(2-(pyridin-2-yl)ethoxy)-6-(pyridin-4-yl)pyrimidine

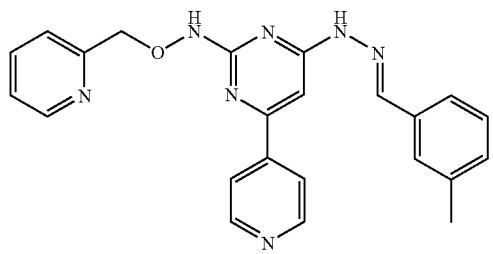

(126) (E)-4-(2-(3,4-dimethylbenzylidene)hydrazinyl)-2-(2-(pyridin-2-yl)ethoxy)-6-(pyridin-4-yl)pyrimidine

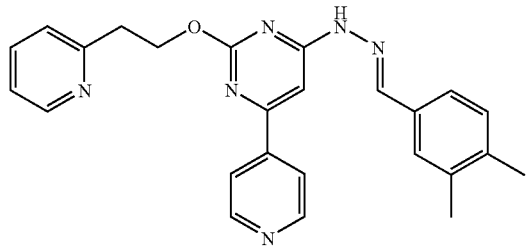

(127) (E)-4-methyl-2-((2-(2-(2-(pyridin-2-yl)ethoxy)-6-(pyridin-4-yl)pyrimidin-4-yl)hydrazono)methyl)phenol

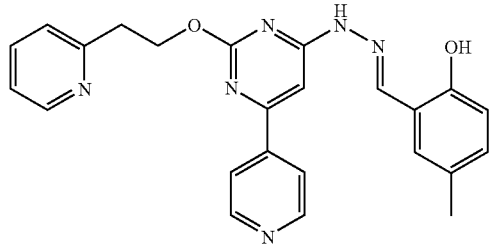

(128) (E)-4-(2-((4,5-dimethylthiophen-2-yl)methylene)hydrazinyl)-2-(2-(pyridin-2-yl)ethoxy)-6-(pyridin-4-yl)pyrimidine

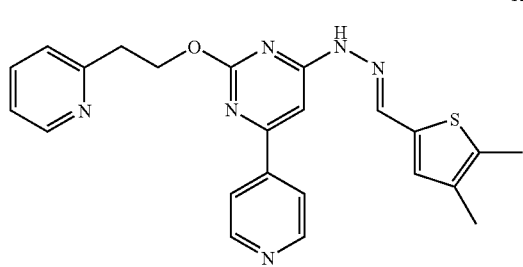

(129) (E)-4-(2-(4-(2-(3-methylbenzylidene)hydrazinyl)-6-(pyridin-4-yl)-1,3,5-triazin-2-yloxy)ethyl)morpholine

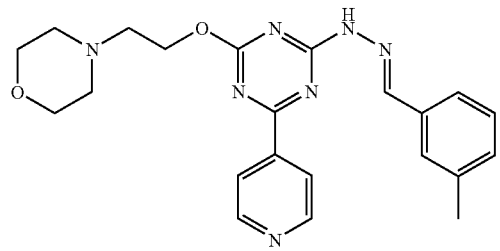

(130) (E)-4-(2-(4-(2-((4,5-dimethylthiophen-2-yl)methylene)hydrazinyl)-6-(pyridin-4-yl)-1,3,5-triazin-2-yloxy)ethyl)morpholine

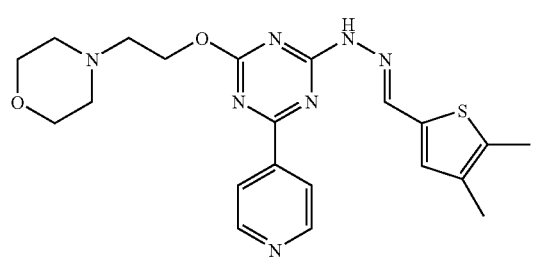

(131) (E)-N-(2-methoxyethyl)-N-methyl-4-(2-(3-methylbenzylidene)hydrazinyl)-6-(pyridin-4-yl)-1,3,5-triazin-2-amine

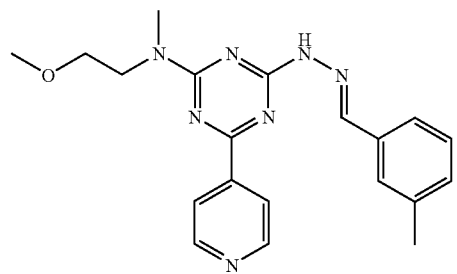

(132) (E)-4-(2-((4,5-dimethylthiophen-2-yl)methylene)hydrazinyl)-N-(2-methoxyethyl)-N-methyl-6-(pyridin-4-yl)-1,3,5-triazin-2-amine

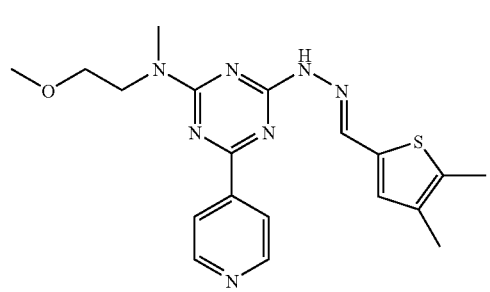

(133) (E)-O-methyl-N-(4-(2-(3-methylbenzylidene)hydrazinyl)-6-(pyridin-4-yl)-1,3,5-triazin-2-yl)hydroxylamine

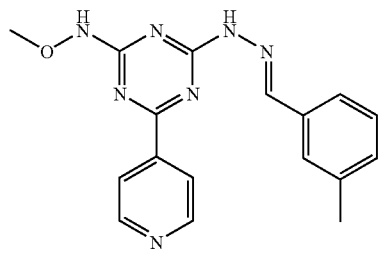

(134) (E)-N-(4-(2-((4,5-dimethylthiophen-2-yl)methylene)hydrazinyl)-6-(pyridin-4-yl)-1,3,5-triazin-2-yl)-O-methylhydroxylamine

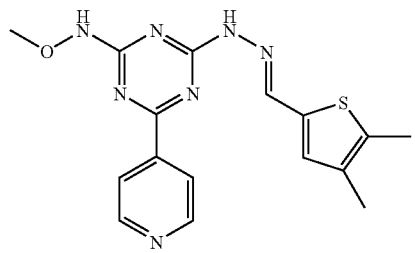

(135) (E)-4-(2-(6-(2-(3-methylbenzylidene)hydrazinyl)-4,4'-bipyridin-2-yloxy)ethyl)morpholine

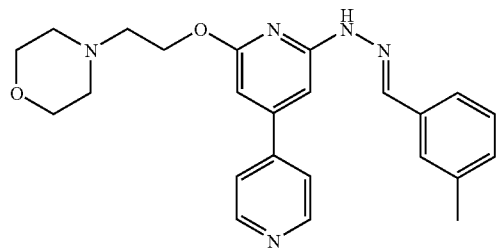

(136) (E)-4-(2-(6-(2-((4,5-dimethylthiophen-2-yl)methylene)hydrazinyl)-4,4'-bipyridin-2-yloxy)ethyl)morpholine

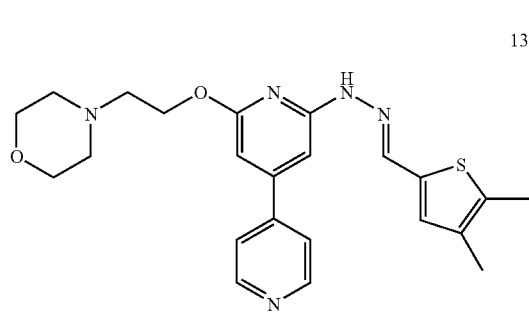

(137) (E)-2-(methyl(6-(2-(3-methylbenzylidene)hydrazinyl)-4,4'-bipyridin-2-yl)amino)ethanol

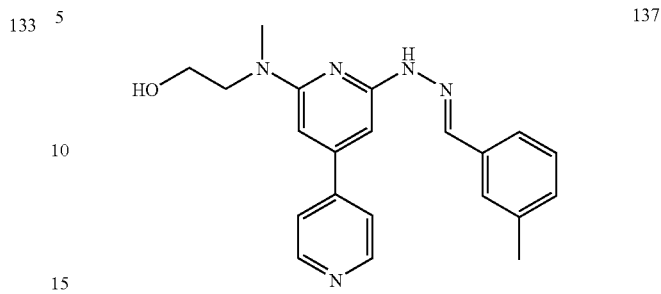

(138) (E)-2-((6-(2-(3,4-dimethylbenzylidene)hydrazinyl)-4,4'-bipyridin-2-yl)(methyl)amino)ethanol

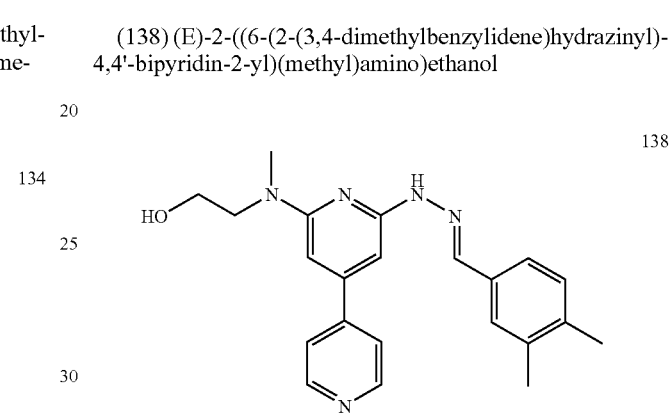

(139) (E)-6-(2-((4,5-dimethylthiophen-2-yl)methylene)hydrazinyl)-N-(2-methoxyethyl)-N-methyl-4,4'-bipyridin-2-amine

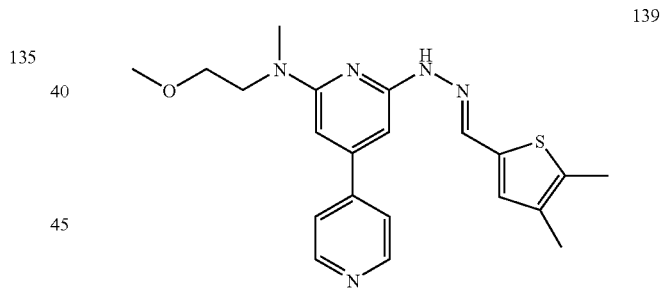

(140) (E)-6-(2-((4,5-dimethylthiophen-2-yl)methylene)hydrazinyl)-N-(2-methoxyethyl)-N-methyl-4,4'-bipyridin-2-amine

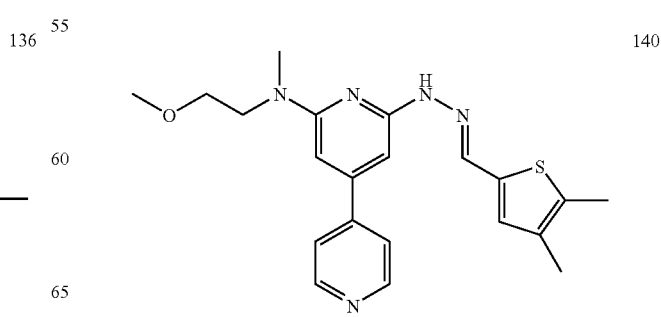

(141) (E)-4-(2-(6-(2-(3-methylbenzylidene)hydrazinyl)-2-(pyridin-4-yl)pyrimidin-4-yloxy)ethyl)morpholine

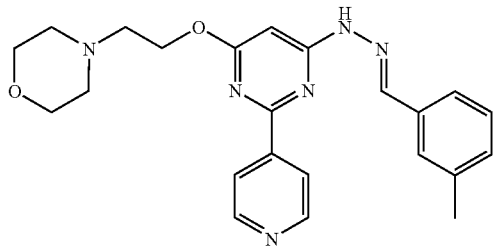

(142) (E)-4-(methoxymethyl)-6-(2-(3-methylbenzylidene)hydrazinyl)-2-(pyridin-4-yl)pyrimidine

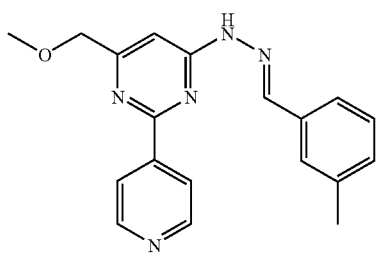

(143) (E)-4-(2-(3-methylbenzylidene)hydrazinyl)-6-(pyridin-3-yl)-1,3,5-triazin-2-amine

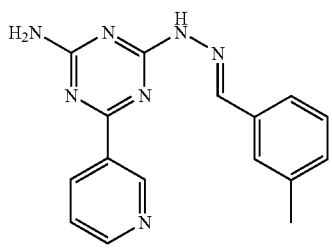

(144) 1-(4-(methylthio)-6-(pyridin-4-yl)-1,3,5-triazin-2-yl)-3-m-tolylurea

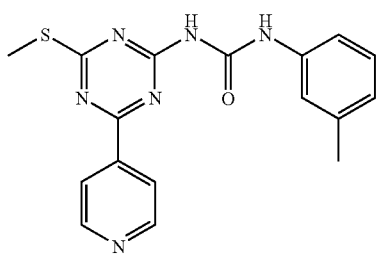

(145) 1-(4-(methylthio)-6-(pyridin-3-yl)-1,3,5-triazin-2-yl)-3-m-tolylurea

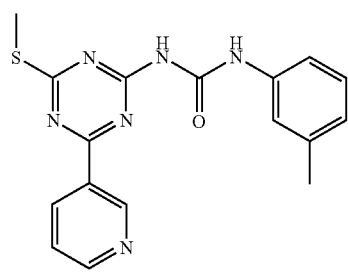

(146) N-(2,3-dimethyl-1H-indol-5-yl)-2,4'-bipyridine-6-carboxamide (147) N-(2,3-dimethyl-1H-indol-5-yl)-2-(dimethylamino)-6-(2-morpholino ethylamino)pyrimidine-4-carboxamide (148) N-(2,3-dimethyl-1H-indol-5-yl)-6-(2-morpholinoethylamino)-2-(thiazolidin-3-yl)pyrimidine-4-carboxamide In one aspect, the invention comprises a pharmaceutical composition comprising a compound of any of the formulae herein or pharmaceutically acceptable salt, solvate, clathrate, hydrate, polymorph, or prodrug thereof, and a pharmaceutically acceptable carrier.

The compounds of the invention are particularly useful in inhibiting the production of IL-12 and/or inhibiting the production of cytokines such as IL-23 and IL-27 which stimulate and/or otherwise augment the production of IL-12 and/or the proliferation of $T_H1$ lymphocytes. Thus, in one aspect, the present invention provides a method of inhibiting the production of IL-12 and/or inhibiting the production of a cytokine that stimulates or augments the production of IL-12 (e.g., IL-23 and IL-27) in a subject by administering to the subject an effective amount of a compound of formula (I), or a pharmaceutically acceptable salt, solvate, clathrate, hydrate, polymorph, or prodrug thereof.

Since one of the function of IL-12 is induction of INF-γ expression from T and NK cells which promotes the development of $T_H1$ T lymphocyte type, the compounds of the invention can be used to inhibit the production of $T_H1$ cells. Therefore, in another aspect, the invention features a method of inhibiting the proliferation and/or development/proliferation of $T_H1$ lymphocytes in a subject by administering to the subject an effective amount of a compound of formula (I), or a pharmaceutically acceptable salt, solvate, clathrate, hydrate, polymorph, or prodrug thereof.

In another aspect, the invention provides a method of treating an IL-12 overproduction-related disorder, comprising administering to a subject in need thereof a therapeutically effective amount of a compound of formula (I), formula (II), formula (III), or a pharmaceutically acceptable salt, solvate, clathrate, hydrate, polymorph, or prodrug thereof. IL-12 overproduction disorders include, but are not limited to multiple sclerosis, sepsis, myasthenia gravis, autoimmune neuropathies, Guillain-Barré syndrome, autoimmune uveitis, autoimmune hemolytic anemia, pernicious anemia, autoimmune thrombocytopenia, temporal arteritis, anti-phospholipid syndrome, vasculitides, Wegener's granulomatosis, Behcet's disease, psoriasis, psoriatic arthritis, dermatitis herpetiformis, pemphigus vulgaris, vitiligo, Crohn's disease, ulcerative colitis, interstitial pulmonary fibrosis, myelofibrosis, hepatic fibrosis, myocarditis, thyroditis, primary biliary cirrhosis, autoimmune hepatitis, Type 1 or immune-mediated diabetes mellitus, Grave's disease, Hashimoto's thyroiditis, autoimmune oophoritis and orchitis, autoimmune disease of the adrenal gland; rheumatoid arthritis, juvenile rheumatoid arthritis, systemic lupus erythematosus, scleroderma, common variable immunodeficiency (CVID), polymyositis, dermatomyositis, spondyloarthropathies, ankylosing spondylitis, Sjogren's syndrome and graft-versus-host disease. In a further embodiment, the disorders treated by the invention include rheumatoid arthritis, sepsis, Crohn's disease, multiple sclerosis, psoriasis, psoriatic arthritis, or immune-mediated diabetes mellitus.

Although the mechanism is not yet understood, compounds of the invention have been found to inhibit the formation of osteoclasts (see co-owned PCT Application Number US04/17064, filed on May 28, 2004, the entire teachings of which are incorporated herein by reference). Osteoclasts are unique multinucleated cells within bone that are responsible for bone degradation and resorption. These are the only cells in the body known to be capable of this function. The regulation of osteoclastic formation and activity is only partly understood but it is known that excessive bone resorption by osteoclasts contributes to the pathology of many human diseases associated with excessive bone loss. Thus, in one aspect, the invention provides a method of treating or preventing disorders associated with excessive bone loss, comprising administering to a subject in need thereof a therapeutically effective amount of a compound of formula (I) or pharmaceutically acceptable salt, solvate, clathrate, hydrate, polymorph, or prodrug thereof. Disorders associated with excessive bone loss include, but are not limited to periodontal disease, non-malignant bone disorders, osteoporosis, Paget's disease of bone, osteogenesis imperfecta, fibrous dysplasia, and primary hyperparathyroidism, estrogen deficiency, inflammatory bone loss, bone malignancy, arthritis, osteopetrosis, hypercalcemia of malignancy (HCM), osteolytic bone lesions of multiple myeloma and osteolytic bone metastases of breast cancer, and metastatic cancers.

In another aspect, the invention provides a method for inhibiting osteoclast formation in vitro or in vivo, comprising contacting a pre-osteoclast cell with an effective amount of a compound of formula (I) or pharmaceutically acceptable salt, solvate, clathrate, hydrate, polymorph, or prodrug thereof.

In another aspect, the invention provides a method of treating or preventing a disorder associated with excessive bone resorption by osteoclasts in a subject in need thereof, comprising administering to the subject an effective amount of a compound of formula (I) or pharmaceutically acceptable salt, solvate, clathrate, hydrate, polymorph, or prodrug thereof.

The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Other embodiments include the compounds, intermediates, or a pharmaceutically acceptable salt, solvate, clatharate, hydrate, polymorph, or prodrug thereof delineated herein, or compositions including them; as well as their methods of use for treatment or prevention of disease, inhibition of IL-12, or modulation of IL-12 mediated disease.

Another embodiment is a method of making a compound of any of the formulae herein using any one, or combination of, reactions delineated herein. The method can include the use of one or more intermediates or chemical reagents delineated herein.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{35}S$, $^{32}P$, $^{125}I$, and $^{131}I$) introduced into the compound. Such compounds are useful for drug metabolism studies and diagnostics, as well as therapeutic applications.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The sp² or sp carbons of an alkenyl group and an alkynyl group, respectively, may optionally be the point of attachment of the alkenyl or alkynyl groups.

The term "alkoxy" refers to an —O-alkyl radical. The term "ester" refers to a —C(O)O—$R^k$ or, where a divalent group is indicated, an "ester" group is —C(O)O— or —OC(O)—. An "amido" is an —C(O)NH$_2$, and an "N-alkyl-substituted amido" is of the formula C(O)NHR$^k$; where a divalent "amide" group is indicated, the group is —C(O)N$^k$— or —N$^k$C(O)—.

The term "mercapto" refers to a —SH group.

As used herein, the term "halogen" or "halo" means —F, —Cl, —Br or —I.

As used herein, the term "haloalkyl" means an alkyl group in which one or more (including all) of the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system having at least one saturated ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cyclyl" refers to a hydrocarbon 3-8 membered monocyclic or 7-14 membered bicyclic ring system having at least one non-aromatic ring, wherein the non-aromatic ring has some degree of unsaturation. Cyclyl groups may be optionally substituted with one or more substituents. In one embodiment, 0, 1, 2, 3, or 4 atoms of each ring of a cyclyl group may be substituted by a substituent. Examples of cyclyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl,cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a ($C_1$-$C_6$)alkylene group. Aralkyl groups may be optionally substituted, either on the aryl portion of the aralkyl group or on the alkylene portion of the aralkyl group, with one or more substituents. Representative aralkyl groups include benzyl, 2-phenyl-ethyl, naphth-3-yl-methyl and the like.

As used herein, the term "alkylene" refers to an alkyl group that has two points of attachment. The term "($C_1$-$C_6$)alkylene" refers to an alkylene group that has from one to six carbon atoms. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH(CH$_3$)—), and the like.

The term "arylalkoxy" refers to an alkoxy substituted with aryl.

The term "heteroaryl" refers to a 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a ($C_1$-$C_6$)alkylene. Heteroaralkyl groups may be optionally substituted, either on the heteroaryl portion of the heteroaralkyl group or on the alkylene portion of the heteroaralkyl group, with one or more substituent. Representative heteroaralkyl groupss include 2-(pyridin-4-yl)-propyl, 2-(thien-3-yl)-ethyl, imidazol-4-yl-methyl and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P and Si, preferably O, N, and S, wherein the nonaromatic ring system is completely saturated. Bicyclic and tricyclic ring systems may be fused ring systems or spiro ring systems. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, 1,4-dioxa-8-aza-spiro[4.5]dec-8-yl, tetrahydrofuranyl, tetrahydrothienyl, thiirene.

The term "heterocyclyl" refers to a nonaromatic 5-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocyclyl groups may be optionally substituted with one or more substituents. In one embodiment, 0, 1, 2, 3, or 4 atoms of each ring of a heterocyclyl group may be substituted by a substituent. Examples of these groups include thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin,1,4-dioxin, 1,4-dithiin, 1H-pyranyl, oxathiepinyl, 5H-1,4-dioxepinyl, 5H-1,4-dithiepinyl, 6H-isoxazolo[2,3-d] 1,2,4-oxadiazolyl, 7aH-oxazolo[3,2-d]1,2,4-oxadiazolyl, and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" or "hydroxylalkyl" refers to an alkyl substituent which is further substituted with one or more hydroxyl groups. The term "sulfonylalkyl" refers to an alkyl substituent which is further substituted with one or more sulfonyl groups. The term "sulfonylaryl" refers to an aryl substituent which is further substituted with one or more sulfonyl groups. The term "alkylcarbonyl" refers to an —C(O)-alkyl. The term "mercaptoalkoxy" refers to an alkoxy substituent which is further substituted with one or more mercapto groups. The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, cyclyl, heterocycloalkyl, or heterocyclyl group) is replaced with any desired group that do not substantially adversely affect the stability of the compound. In one embodiment, desired substituents are those which do not adversely affect the activity of a compound. A substituent that substantially affects the activity of a compound is one that causes the IC$_{50}$ of the compound to be greater than 100 µM. In preferred embodiments, a compound of the invention has an IC$_{50}$ in an assay indicative of activity useful for treatment of IL-12-related dieases or conditions. Such assays are known to one of ordinary skill in the art, and include, e.g., the assays described herein, e.g., the assays of Examples 2-4. In preferred embodiments, the assay is the assay of Example 2 and the compound has an IC$_{50}$ less than 1.0 mM, more preferably less than 100 uM, more preferably less than 10 uM, more preferably less than 1 uM, more preferably less than 100 nM, and more preferably less than 10 nM. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, alkylarylamino, cyano, nitro, mercapto, thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cyclyl, heterocyclyl, wherein alkyl, alkenyl, alkyloxy, alkoxyalkyl, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), imino (=NR), C(=N—NR$^k$)R$^k$, or C(=N—OR$^k$)R$^k$.

In other embodiments, substituents on any group (such as, for example, alkyl, alkenyl, alkynyl, aryl, aralkyl, heteroaryl, heteroaralkyl, cycloalkyl, cyclyl, heterocycloalkyl, and heterocyclyl) can be at any atom of that group, wherein any group that can be substituted (such as, for example, alkyl, alkenyl, alkynyl, aryl, aralkyl, heteroaryl, heteroaralkyl, cycloalkyl, cyclyl, heterocycloalkyl, and heterocyclyl) can be optionally substituted with one or more substituents (which may be the same or different), each replacing a hydrogen atom. Examples of suitable substituents include, but not limited to alkyl, alkenyl, alkynyl, cyclyl, cycloalkyl, heterocyclyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents for an alkyl, alkenyl, alkynyl, aryl, aralkyl, heteroaryl, heteroaralkyl, cycloalkyl, cyclyl, heterocycloalkyl, and heterocyclyl include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, (=O), (=S), (=NR$^{15}$), C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocyclyl, or heteroaryl. Each R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, $C_1$-$C_4$ alkyl, OH, $C_1$-$C_4$ alkoxy, COOH, C(O)O$C_1$-$C_4$ alkyl, $NH_2$, $C_1$-$C_4$ alkylamino, or $C_1$-$C_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

Note that unless otherwise depicted, the left atom shown in any substituted group which has one point of attachment described above is the point of attachment.

In the compounds represented by formula (I), when n is 2 or greater, a compound of the invention may have two or more different $C(R^2R^4)$ moieties. When there is more than one group having a designation (e.g., $R^c$-, or $R^d$-containing substituted groups) in a compound of the invention, the moieties (e.g., $R^c$, $R^d$) can be the same or different. The same rules apply to other R-groups (e.g., R, $R^g$, $R^h$, $R^j$, $R^k$, etc).

The recitation of a listing of chemical groups in any definition of a variable herein includes definitions of that variable as any single group or combination of listed groups.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating IL-12 overproduction-related disorders such as rheumatoid arthritis, sepsis, Crohn's disease, multiple sclerosis, psoriasis, or insulin-dependent diabetes mellitus). The compounds produced by the methods herein can be incorporated into compositions, including solutions, capsules, cremes, or ointments for administration to a subject (e.g., human, animal). Such compositions (e.g., pharmaceuticals) are useful for providing to the subject desirable health or other physiological benefits that are associated with such compounds.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

The compounds of this invention include the compounds themselves, as well as their salts, solvate, clathrate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Further, the aforementioned compounds of the invention also include their N-oxides. The term "N-oxides" refers to one or more nitrogen atoms, when present in a compound of the invention, are in N-oxide form, i.e., N→O. In particular, in compounds of formula (I), when one of Q, U, or V is N, also included are compounds in which Q, U, or V, respectively, is N→O.

The compounds and compositions described herein are useful to treat and prevent any IL-12 production-related disorders, e.g., inflammatory disorders, immune diseases, and bone loss diseases.

Also within the scope of this invention is a pharmaceutical composition that contains one or more of the compounds of this invention and a pharmaceutically acceptable carrier.

The compounds and compositions described herein are useful to treat and prevent any IL-12 production-related disorders, e.g., inflammatory disorders, immune diseases, and bone loss diseases.

The term "inflammatory disorders" includes any inflammatory disease, disorder or condition caused, exasperated or mediated by IL-12 production. Such inflammatory disorders may include, without limitation, asthma, adult respiratory distress syndrome, systemic lupus erythematosus, inflammatory bowel disease (including Crohn's disease and ulcerative colitis), multiple sclerosis, insulin-dependent diabetes mellitus, autoimmune arthritis (including rheumatoid arthritis, juvenile rheumatoid arthritis, psoriatic arthritis), inflammatory pulmonary syndrome, pemphigus vulgaris, idiopathic thrombocytopenic purpura, autoimmune meningitis, myasthenia gravis, autoimmune thyroiditis, dermatitis (including atopic dermatitis and eczematous dermatitis), psoriasis, Sjogren's Syndrome (including keratoconjunctivitis sicca secondary to Sjogren's Syndrome), alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions (such as Stevens-Johnson syndrome), leprosy reversal reactions, erythema nodosum leprosum, autoimmune uveitis, allergic encephalomyelitis, aplastic anemia, pure red cell anemia, idiopathic thrombocytopenia, polychondritis, Wegener's granulomatosis, chronic active hepatitis, Graves ophthalmopathy, primary biliary cirrhosis, uveitis posterior and interstitial lung fibrosis.

"Inflammatory disorders" expressly include acute inflammatory disorders. Examples of acute inflammatory disorders include graft versus host disease, transplant rejection, septic shock, endotoxemia, Lyme arthritis, infectious meningitis (e.g., viral, bacterial, Lyme disease-associated), an acute episode of asthma and acute episodes of an autoimmune disease.

"Inflammatory disorders" expressly include chronic inflammatory disorders. Nonlimiting examples of chronic inflammatory disorder include asthma, rubella arthritis, and chronic autoimmune diseases, such as systemic lupus erythematosus, psoriasis, inflammatory bowel disease, including Crohn's disease and ulcerative colitis, multiple sclerosis and rheumatoid arthritis.

The term "immune diseases" includes any immune disease, disorder or condition caused, exasperated or mediated by IL-12 production. Such immune diseases may include, without limitation, rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, common variable immunodeficiency (CVID), antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The term "bone loss disease" includes any bone loss disease, disorder or condition caused, exasperated or mediated by IL-12 production e.g., periodontal disease, non-malignant bone disorders (e.g., osteoporosis, Paget's disease of bone, osteogenesis imperfecta, fibrous dysplasia, and primary hyperparathyroidism), estrogen deficiency, inflammatory bone loss, bone malignancy, arthritis, osteopetrosis, and certain cancer-related disorders (e.g., hypercalcemia of malignancy (HCM), osteolytic bone lesions of multiple myeloma and osteolytic bone metastases of breast cancer and other metastatic cancers.

In the case of overlap in these definitions, the disease, condition or disorder may be considered to be a member of any of the above listed classes of IL-12 overproduction-related disorders. In one embodiment, IL-12 overproduction related diseases include rheumatoid arthritis, sepsis, Crohn's disease, multiple sclerosis, psoriasis, or insulin-dependent diabetes mellitus.

The compounds and compositions described herein are useful to treat and prevent any IL-12 production-related disorders, e.g., inflammatory disorders, immune diseases, and bone loss diseases. The method involves administering an effective amount of a compound of the invention, or a pharmaceutically acceptable salt, solvate, clathrate, hydrate, polymorph, or prodrug thereof, to a subject in need of treatment of IL-12 overproduction related diseases. In preferred embodiments, treatment according to the invention provides a reduction in or prevention of at least one symptom or manifestation of an IL-12-, IL-23-, or IL-27-related disorder (e.g., inflammatory disorder, immune diseases, or bone loss disease), as determined in vivo or in vitro of at least about 10%, more preferably 20%, 30%, 40%, 50%, 60%, 70%, 80%, 90%, 95%, 98% or 99%.

As used herein, the term "effective amount" refers to an amount of a compound of this invention which is sufficient to reduce or ameliorate the severity, duration, progression, or onset of an inflammatory disorder, immune diseases, or bone loss disease, prevent the advancement of an inflammatory disorder, immune diseases, or bone loss disease, cause the regression of an inflammatory disorder, immune diseases, or bone loss disease, prevent the recurrence, development, onset or progression of a symptom associated with an inflammatory disorder, immune diseases, or bone loss disease, or enhance or improve the prophylactic or therapeutic effect(s) of another therapy.

The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the heterocyclic compound of this invention can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

To practice the method of the present invention, a compound disclosed herein, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A heterocyclic compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the compounds of the invention. Examples of other carriers include colloidal silicon dioxide, magnesium stearate, cellulose, sodium lauryl sulfate, and D&C Yellow # 10.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

The biological activities of the compounds of the invention can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A compound of the invention can also be evaluated by animal studies. For example, one of such studies involves the ability of a test compound to treat adjuvant arthritis (i.e., a IL-12 overproduction related disorder) in rats.

In certain embodiments, pharmaceutical compositions and dosage forms of the invention comprise one or more active ingredients in relative amounts and formulated in such a way that a given pharmaceutical composition or dosage form inhibits the uptake of calcium. Preferred pharmaceutical compositions and dosage forms comprise a compound of formula (I), or a pharmaceutically acceptable prodrug, salt, solvate, or clathrate thereof, optionally in combination with one or more additional active agents.

The methods for treating or preventing disorders associated with excessive bone loss in a patient in need thereof can further comprise administering to the patient being administered a compound of this invention, an effective amount of one or more other therapeutic agents. Such therapeutic agents may include other therapeutic agents such as those conventionally used to prevent or treat disorders associated with excessive bone resorption or symptoms thereof. For example, such other agents include anti-resorptive agents for example progestins, polyphosphonates, bisphosphonate(s), estrogen agonists/antagonists, estrogen (such as Premarin®), estrogen/progestin combinations, and estrogen derivatives (such as estrone, estriol or 17α, 17β-ethynyl estradiol).

In such combination therapy treatment, both the compounds of this invention and the other drug agent(s) are administered to mammals (e.g., humans, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective amount would be where the other therapeutic agent is not administered. In another embodiment, the effective amount of the conventional agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, dthynodiol diacetate, etonogestrel, flurogestone acetate, gestaclone, gestodene, gestonorone caproate, gestrinone, haloprogesterone, hydroxyprogesterone, caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenpropionate, progesterone, quingestanol acetate, quingestrone, and tigestol. Preferred progestins are medroxyprogestrone, norethindrone and norethynodrel.

Exemplary bone resorption inhibiting polyphosphonates include polyphosphonates of the type disclosed in U.S. Pat. No. 3,683,080. Preferred polyphosphonates are geminal dipolyphosphonates (also referred to as bis-phosphonates).

Tiludronate disodium is an especially preferred polyphosphonate. Ibandronic acid is an especially preferred polyphosphonate. Alendronate is an especially preferred polyphosphonate. Zoledronic acid is an especially preferred polyphosphonate. Other preferred polyphosphonates are 6-amino-1-hydroxy-hexylidene-biphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N(2-hydroxyethyl)amino methane diphosphonic acid, butane-4-amino-1- hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used for this purpose. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue; and blocking the actions of estrogen in one or more tissues. Such activities are readily determined by those skilled in the art of standard assays including estrogen receptor binding assays, standard bone histomorphometric and densitometer methods, and E. F Eriksen et al., Bone Histomorphometry, Raven Press, New York, pp. 1-74 (1994); S. J. Grier et. al., The Use of Dual-Energy X-Ray Absorptiometry In Animals, Inv. Radiol. 31(1): 50-62 (1996); Wahner H. W. and Fogelman I., The Evaluation of Osteoporosis: Dual Energy X-Ray Absorptiometry in Clinical Practice, Martin Dunitz Ltd., London, pp. 1-296 (1994)). A variety of these compounds are described and referenced below.

A preferred estrogen agonist/antagonist is droloxifene: (phenol, 3-(1-(4-(2-(dimethylamino)ethoxy)phenyl)-2-phenyl-1-butenyl)-,(E)-) and related compounds which are disclosed in U.S. Pat. No. 5,047,431. Another preferred estrogen agonist/antagonist is 3-(4-(1,2-diphenyl-but-1-enyl)-phenyl)-acrylic acid, which is disclosed in Wilson et al., Endocrinology 138: 3901-11 (1997). Another preferred estrogen agonist/antagonist is tamoxifen: (ethanamine,2-(-4-(1,2-diphenyl-1-butenyl)phenoxy)-N,N-dimethyl, (Z)-2-,2-hydroxy-1,2,3-propanetricarboxylate(1:1)) and related compounds which are disclosed in U.S. Pat. No. 4,536,516. Another related compound is 4-hydroxy tamoxifen which is disclosed in U.S. Pat. No. 4,623,660.

A preferred estrogen agonist/antagonist is raloxifene: (methanone,(6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine,2-(4-(4-chloro-1,2-diphenyl-1-butenyl)phenoxy)-N, N-dimethyl-, (Z)-,2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2,dimethyl-3-phenyl-chroman-4-yl)-phenoxy)-ethyl)-pyrrolidine, which is disclosed in U.S. Pat. No. 3,822,287. Also preferred is levormeloxifene. Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2- (4-hydroxy-phenyl)-benzo[b]thiophen-3-yl)-methanone which is disclosed, along with methods of preparation, in PCT publication no. WO 95/10513 assigned to Pfizer Inc. Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetrahydro-naphthalene-2-ol; (−)-cis-6-phenyl-5-(4-(2-pyrrolidin-1-yl-ethoxy)-phenyl)-5,6,7,8-tetrahydro-naphthalene-2-ol; cis-6-phenyl-5-(4-(2-pyrrolidin-1-yl-ethoxy)-phenyl)-5,6,7,8-tetrahydro-naphthalene-2-ol; cis-1-(6'-pyrrolodinoethoxy-3'-pyridyl)-2-phenyl-6- hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydro-naphthalene-2-ol; and 1-(4'-pyrrolidinolethoxyphenyl)-2-phenyl-6-hydroxy-1,2,3,4-tetrahydroisoquinoline. Other estrogen agonist/antagonists are described in U.S. Pat. No. 4,133,814. U.S. Pat. No. 4,133,814 discloses derivatives of 2-phenyl-3-aroyl-benzothiophene and 2-phenyl-3-aroylbenzothiophene-1-oxide.

Those skilled in the art will recognize that other bone anabolic agents, also referred to as bone mass augmenting agents, may be used in conjunction with the compounds of this invention. A bone mass augmenting agent is a compound that augments bone mass to a level which is above the bone fracture threshold as detailed in the World Health Organization Study World Health Organization, "Assessment of Fracture Risk and its Application to Screening for Postmenopausal Osteoporosis (1994). Report of a WHO Study Group. World Health Organization Technical Series 843." Any prostaglandin, or prostaglandin agonist/antagonist may be used in combination with the compounds of this invention. Those skilled in the art will recognize that IGF-1, sodium fluoride, parathyroid hormone (PTH), active fragments of parathyroid hormone, growth hormone or growth hormone secretagogues may also be used. The following paragraphs describes in greater detail exemplary compounds that may be administered in combination with compounds of this invention Prostaglandins: The term prostaglandin refers to compounds which are analogs of the natural prostaglandins $PGD_1$, $PGD_2$, $PGE_2$, $PGE_1$ and $PGF_2$ which are useful in the treatment of osteoporosis and other disorders associated with excessive osteoclastic bone resorption. These compounds bind to the prostaglandins receptors. Such binding is readily determined by those skilled in the art of standard assays (e.g., S. An et al., Cloning and Expression of the $EP_2$ Subtype of Human Receptors for Prostaglandin $E_2$ Biochemical and Biophysical Research Communications, 197(1): 263-270 (1993)).

Prostaglandins are alicyclic compounds related to the basic compound prostanoic acid. The carbon atoms of the basic prostaglandin are numbered sequentially from the carboxylic carbon atom through the cyclopentyl ring to the terminal carbon atom on the adjacent side chain. Normally the adjacent side chains are in the trans orientation. The presence of an oxo group at C-9 of the cyclopentyl moiety is indicative of a prostaglandin within the E class while $PGE_2$ contains a trans unsaturated double bond at the $C_{13}$-$C_{14}$ and a cis double bond at the $C_5$-$C_6$ position.

A variety of prostaglandins are described and referenced below. However, other prostaglandins will be known to those skilled in the art. Exemplary prostaglandins are disclosed in U.S. Pat. Nos. 4,171,331 and 3,927,197. Norrdin et al., The Role of Prostaglandins in Bone in Vivo, Prostaglandins Leukotriene Essential Fatty Acids 41: 139-150 (1990) is a review of bone anabolic prostaglandins. Any prostaglandin agonist/antagonist may be used in combination with the compounds of this invention. The term prostaglandin agonist/antagonist refers to compounds which bind to prostaglandin receptors (eg., An S. et al., Cloning and Expression of the $EP_2$ Subtype of Human Receptors for Prostaglandin $E_2$, Biochemical and Biophysical Research Communications 197(1): 263-70 (1993)) and mimic the action of prostaglandin in vivo (e.g., stimulate bone formation and increase bone mass). Such actions are readily determined by those skilled in the art of standard assays. Eriksen E. F. et al., Bone Histomorphometry, Raven Press, New York, 1994, pp. 1-74; S. J. Grier et al., The Use of Dual-Energy X-Ray Absorptiometry In Animals, Inv. Radiol. 31(1): 50-62 (1996); H. W. Wahner and I. Fogelman, The Evaluation of Osteoporosis: Dual Energy X-Ray Absorptiometry in Clinical Practice, Martin Dunitz Ltd. London, pp. 1-296 (1994). A number of these compounds are described and reference below. However, other prostaglandin agonists/antagonists will be known to those skilled in the art. Exemplary prostaglandin agonists/antagonists are disclosed as follows. U.S. Pat. No. 3,932,389 discloses 2-descarboxy-2-(tetrazol-5-yl)-11-desoxy-15-substituted-omega-pentanorprostaglandins useful for bone formation activity. U.S. Pat. No. 4,018,892, discloses 16-aryl-13,14-dihydro-$PGE_2$ p-biphenyl esters useful for bone formation activity. U.S. Pat. No. 4,219,483, discloses 2,3,6-substituted-4-pyrones useful for bone formation activity. U.S. Pat. No. 4,132,847, discloses 2,3,6-substituted-4-pyrones useful for bone formation activity. U.S. Pat. No. 4,000,309, discloses 16-aryl-13,14-dihydro-$PGE_2$ p-biphenyl esters useful for bone formation activity. U.S. Pat. No. 3,982,016, discloses 16-aryl-13,14-dihydro-$PGE_2$ p-biphenyl esters useful for bone formation activity. U.S. Pat. No. 4,621,100, discloses substituted cyclopentanes useful for bone formation activity. U.S. Pat. No. 5,216,183, discloses cyclopentanones useful for bone formation activity.

Sodium fluoride may be used in combination with the compounds of this invention. The term sodium fluoride refers to sodium fluoride in all its forms (e.g., slow release sodium fluoride, sustained release sodium fluoride). Sustained release sodium fluoride is disclosed in U.S. Pat. No. 4,904,478. The activity of sodium fluoride is readily determined by those skilled in the art of biological protocols.

Bone morphogenetic protein may be used in combination with the compounds of this invention (e.g., see Ono et al., Promotion of the Osteogenetic Activity of Recombinant Human Bone Morphogenetic Protein by Prostaglandin $E_1$, Bone 19(6): 581-588 (1996)).

Any parathyroid hormone (PTH) may be used in combination with the comound of this invention. The term parathyroid hormone refers to parathyroid hormone, fragments or metabolites thereof and structural analogs thereof which can stimulate bone formation and increase bone mass. Also included are parathyroid hormone related peptides and active fragments and analogs of parathyroid related peptides (see PCT publication No. WO 94/01460). Such bone anabolic functional activity is readily determined by those skilled in the art of standard assays. A variety of these compounds are described and referenced below. However, other parathyroid hormone will be known to those skilled in the art. Exemplary parathyroid hormones are disclosed in the following references. "Human Parathyroid Peptide Treatment of Vertebral Osteoporosis", Osteoporosis Int., 3, (Supp 1): 199-203. "PTH 1-34 Treatment of Osteoporosis with Added Hormone Replacement Therapy: Biochemical, Kinetic and Histological Responses" Osteoporosis Int. 1: 162-170.

Any growth hormone or growth hormone secretagogue may be used in combination with the compounds of this invention. The term growth hormone secretagogue refers to a compound which stimulates the release of growth hormone or mimics the action of growth hormone (e.g., increases bone formation leading to increased bone mass). Such actions are readily determined by those skilled in the art of standard assays well known to those of skill in the art. A variety of these compounds are disclosed in the following published PCT patent applications: WO 95/14666; WO 95/13069; WO 94/19367; WO 94/13696; and WO 95/34311. However, other growth hormones or growth hormone secretagogues will be known to those skilled in the art. In particular, a preferred growth hormone secretagogue is N-[1(R)-[1,2-Dihydro-1-methanesulfonylspiro[3H-indole-3,4'-piperidin]-1'-yl)carbonyl]-2-(phenylmethyloxy)ethyl]-2-amino-2-methylpropanamide:MK-667. Other preferred growth hormone secretagogues include 2-amino-N-(2-(3a-(R)-benzyl-2-methyl-3-oxo-2,3,3a,4,6,7-hexahydro-pyrazolo-[4,3-c]pyridin-5-yl)-1-(R)-benzyloxymethyl-2-oxo-ethyl)-isobutyramide or its L-tartaric acid salt; 2-amino-N-(1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl) isobutyramide; 2-amino-N-(2-(3a-(R)-benzyl-3-oxo-2,3,3a,4,6,7-hexahydro-pyrazolo[4,3-c]pyridin-5-yl)-1-(R) benzyloxymethyl-2-oxo-ethyl)isobutyramide; and 2-amino-N-(1-(2,4-difluoro-benzyloxymethyl)-2-oxo-2-(3-oxo-3a-pyridin-2-ylmethyl-2-(2,2,2-trifluoro-ethyl)-2,3,3a,4,6,7-hexahydro-pyrazolo[4,3-c]pyridin-5-yl)-ethyl)-2-methyl-propionamide.

The other therapeutic agent can be a steroid or a non-steroidal anti-inflammatory agent. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxipinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

For arthritis, inflammation-mediated bone loss and other disorders that have an inflammatory component, preferred conventional treatments for use in combination therapy with the compounds and compositions of this invention include (without limitation) naproxen sodium (Anaprox® and Anaprox® DS, Roche), flurbiprofen (Ansaid®; Pharmacia), diclofenac sodium+misoprostil (Arthrotec®, Searle), valdecoxib (Bextra®, Pharmacia), diclofenac potassium (Cataflam® and Voltaren®, Novartis), celecoxib (Celebrex®, Pharmacia), sulindac (Clinoril®, Merck), oxaprozin (Daypro®, Pharmacia), salsalate (Disalcid®, 3M), diflunisal (Dolobid®, Merck), naproxen sodium (EC Naprosyn®, Roche), piroxicam (Feldene®, Pfizer), indomethacin (Indocin® and Indocin SR®, Merck), etodolac (Lodine® and Lodine XL®, Wyeth), meloxicam (Mobic®, Boehringer Ingelheim), ibuprofen (Motrin®, Pharmacia), naproxen (Naprelan®, Elan), naproxen (Naprosyn®, Roche), ketoprofen (Orudis® and Oruvail®, Wyeth), nabumetone (Relafen®, SmithKline), tolmetin sodium (Tolectin®, McNeil), choline magnesium trisalicylate (Trilisate®, Purdue Fredrick), and rofecoxib (Vioxx®, Merck).

In any case where pain in a component of the target disorder, the other therapeutic agent can be an analgesic. Useful analgesics include, but are not limited to, phenacetin, butacetin, acetaminophen, nefopam, acetoamidoquinone, and mixtures thereof.

For use against osteoporosis, Paget's disease and other disorders associated with bone deterioration, preferred conventional agents that mayu be used in combination with compounds and compositions of this invention include (without limitation) bisphosphonates (such as etidronate (Didronel®, Procter & Gamble), pamidronate (Aredia®, Novartis), and alendronate (Fosamax®, Merck)), tiludronate (Skelid®, Sanofi-Synthelabo, Inc.), risedronate (Actonel®, Procter & Gamble/Aventis), calcitonin (Miacalcin®), estrogens (Climara®, Estrace®, Estraderm®, Estratab®, Ogen®, Ortho-Est®, Vivelle®, Premarin®, and others) estrogens and progestins (Activella™, FemHrt®, Premphase®, Prempro®, and others), parathyroid hormone and portions thereof, such as teriparatide (Forteo®, Eli Lilly and Co.), selective estrogen receptor modulators (SERMs) (such as raloxifene (Evista®)) and treatments currently under investigation (such as other parathyroid hormones, sodium fluoride, vitamin D metabolites, and other bisphosphonates and selective estrogen receptor modulators).

Any method of the present invention can comprise administering an effective amount of a composition or pharmaceutical composition comprising at least one compound of this invention to a cell, tissue, organ, animal or patient in need of such modulation, treatment or therapy. Such a method can optionally further comprise co-administration or combination therapy for treating an IL-12 production related disorder, wherein the administering further comprises administering before, concurrently with, and/or after the compound of this invention, at least one additional active agent selected from a TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonistm. Suitable dosages are well known in the art. See, e.g., Wells et al., eds., Pharmacotherapy Handbook, 2. sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

TNF antagonists suitable for compositions, combination therapy, co-administration, devices and/or methods of the present invention include, but are not limited to, anti-TNF antibodies (such as, Remicade (Infliximab) or Humira (adalimumab)) for example, or, antigen-binding fragments thereof, and receptor molecules which bind specifically to TNF (such as, for example, Enbrel (Etanercept)); compounds which prevent and/or inhibit TNF synthesis, TNF release or its action on target cells, such as thalidomide, tenidap, phosphodiesterase inhibitors (e.g, pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

For clarifiation, a "tumor necrosis factor antibody," "TNF antibody," "TNF antibody," or fragment and the like decreases, blocks, inhibits, abrogates or interferes with TNF activity in vitro, in situ and/or preferably in vivo. For example, a suitable TNF human antibody of the present invention can bind TNFa and includes anti-TNF antibodies, antigen-binding fragments thereof, and specified mutants or domains thereof that bind specifically to TNFa. A suitable TNF anttibody or fragment can also decrease block, abrogate, interfere, prevent and/or inhibit TNF RNA, DNA or protein synthesis, TNF release, TNF receptor signaling, membrane TNF cleavage, TNF activity, TNF production and/or synthesis.

The foregoing and other useful combination therapies will be understood and appreciated by those of skill in the art. Potential advantages of such combination therapies include the ability to use less of each of the individual active ingredients to minimize toxic side effects, synergistic improvements in efficacy, improved ease of administration or use and/or reduced overall expense of compound preparation or formulation.

Responsiveness of a particular condition, disease or disorder to compounds and compositions of this invention can be measured directly by comparison against conventional drugs, or can be inferred based on an understanding of disease etiology and progression. There are a number of cellular and bone resorption assay systems that are widely accepted in the art as predictive of in vivo effects. As the bone resorption assay uses material that includes all bone cells, it is an ex vivo assay. Thus, the showing that a compound of this invention inhibits bone resorption in these assays is evidence of the clinical utility of these for treating or preventing conditions associated with excessive bone loss. Various scientific publications (such as Carano et al. J. Clin. Invest. 85: 456-461 (1990); Blair & Schlesinger, The Biology and Physiology of the Osteoclast, CRC Press, Eds., Gay, C. V. and Rifkin, B. R., pp. 259-288 (1992); and Vaananen et al., J. Cell Biology 111: 1305-1311 (1990)) support the fact that such assays are accepted as being predictive of in vivo activity. Furthermore, the in vitro effects of Herbimycin A on bone resorption were shown to correlate with in vivo activity (Yoneda et al., J. Clin. Invest. 91: 2791-95 (1993)).

Without further elaboration, it is believed that the above description has adequately enabled the present invention. The following specific embodiments are, therefore, to be construed as merely illustrative, and not limitative of the remainder of the disclosure in any way whatsoever. All of the references and publications cited herein are hereby incorporated by reference in their entirety.

The compounds described herein can be prepared by methods well known in the art, as well as by the synthetic routes disclosed herein. For example, a pyrimidine compound can be prepared by using 2,4,6-trichloro-pyrimidine as a starting material. The three chloro groups can be displaced by various substitutes. More specifically, a first chloro group (e.g., at position 6) can react with, e.g., dimethyl amine, to form a dimethylamino pyrimidine. 2-Aryl and 2-alkylpyrimidine dichloro compounds can also be prepared by reacting an amidine with a malonic ester followed by treatment with phosphorous oxychloride. A second chloro group can be replaced by reacting with a nucleophile, such as an alcohol in the presence of base, e.g., sodium hydride. In other examples, a compound of formula (I), wherein Y is $CH_2$ can be prepared by reacting the pyrimidine chloride with a Grignard reagent, an organotin reagent, an organocopper reagent, an organoboric acid, or an organozinc reagent in the presence of an organopalladium compound as a catalyst. Isomeric forms may be produced. The desired isomeric product can be separated from others by, e.g., high performance liquid chromatography. A third chloro group can undergo a displacement reaction with, e.g., hydrazine, and the primary amine of the coupled hydrazine moiety further reacts with an aldehyde, e.g., indole-3-carboxaldehyde to form a hydrazone linkage. Thus, a pyrimidine compound of this invention is obtained.

Alternatively, instead of the hydrazone linkage describe above, the compounds may have an amide linkage (see Scheme I below). The synthesis consists of 3 steps. First, to a stirred solution of 4-(2-hydroxyethyl)morpholine (B) (2.8 g, 21.3 mmol) in anhydrous THF (45 mL) at 0° C., sodium hydride, 60% dispersion in mineral oil, (0.9 g, 22.5 mmol) is added in three portions under nitrogen purge. Ice-bath was removed and a mixture is stirred at room temperature for 20-30 minutes. The mixture is cooled to 0° C. and added drop-wise (using syringe or dropping funnel) under nitrogen purge to a solution of methyl 2,4-dichloropyrimidine carboxylate (A) (4.03 g, 19.4 mmol) in anhydrous THF (35 mL) at 0° C. The resultant solution is stirred for 30 minutes at 0° C., followed by 30 minutes at room temperature. It is then quenched carefully with ice-water (115 mL) and diluted with ethyl acetate (115 mL). Organic layer is separated, water layer extracted once with ethyl acetate, combined ethyl acetate extracts are washed with brine and dried over anhydrous sodium sulfate. Concentration, followed by column chromatography with gradient elutaion (hexane:ethyl acetate, 1:1; hexane:ethyl acetate, 1:2; ethyl acetate; dichloromethane-acetone-methanol, 3:1:01) affords 3 fractions: first (0.56 g, 9.5% )—mostly isomer C, second (1.28 g, 21.8%)—a mixture of C and D, and byproduct (E), third (0.7 g, 11.9%)—mostly isomer (D).

In the second step, a solution of compound C (0.6 g, 2 mmol), 5-amino-2,3-dimethylindole (F) (0.32 g, 2 mmol) and DIPEA (0.28 g, 2.2 mmol) in dioxane is heated at reflux for two hours. Ethyl acetate and water are added to the concentrated reaction mixture, water layer extracted with ethyl acetate, combined ethyl acetate extracts washed with brine and dried over anhydrous sodium sulfate. Product G (0.64 g, 75%) is isolated by column chromatography with gradient eluation (ethyl acetate; dichloromethane-acetone-methanol, 3:1:01).

In the same manner compound D is converted into product H.

Compounds H is then converted into their corresponding amides (I) using appropriate amines following general procedure for amide formation.

To a stirred mixture of ester (1 mmol) and amine (1.05 mmol) in toluene (3.2 mL), 2 M solution of trimethylaluminum in toluene (1.6 eq) is added drop-wise under nitrogen purge. The reaction mixture is stirred until gas evolution halted, and then mixture is micro waved at 120° C. for 5-7 minutes (Emrys Optimizer). To the reaction mixture were added 1N NaOH solution and dichloromethane, organic layer separated, washed with water, brine and dried over anhydrous sodium sulfate. Flash column chromatography purification affords about 65-75% of a desired amide (I).

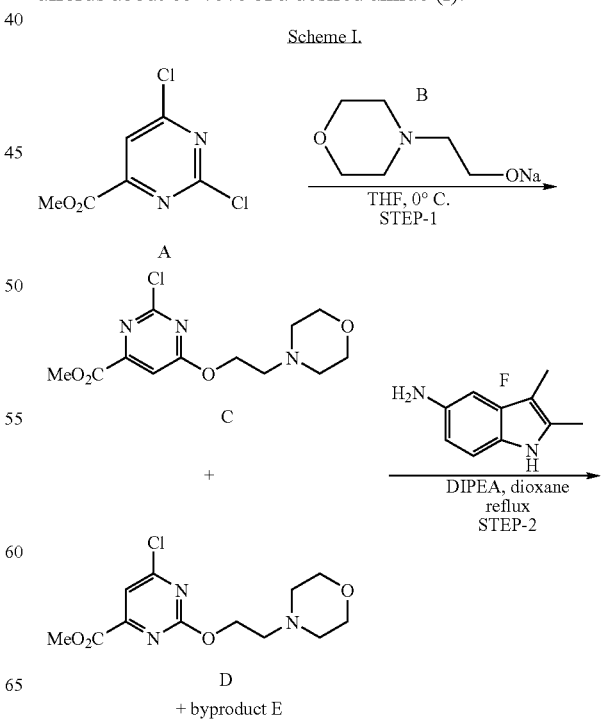

Scheme I.

83
-continued

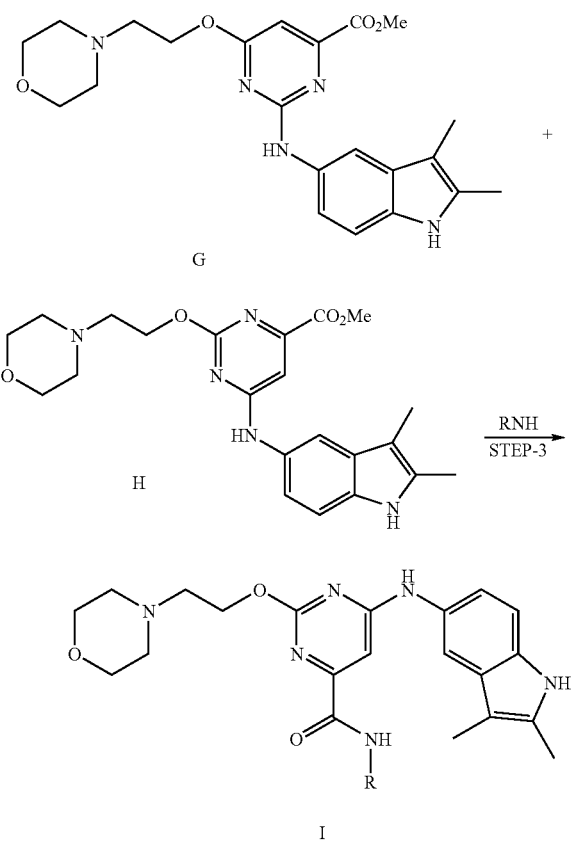

If preferred, other types of linkages can be prepared by similar reactions. Sensitive moieties on a pyrimidinyl intermediate and a nucleophile can be protected prior to coupling. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the heterocyclic compounds. In addition, various synthetic steps may be performed in an alternate sequence or order to give the desired compounds. Synthetic chemistry transformations and protecting group methodologies (protection and deprotection) useful in synthesizing applicable heterocyclic compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A compound of the present invention thus obtained can be further purified by flash column chromatography, high performance liquid chromatography, or crystallization.

Correspondingly, pyridine, pyridinyl and triazinyl compounds described herein can be made according to methods know in the art, including those in the aforementioned treatises. The pyridinyl and triazinyl compounds can be made using analogous synthetic procedures and reagents as described for the pyrimidinyl compounds. It is recognized by one of ordinary skill that pyrimidines demonstrate reactivity intermediate relative to that of pyridines and triazines, therefore reaction conditions (e.g., temperature, reaction time, etc.) may be adjusted accordingly, which is routine for one of ordinary skill.

Other features, objects, and advantages of the invention will be apparent from the description and from the claims.

EXAMPLES

Example 1

Synthesis of Compound 30

The synthesis of the 30 consists of 4 steps. The following scheme depicts the synthetic route:

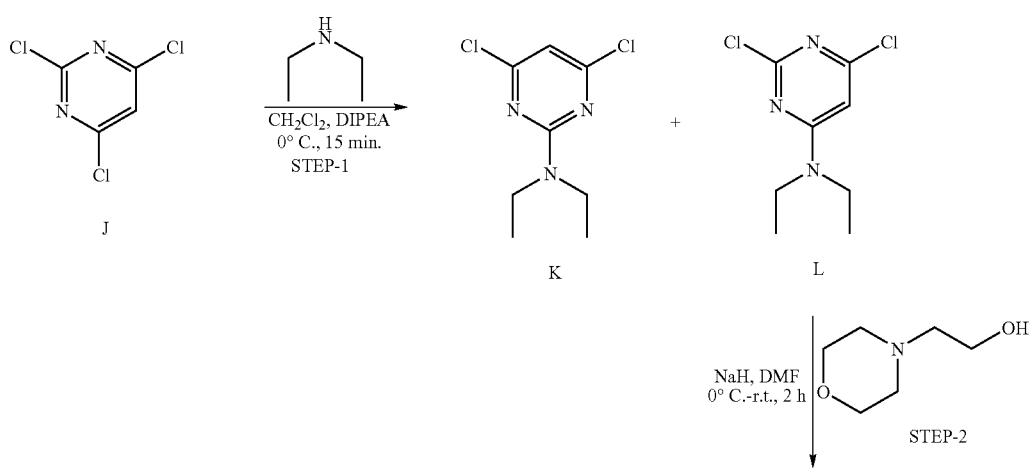

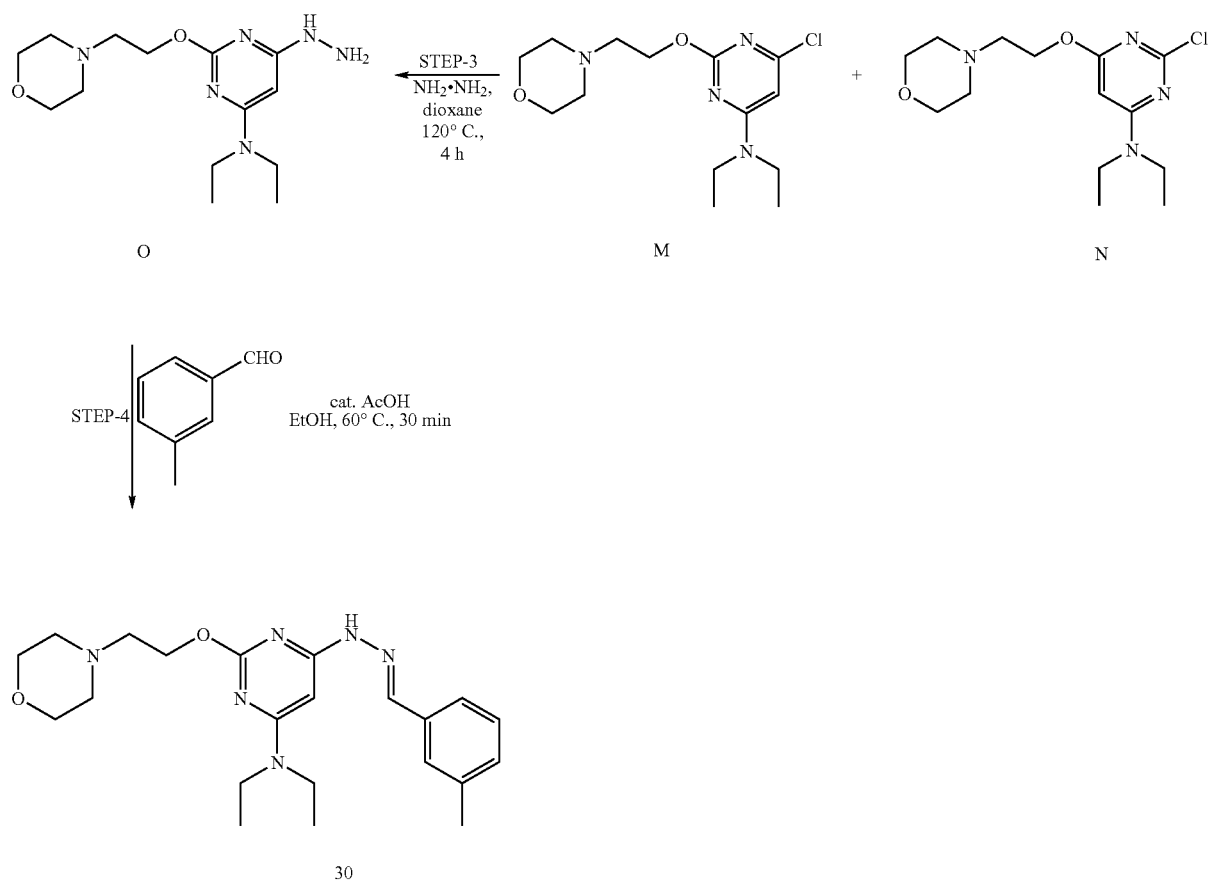

STEP-1: Synthesis of (2,6-Dichloro-pyrimidin-4-yl)-diethyl-amine L

To a stirred solution of 2.0 g (10.90 mmols) of 2,4,6-trichloropyrimidine in 25 mL of anhydrous ethanol at 0° C., was added drop wise a solution 0.79 g (10.90 mmols) of diethylamine in 5 mL of ethanol. This was followed by the addition of 2.3 mL (16.35 mmols) of triethylamine and the mixture was stirred for further 30 min. The mixture was then concentrated and 25 mL of $CH_2Cl_2$ and 25 mL of water were added. The organic layer was separated and the aqueous layer was extracted by additional amount of dichloromethane (2×10 mL) and the extracts were combined, dried over anhydrous $Na_2SO_4$ and concentrated. Column chromatography on silica gel afforded 1.48 g (62%) of L as colorless solid.

STEP-2: Synthesis of [6-Chloro-2-(2-morpholin-4-yl-ethoxy)-pyrimidin-4-yl]-diethyl-amine M To a mixture of 1.48 g (6.72 mmols) of the intermediate L and 0.89 g (6.72 mmols) of 2-Morpholin-4-yl-ethanol in 25 mL of anhydrous DMF at 0 C, was added 0.4 g of NaH portion wise. With a constant purge of nitrogen gas the mixture was stirred at room temperature for 4 h. To the mixture, 50 mL of water and 50 mL of ethylacetate were added. The organic layer was separated and it was successively washed with water (5×20 mL) and dried over anhydrous $Na_2SO_4$. Concentration followed by column chromatography on silica gel afforded 1.72 g (81%) of pure M as white solid.

STEP-3: Synthesis of the Diethyl-[6-hydrazino-2-(2-morpholin-4-yl-ethoxy)-pyrimidin-4-yl]-amine O A mixture of 0.52 (1.65 mmols) of the intermediate M and 0.26 mL (8.26 mmols) of anhydrous hydrazine was heated under reflux in 10 mL of anhydrous dioxane for 6 hrs. The reaction mixture was then concentrated and the product O was precipitated using 75:25 mixture of ethylacetate:hexane to obtain 0.39 g (76%) of the product O as white solid.

STEP-4: Synthesis of Diethyl-[6-[N'-(3-methyl-benzylidene)-hydrazino]-2-(2-morpholin-4-yl-ethoxy)-pyrimidin-4-yl]-amine 30

To a mixture of 0.34 g (1.09 mmols) of the hydrazine O and 0.13 g (1.09 mmols) of m-tolualdehyde in 10 mL of anhydrous ethanol, was added a few drops of glacial acetic acid. The mixture was then heated at 60° C. for 30 min and concentrated. The crude product obtained was then crystallized using ethylacetate to obtain 0.42 g (93%) of the pure product 30 as white solid.

Example 2

Synthesis of 24

Synthesis of 24 consists of 4 steps. The following is the outline of the synthesis.

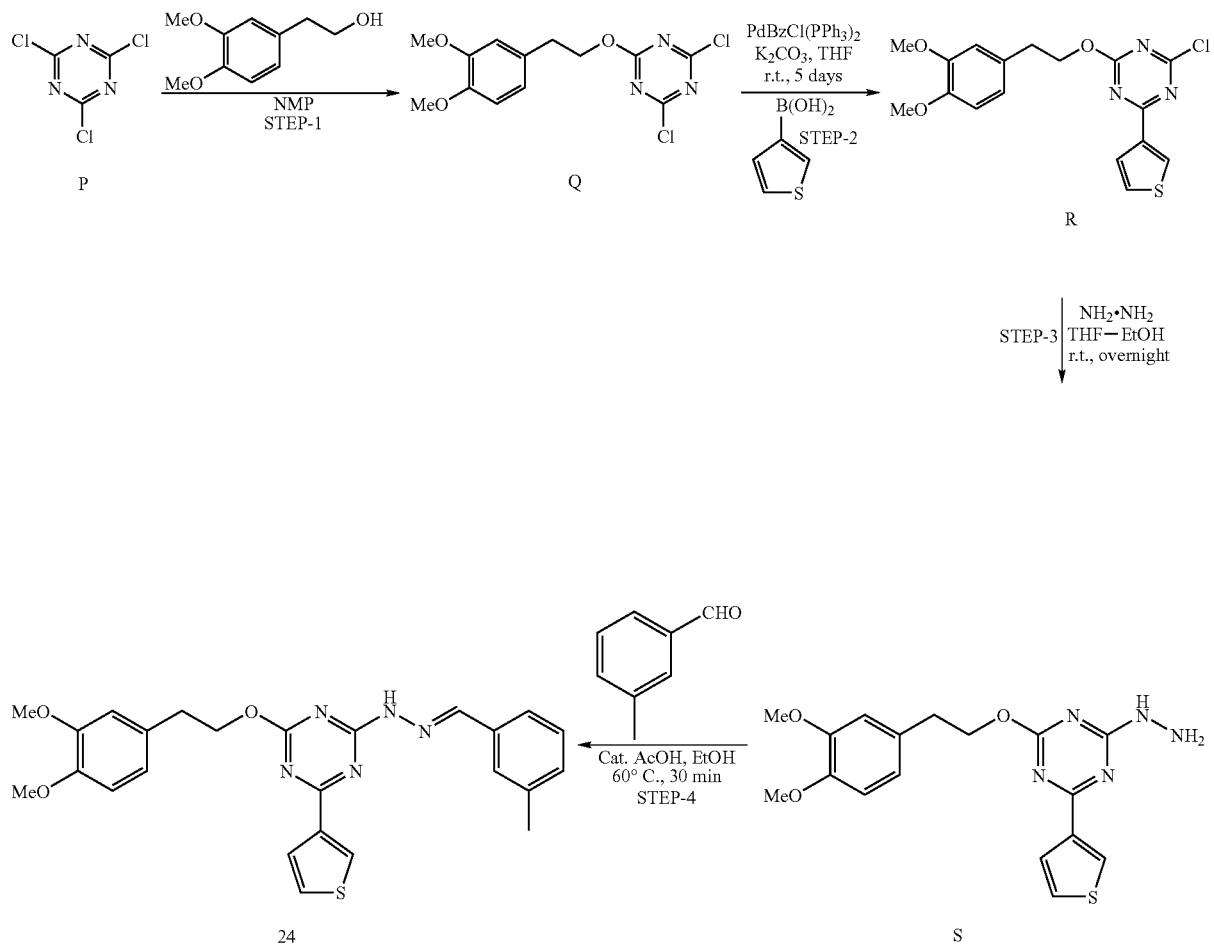

STEP-1: Synthesis of 2,4-Dichloro-6-[2-(3,4-dimethoxy-phenyl)-ethoxy]-[1,3,5]triazine, Q This step is similar to the one described in Example 1, Step-1, except in this case 2-(3,4-dimethoxy-phenyl)-ethanol was used as the nucleophile and NMP was used as the base.

STEP-2: Synthesis of 2-Chloro-4-[2-(3,4-dimethoxy-phenyl)-ethoxy]-6-thiophen-3-yl-[1,3,5]triazine, R A stirred solution of 1.32 g (4.0 mmols) of Q, 0.56 g (4.40 mmols) of thiophene-3-boronic acid and 1.38 g (10 mmol) of $K_2CO_3$ in 25 mL of THF was thoroughly degassed using anhydrous nitrogen gas. This was followed by the addition of 76 mg (0.10 mmols) of the palladium catalyst at once and degassed again. The resultant mixture was stirred under inert atmosphere at room temperature for 5 days and 30 mL of water was added. The organic phase was separated, the aqueous phased was extracted with ethylacetate (2×10 mL) and the combined extracts were dried over $Na_2SO_4$ and concentrated. The crude product was flash chromatographed using 80:20 hexane:ethylacetate to obtain 1.30 g (86%) of the product R as yellow oil.

STEP-3: This step is similar to the one described in Example 1, Step-3, except in this case a mixture THF-EtOH was used as solvent and reaction was carried out at room temperature overnight.

STEP-4: This step is similar to the one described in Example 1, Step-4.

Example 3

Synthesis of 141

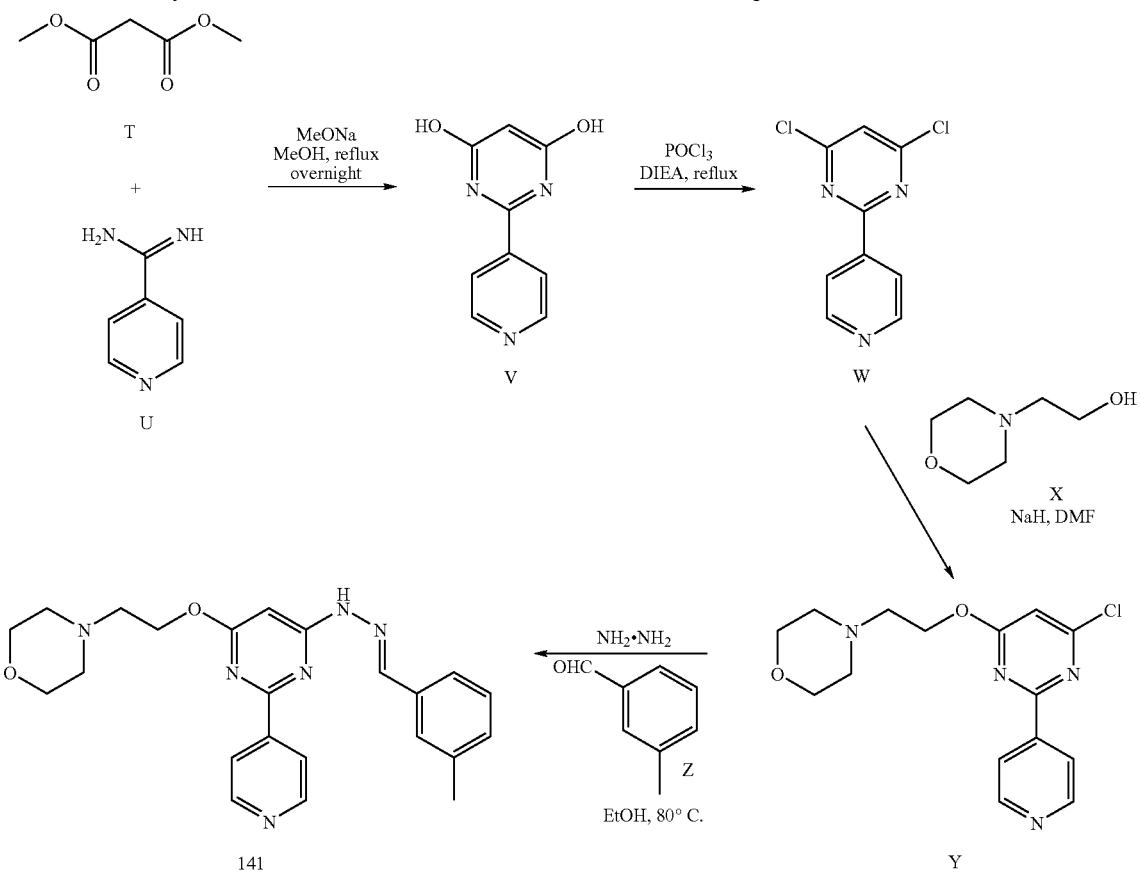

Synthesis of 2-(pyridin-4-yl)pyrimidine-4,6-diol (V)

To a stirred suspension of 5.0 g (23.80 mmols) of amidine U and 3.20 g (23.80 mmols) of methyl acetoacetate T in 100 mL of anhydrous MeOH, was added 5.20 g (95.2 mmols) of solid sodium methoxide portion wise. The resultant mixture was then refluxed overnight then cooled. The mixture was then concentrated, the crude product was dissolved in 100 mL of water and acidified with concentrated HCl till pH 7.5 and then with acetic acid (AcOH) till pH 6. The white precipitate thus obtained was filtered, washed with water and vacuum dried to obtain 4.09 g (91%) of V as white solid.

Synthesis of 4,6-dichloro-2-(pyridin-4-yl)pyrimidine (W)

A suspension of 4.09 g (21.62 mmols) of V, 18 mL (0.10 mol) of diisopropylethylamine in 80 mL of phosphorous oxychloride was stirred at reflux temperature for 3 h. This resulted in black residue in the reaction. The reaction mixture was then concentrated and carefully quenched with water. The product was then extracted with ethyl acetate, washed with brine and dried. Concentration at the rotavapor followed by drying at the pump afforded 1.0 g (20%) of the W as the dark solid. The crude product W was used in the next reaction.

Synthesis of 4-(2-(6-chloro-2-(pyridin-4-yl)pyrimidin-4-yloxy)ethyl)morpholine (Y)

To a mixture of 1.0 g (4.42 mmols) of W and 0.58 g (4.42 mmols) of 2-morpholinoethanol X in 20 mL of anhydrous DMF, was added 0.21 g (5.30 mmols) of sodium hydride portion wise, at room temperature. The resultant mixture was stirred for 2 h and quenched with water. An additional 50 mL of water was added and the product was extracted with ethyl acetate. Concentration followed by passing the crude product through a short pad of silica gel afforded 0.11 g (8%) of the product Y as brown solid. The low yield of this reaction is attributed the highly impure starting material W.

Synthesis of the hydrazone (141): (E)-4-(2-(6-(2-(3-methylbenzylidene)hydrazinyl)-2-(pyridin-4-yl)pyrimidin-4-yloxy)ethyl)morpholine A solution of 0.1 g (0.31 mmols) of Y and 30 µL (0.93 mmols) of anhydrous hydrazine in 2 mL of anhydrous THF was stirred at 100° C. (pressure tube from microwave reactor) for 1 h under microwave irradiation. The solution was then concentrated and vacuum dried. To the crude hydrazine product, was then added excess aldehyde Z (approx. 4-5 equivalents), 10 mL of EtOH and a few drops of AcOH and the mixture was heated at 60° C. for 1 h. The mixture was then concentrated and filtered through a pad of silica gel, eluting first with 1:1 mixture of hexane:ethylacetate to remove the non-polar products. The pad was then eluted with 95:5 EtOAc:MeOH and the eluate was concentrated. The crude product thus obtained was then precipitated using dichloromethane to obtain 70 mg (54%) of the product 141 as yellow solid.

1H-NMR (DMSO, 300 MHz): δ 11.73 (s, 1H), 8.95 (d, J=6.3 Hz, 2H), 8.49 (d, J=6.3 Hz, 2H), 8.18 (s, 1H), 7.55-7.51

(m, 2H), 7.36-7.31 (m, 1H), 7.24-7.22 (m, 1H), 6.62 (s, 1H), 4.91 (bs, 2H), 3.96-3.10 (m, 10H), 2.36 (s, 3H)

Example 4

Synthesis of 146

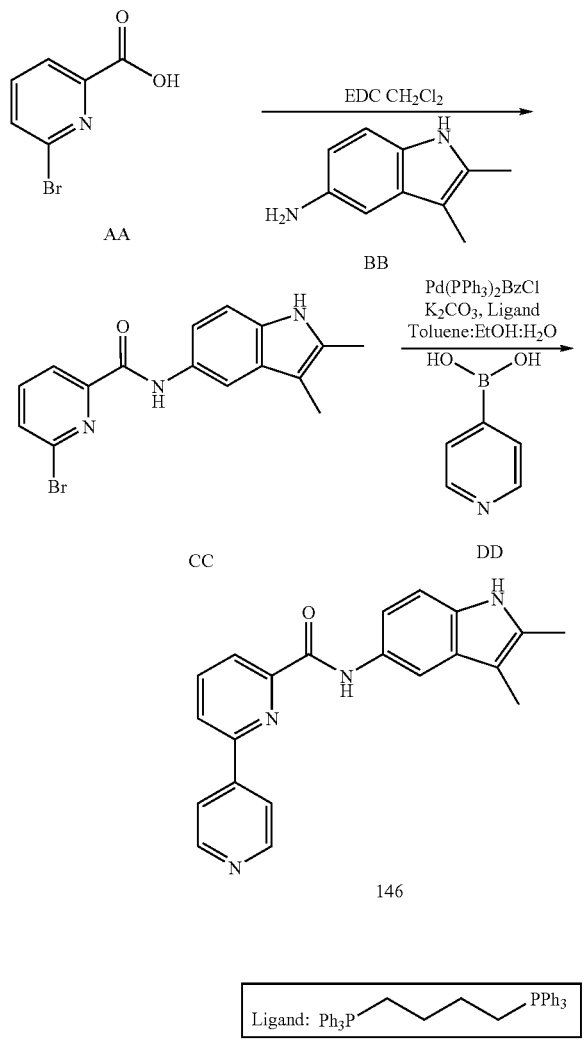

Step 1: Synthesis of 6-bromo-N-(2,3-dimethyl-1H-indol-5-yl)picolinamide (CC)

To a suspension of 0.50 g (2.47 mmols) of the acid AA and 0.4 g (2.47 mmols) of the amine BB in 10 mL of anhydrous dichloromethane, was added 0.52 g (2.72 mmols) of N-(3-dimethylaminopropyl)-N'-ethylcarbodiimide hydrochloride (EDC) followed by catalytic amount (approx 5 mg) of 4-dimethylaminopyridine (DMAP). The resultant mixture was stirred at room temperature overnight. Water work-up followed by precipitation of the crude product with diethyl ether afforded the coupled product CC in pure form.

Step 2: Synthesis of N-(2,3-dimethyl-1H-indol-5-yl)-2,4'-bipyridine-6-carboxamide (146)

To a stirred suspension of 0.20 g (0.58 mmols) of the amide CC, 72 mg (0.58 mmols) of the boronic acid DD, 25 mg (58 μmols) of the ligand, 0.25 g (1.74 mmols) of $K_2CO_3$ in 10 mL of solvent (Toluene:EtOH:$H_2O$=8:1:1), was added under oxygen free atmosphere, 22 mg (29 μmols) of palladium catalyst. The mixture was then heated at 100° C. overnight. Addition of 10 mL of water and 25 mL of EtOAc followed by filtration through celite and extraction of the product using additional EtOAc afforded the product 146 in crude form. Column chromatography on silica gel using EtOAc afforded 73 mg (37%) of the product 146 as off-white solid.

Example 5

ESMS of Synthesized Compounds

The ESMS was calculated and measured for the following compounds.

TABLE 1

| COMPOUND | CALCULATED ESMS | MEASURED ESMS(M + 1) |
|---|---|---|
| 1 | 381.23 | 382.2 |
| 2 | 367.21 | 368.1 |
| 3 | 381.23 | 382.2 |
| 4 | 385.2 | 386.1 |
| 5 | 409.22 | 410.1 |
| 6 | 446.18 | 447.1 |
| 7 | 505.19 | 506.2 |
| 8 | 500.23 | 501.2 |
| 9 | 413.17 | 414.1 |
| 10 | 459.2 | 460.1 |
| 11 | 456.20 | 457.1 |
| 12 | 416.23 | 417.15 |
| 13 | 464.25 | 465.20 |
| 14 | 405.22 | 406.2 |
| 15 | 435.23 | 436.2 |
| 16 | 435.23 | 436.2 |
| 17 | 391.2 | 392.2 |
| 18 | 383.23 | 384.1 |
| 19 | 359.19 | 361.2 |
| 20 | 413.15 | 414.1 |
| 21 | 459.2 | 460.2 |
| 22 | 427.14 | 428.1 |
| 23 | 469.21 | 470.2 |
| 24 | 475.17 | 476.2 |
| 25 | 402.22 | 403.20 |
| 26 | 388.20 | 389.15 |
| 27 | 313.19 | 314.20 |
| 28 | 477.21 | 478.20 |
| 29 | 500.21 | 501.2 |
| 30 | 412.26 | 413.4 |
| 31 | 428.25 | 429.1 |
| 32 | 425.21 | 426.0 |
| 33 | 438.24 | 439.1 |
| 34 | 480.25 | 481.1 |
| 35 | 425.21 | 426.0 |
| 141 | 418.49 | 419.2 |
| 142 | 333.16 | 334.1 |
| 147 | 437.54 | 438.3 |
| 148 | 481.23 | 482.1 |

Example 6

In Vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St Louis, Mo.). Human and mouse recombinant IFNγ were purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 µg/mL streptomycin. PBMC were plated in wells of a 96-well plate at a concentration of $5 \times 10^5$ cells/well, and primed by adding IFNγ (30 U/mL) for 22 h and stimulated by adding LPS (1 µg/mL), or by adding IFNγ (100 U/mL) and then stimulated by adding SAC (0.01%). A test pyrimidine compound was dissolved in DMSO, and added to wells of the 96-well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the pyrimidine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with $1 \times 10^6$ cells/well. The splenocytes were then stimulated with a combination of IFNγ (60 ng/mL) and SAC (0.025%) [or LPS (20 µg/mL)] in the presence of a test compound. Cell-free supernatants were taken 24 h later for the measurement of cytokines. The preparation of compound and the assessment of cell viability were carried out as described above. Mouse IL-12 p70, IL-10, IL-1β, and TNFα were measured using ELISA kits from Endogen, according to the manufacturer's instructions.

The biological activities of compounds were tested on human PBMC or THP-1 cells. Representative results are shown in Table 2.

TABLE 2

Representative in vitro $IC_{50}$ data

| COMPOUND | $IC_{50}$ |
|---|---|
| 1 | 13 uM |
| 2 | 13.6 uM |
| 3 | 7.8 uM |
| 4 | 12.97 uM |
| 5 | 12 uM |
| 7 | 20–53 nM |
| 8 | 0.5 uM |
| 11 | 0.5 uM |
| 15 | 20–56 nM |
| 16 | 1064 nM |
| 17 | 636 nM |
| 19 | 119 nM |
| 21 | 103 nM |
| 27 | 9000 nM |
| 28 | 1400 nM |
| 29 | 10000 nM |
| 30 | 875 nM |
| 31 | 674 nM |
| 100 | 148 nM |
| 101 | 20 nM |
| 102 | 2.6 nM |
| 103 | 158 nM |
| 104 | >1000 nM |

TABLE 2-continued

Representative in vitro $IC_{50}$ data

| COMPOUND | $IC_{50}$ |
|---|---|
| 105 | >1000 nM |
| 106 | >1000 nM |
| 107 | 193 nM |
| 108 | 218 nM |
| 141 | 94.6 nM |
| 142 | 80 nM, 100 nM |
| 143 | >1 uM |
| 144 | 128 nM |
| 145 | >1 uM |
| 146 | 17 nM, 93 nM |
| 147 | >1000 nM |
| 148 | 55 nM |

Example 7

In Vivo Assays

Treatment of adjuvant arthritis in rats: Adjuvant arthritis (AA) is induced in female Lewis rats by the injection (base of the tail) of 0.1 mL of a 10 mg/mL bacterial suspension made from ground, heat-killed *Mycobacterium tuberculosis* H37Ra suspended in incomplete Freund's adjuvant. Rats are given a test compound orally once a day for 12 days, starting the day following the induction. The development of polyarthritis is monitored daily by macroscopic inspection and assignment of an arthritis index to each animal, during the critical period (days 10 to 25 post-immunization).

The intensity of polyarthritis is scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws is thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index is 16.

Oral administration of compounds of this invention reproducibly reduce the arthritic score and delay the development of polyarthritis in a dose-dependent manner. The arthritis score used in this model is a reflection of the inflammatory state of the structures monitored and the results show the ability of the test compound to provide relief for this aspect of the pathology.

Treatment of Crohn's disease in dinitrobenzene sulfonic acid-induced inflammatory bowel syndrome model rats: Wistar derived male or female rats weighing 200±20 g and fasted for 24 hours are used. Distal colitis is induced by intra-colonic instillation of 2,4-dinitrobenzene sulfonic acid (DNBS, 25 mg in 0.5 mL ethanol 30%) after which air (2 mL) is gently injected through the cannula to ensure that the solution remains in the colon. A test compound and/or vehicle is administered orally 24 and 2 hours before DNBS instillation and then daily for 5 days. One control group is similarly treated with vehicle alone while the other is treated with vehicle plus DNBS. The animals are sacrificed 24 hours after the final dose of test compound administration and each colon is removed and weighed. Colon-to-body weight ratio is then calculated for each animal according to the formula: Colon (g)/BW×100. The "Net" increase in ratio of Vehicle-control+ DNBS group relative to Vehicle-control group is used as a base for comparison with test substance treated groups and expressed as "% Deduction." Compounds of this invention reproducibly have about 30% deduction. A 30% or more reduction in colon-to-body weight ratio, relative to the vehicle treated control group, is considered significant.

Rats treated with test substance orally show a marked reduction in the inflammatory response. These experiments are repeated three times and the effects are reproducible.

Treatment of Crohn's disease in CD4$^+$CD45Rb$^{high}$ T cell-reconstituted SCID colitis model mice: Spleen cells are prepared from normal female BALB/c mice. For cell purification, the following anti-mouse antibodies are used to label non-CD4$^+$ T cells: B220 (RA3-6B2), CD11b (M1/70), and CD8α (53-6.72). All antibodies are obtained from BioSource (Camarillo, Calif.). M450 anti-rat IgG-coated magnetic beads (Dynal, Oslo, Norway) are used to bind the antibodies and negative selection is accomplished using an MPC-1 magnetic concentrator. The enriched CD4$^+$ cells are then labeled for cell sorting with FITC-conjugated CD45RB (16A, Pharmingen, San Diego, Calif.) and PE-conjugated CD4 (CT-CD4, Caltag, Burlingame, Calif.). CD4$^+$ CD45RB$^{high}$ cells are operationally defined as the upper 40% of CD45Rb-staining CD4$^+$ cells and sorted under sterile conditions by flow cytometry. Harvested cells are resuspended at 4×10$^6$/mL in PBS and injected 100 µL intraperitoneally into female C.B-17 SCID mice. Compounds of this invention and/or vehicle are orally administered once a day, 5 days per week, starting the day following the transfer. The transplanted SCID mice are weighed weekly and their clinical condition is monitored.

Colon tissue samples are fixed in 10% buffered formalin and embedded in paraffin. Sections (4 µm) collected from ascending, transverse, and descending colon are cut and stained with hematoxylin and eosin. The severity of colitis is determined based on histological examination of the distal colon sections, whereby the extent of colonic inflammation is graded on a scale of 0-3 in each of four criteria: crypt elongation, cell infiltration, depletion of goblet cells, and the number of crypt abscesses.

LP lymphocytes are isolated from freshly obtained colonic specimens. After removal of payer's patches, the colon is washed in Ca/Mg-free HBSS, cut into 0.5 cm pieces and incubated twice in HBSS containing EDTA (0.75 mM), DTT (1 mM), and antibiotics (amphotericin 2.5 µg/mL, gentamicin 50 µg/mL from Sigma) at 37° C. for 15 min. Next, the tissue is digested further in RPMI containing 0.5 mg/mL collagenase D, 0.01 mg/mL DNase I (Boehringer Manheim), and antibiotics at 37° C. LP cells are then layered on a 40-100% Percoll gradient (Pharmacia, Uppsala, Sweden), and lymphocyte-enriched populations are isolated from the cells at the 40-100% interface.

To measure cytokine production, 48-well plates are coated with 10 µg/mL murine anti-CD3εantibody (145-2C11) in carbonate buffer (PH 9.6) overnight at 4° C. 5×10$^5$ LP cells are cultured in 0.5 ml of complete medium in precoated wells in the presence of 1 µg/mL soluble anti-CD28 antibody (37.51). Purified antibodies are obtained from Pharmingen. Culture supernatants are removed after 48 h and assayed for cytokine production. Murine IFNγ is measured using an ELISA kit from Endogen (Cambridge, Mass.), according to the manufacturer's instructions.

Histological analysis show that oral administration of compounds of this invention reduce colonic inflammation as compared to vehicle control. The suppressive effect is dose-dependent with a substantial reduction at a dose of 10 mg/kg. The calculated colon-to-body weight ratio is consistent with the histological score, showing attenuation by treatment with the test compound. Furthermore, analysis of cytokines from LP cells in response to anti-CD3 antibody and anti-CD28 antibody demonstrate that LP cells from vehicle control produced an augmented level of IFNγ and treatment with test substance greatly diminish the production. These results clearly demonstrate the potential of the test substance in treatment of inflammatory bowel disease represented by Crohn's disease.

All of the features, specific embodiments and particular substituents disclosed herein may be combined in any combination. Each feature, embodiment or substituent disclosed in this specification may be replaced by an alternative feature, embodiment or substituent serving the same, equivalent, or similar purpose. In the case of chemical compounds, specific values can be combined in any combination resulting in a stable structure. Furthermore, specific values (whether preferred or not) for substituents in one type of chemical structure may be combined with values for other substituents (whether preferred or not) in the same or different type of chemical structure. Thus, unless expressly stated otherwise, each feature, embodiment or substituent disclosed is only an example of a generic series of equivalent or similar features feature, embodiments or substituents.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to a heterocyclic compound described in the specification also can be made, screened for their inhibiting IL-12 activities, and used to practice this invention. Thus, other embodiments are also within the claims.

What is claimed is:
1. A compound represented by formula (II):

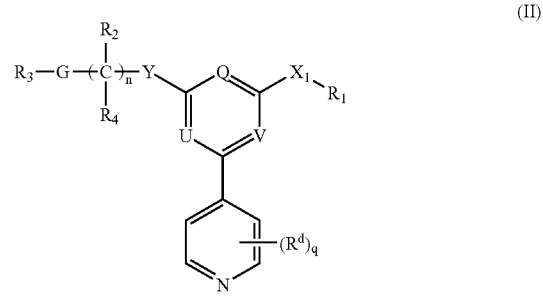

or a pharmaceutically acceptable salt thereof, wherein:
V is N and Q and U are CR$^g$;
X$_1$ is selected from the group consisting of:

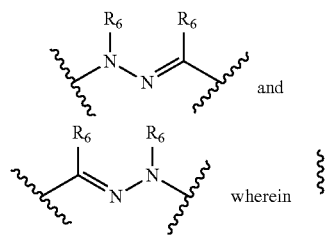

wherein $\{$ represents the point of attachment;
Y is (CH(R$^g$))$_m$, C(O), C(NR), O, S, S(O), S(O)$_2$, N(OR$^k$), N(R$^k$), or absent;

$R_1$ is a substituted or unsubstituted aryl or a substituted or unsubstituted heteroaryl, provided that $R_1$ is not tetrazolyl, o-methoxyphenyl, 3,4,5-trimethoxyphenyl, a substituted or unsubstituted 4,5-dihydro-1H-benzo[g]indazolyl, a substituted 5-oxo-1,2,3,9b-tetrahydro-pyrrolo[2,1-a]isoindolyl;

$R_3$ is $R^g$, —C(O)$R^c$, —OC(O)$R^c$, —SC(O)$R^c$, —N$R^k$C(O)$R^c$, —C(S)$R^c$, —OC(S)$R^c$, —SC(S)$R^c$, —N$R^k$C(S)$R^c$, —C(NR)$R^c$, —OC(NR)$R^c$, —SC(NR)$R^c$, —N$R^k$C(NR)$R^c$, —SO$_2R^c$, —S(O)$R^c$, —N$R^k$SO$_2R^c$, —OS(O)$_2R^c$, —OP(O)$R^cR^c$, or —P(O)$R^cR^c$;

$R_2$ and $R_4$ for each occurrence, are independently, H, an optionally substituted alkyl, an optionally substituted alkylcarbonyl, —O$R^k$, —S$R^k$, —N$R^hR^j$, hydroxylalkyl, —C(O)$R^c$, —OC(O)$R^c$, —SC(O)$R^c$, —N$R^k$C(O)$R^c$, —C(S)$R^c$, —OC(S)$R^c$, —SC(S)$R^c$, —N$R^k$C(S)$R^c$, —C(NR)$R^c$, —OC(NR)$R^c$, —SC(NR)$R^c$, —N$R^k$C(NR)$R^c$, —SO$_2R^c$, —S(O)$R^c$, —N$R^k$SO$_2R^c$, —OS(O)$_2R^c$, —OP(O)$R^cR^c$, —P(O)$R^cR^c$, halo, haloalkyl, aminoalkyl, mercaptoalkyl, cyano, nitro, nitroso, azide, an optionally substituted alkylcarbonylalkyl, an optionally substituted cyclyl, an optionally substituted cycloalkyl, an optionally substituted heterocyclyl, an optionally substituted heterocycloalkyl, an optionally substituted aryl, an optionally substituted aralkyl, an optionally substituted heteroaryl, an optionally substituted heteroaralkyl, or isothionitro; or $R_2$ and $R_4$ taken together are =O, =S, or =NR;

$R_6$ is H or an alkyl;

$R^c$, for each occurrence, is independently, H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl, haloalkyl, —O$R^k$, —S$R^k$, —N$R^hR^j$, hydroxylalkyl, alkylcarbonylalkyl, mercaptoalkyl, aminoalkyl, sulfonylalkyl, sulfonylaryl, or thioalkoxy;

$R^d$, for each occurrence, is independently, H or a halo;

$R^g$, for each occurrence, is independently, H;

$R^h$ and $R^j$, for each occurrence, are independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl; or $R^h$ and $R^j$ taken together with the N to which they are attached is an optionally substituted heterocyclyl, an optionally substituted heterocycloalkyl, or an optionally substituted heteroaryl;

$R^k$, for each occurrence, is independently H, an optionally substituted alkyl, an optionally substituted alkenyl, an optionally substituted alkynyl, an optionally substituted cyclyl, an optionally substituted cycloalkyl, an optionally substituted heterocyclyl, an optionally substituted heterocycloalkyl, an optionally substituted aralkyl, an optionally substituted heteroaralkyl, an optionally substituted aryl, an optionally substituted heteroaryl;

G is a Hydrazide; Hydrazone; Hydrazine; Hydroxylamine; Oxime; Amide; Ester; Carbonate; Carbamate; Thiocarbamate; —N$R^k$—C(NR)—N$R^k$; —N$R^k$—C(O)—N$R^k$—; —N$R^k$—C(S)—N$R^k$—; —N$R^k$—S(O)$_2$—N$R^k$—; Phosphoryl; an optionally substituted -Cyclyl-; an optionally substituted -Heterocyclyl-; an optionally substituted -Aryl-; an optionally substituted -Heteroaryl-; an optionally substituted -Heteroarylalkyl-; an optionally substituted -Heteroaryl—N$R^k$-; an optionally substituted -Heteroaryl-S—; an optionally substituted -Heteroarylalkyl-O—; —Si(O$R^k$)$_2$—; —B(O$R^k$)—; —C(NR)—N$R^k$—; —N($R^k$)—CR$^g$R$^g$—C(O)—; —C(O)—ON($R^k$)—; —C(O)—N($R^k$)O—; —C(S)—ON($R^k$)—; —C(S)—N($R^k$)O—; —C(N($R^k$))—ON($R^k$)—; —C(N($R^k$))—N$R^k$O—; —OS(O)$_2$—N($R^k$)N($R^k$)—; —OC(O)—N($R^k$)N($R^k$)—; —OC(S)—N($R^k$)N($R^k$)—; —OC(N($R^k$))—N($R^k$)N($R^k$)—; —N($R^k$)N($R^k$)S(O)$_2$O—; —N($R^k$)N($R^k$)C(S)O—; —N($R^k$)N($R^k$)C(N($R^k$))O—; —OP(O)($R^c$)O—; —N($R^k$)P(O)($R^c$)O—; —OP(O)($R^c$)N($R^k$)—; —N($R^k$)P(O)($R^c$)N($R^k$)—; —P(O)($R^c$)O—; —P(O)($R^c$)N($R^k$)—; —N($R^k$)P(O)($R^c$)—; —OP(O)($R^c$)—; —O-alkyl-heterocyclyl-N($R^k$)—; —N($R^k$)CHR$^g$C(O)N($R^k$)CHR$^g$C(O)—; —N($R^k$)CHR$^g$C(O)—; —N($R^k$)C(O)CHR$^g$—; or —C(O)N($R^k$)CHR$^g$C(O)—; each of which is optionally substituted; or G is absent;

q is 0, 1, 2, 3, or 4;

m, for each occurrence, is independently 1, 2, 3, 4, 5, 6, 7, or 8;

n, for each occurrence, is independently 0, 1, 2, 3, 4, 5, 6, or 7; and p, for each occurrence, is independently 0, 1, or 2.

2. The compound of claim 1, wherein $R_1$ is an optionally substituted naphthyl, an optionally substituted anthracenyl, an optionally substituted indanyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl; or $R_1$ is a phenyl group which is optionally substituted with one or more substituents selected from the group consisting of a halo, hydroxyl, amino, alkylamino, arylamino, dialkylamino, diarylamino, cyano, nitro, mercapto, mercapto, imino, formyl, carbamido, carbamyl, carboxyl, thioureido, thiocyanato, sulfoamido, sulfonylalkyl, sulfonylaryl, alkyl, alkenyl, alkynyl, cycloalkyl, cyclyl, aryl, aralkyl, heterocycloalkyl, heterocyclyl, heteroaryl, heteroaralkyl, haloalkyl, aryloxy, hydroxyl, hydroxylalkyl, alkylcarbonyl, alkylcarbonylalkyl, alkoxycarbonyl, alkylcarbonyloxy, aryloxycarbonyl, heteroaryloxy, heteroaryloxycarbonyl, mercaptoalkyl, arylsulfonyl, aminoalkyl, alkylcarbonylamino, alkylaminocarbonyl, alkoxycarbonylamino, arylamino-substituted aryl, arylalkylamino, aralkylaminocarbonyl, amido, alkylaminosulfonyl, arylaminosulfonyl, dialkylaminosulfonyl, alkylsulfonylamino, arylsulfonylamino, mercaptoalkoxy, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $B(OH)_2$, $P(O)(OR^{15})_2$, $S(O)R^{17}$, or $S(O)_2R^{17}$, wherein each alkyl, alkenyl, alkynyl, cycloalkyl, cyclyl, aryl, aralkyl, heterocycloalkyl, heterocyclyl, heteroaryl, or heteroaralkyl, of each phenyl substituent of $R_1$ may be optionally substituted with alkyl, aryl, heteroaryl, halogen, hydroxyl, amino, mercapto, cyano, nitro, oxo (=O), thioxo (=S), or imino (=NR);

$R^{15}$ is independently hydrogen, $C_1$-$C_6$ alkyl optionally substituted with cycloalkyl, aryl, heterocyclyl, or heteroaryl;

$R^{16}$ is independently hydrogen, $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl; and $R^{17}$ is independently $C_3$-$C_6$ cycloalkyl, aryl, heterocyclyl, heteroaryl, $C_1$-$C_4$ alkyl or $C_1$-$C_4$ alkyl substituted with $C_3$-$C_6$ cycloalkyl, aryl, heterocyclyl or heteroaryl;

wherein each $C_3$-$C_6$ cycloalkyl, aryl, heterocyclyl, heteroaryl and $C_1$-$C_4$ alkyl in each $R^{15}$, $R^{16}$ and $R^{17}$ can optionally be substituted with halo, CN, $C_1$-$C_4$ alkyl, OH, $C_1$-$C_4$ alkoxy, COOH, C(O)O$C_1$-$C_4$ alkyl, $NH_2$, $C_1$-$C_4$ alkylamino, or $C_1$-$C_4$ dialkylamino.

3. The compound of claim 2, wherein $R_1$ is an optionally substituted indanyl, an optionally substituted indolyl, an optionally substituted thienyl, an optionally substituted 2,3,4,9-tetrahydro-1H-carbazolyl.

4. The compound of claim 3, wherein $R_1$ is 2,3-dimethyl-1H-indol-5-yl, 4,5-dimethyl-thien-2-yl, or 2,3,4,9-tetrahydro-1H-carbazol-6-yl.

5. The compound of claim 1, wherein $X_1$ is a group represented by the following formula:

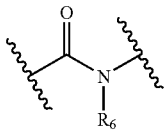

6. The compound of claim 2, wherein Y is $(CH(R^g))_m$, O, $N(OR^k)$, $NR^k$, or absent.

7. The compound of claim 6, wherein Y is $NR^k$ and $R^k$ is H or a lower alkyl.

8. The compound of claim 6, wherein each of $R_2$ and $R_4$ is independently, H or an alkyl.

9. The compound of claim 6, wherein $R_3$ is H, an optionally substituted alkyl, an optionally substituted aryl, an optionally substituted heteroaryl, an optionally substituted cycloalkyl, an optionally substituted cyclyl, an optionally substituted heterocycloalkyl, an optionally substituted heterocyclyl, cyano, halo, $OR^k$, or $NR^hR^j$.

10. The compound of claim 9, wherein $R_3$ is —$OR^k$ or —$NR^hR^j$, and $R^f$, $R^h$ and $R^j$ are each, independently, H or alkyl.

11. The compound of claim 6, wherein n is 0, 1, 2, or 3.

12. The compound of claim 6, wherein G is —C(O)NHNH—, —NHNHC(O)—, —C(O)$NR^kNR^k$—, —$NR^kN$-$R^kC(O)$—, —CH=N—NH—, —NH—N=CH—CR$^g$=N—$NR^k$—, —$NR^k$—N=CR$^g$—, —NHNH—, —$NR^kNR^k$—, —NHO—, —O—NH—, —O—$NR^k$—, —$NR^k$—O—, —CH=N—O—, —O—N=CH—, —CR$^g$=N—O—, —O—N=CR$^g$—, —O—C(O)—NH—, —O—C(O)—$NR^k$—, —O—C(S)—NH—, —NH—C(S)—O—, —O—C(S)—$NR^k$—, —$NR^k$—C(S)—O—, —NH—C(NH)—NH—, —$NR^k$—C(NH)—NH—, —$NR^k$—C(NR)—NH—, —NH—C(N(CN))—NH—, —NH—C($NSO_2R^c$)—NH—, —$NR^k$—C($NSO_2R^c$)—NH—, —NH—C($NNO_2$)—NH—, —NH—C(NC(O)$R^c$)—NH—, —NH—C(O)—NH—, —$NR^k$—C(O)—$NR^k$—, —NH—C(S)—NH— and —$NR^k$—C(S)—$NR^k$—, —NH—S(O)$_2$—NH—, —$NR^k$—S(O)$_2$—$NR^k$—, —$NR^k$—S(O)$_2$—O—, —P(O)($R^c$)—, —P(O)($R^c$)—O—, —P(O)($R^c$)—$NR^k$—, -Cyclyl-, -Heterocyclyl-, -Aryl-, -Heteroaryl-, -Heteroarylalkyl-, -Heteroaryl-NH—, -Heteroaryl-S-, -Heteroarylalkyl-O—, —C(N=CN)—NH—, —Si(OH)$_2$—, —B(OH)—, —C(NH)—$NR^k$—, —$NR^k$—CH$_2$—C(O)—, —C(O)—$ONR^k$—, —C(O)—$NR^kO$—, —C(S)—$ONR^k$—, —C(S)—$NR^kO$—, —C(NR)—$ONR^k$—, —C(NR)—$NR^kO$—, —$OS(O)_2$—$NR^kNR^k$—, —OC(O)—$NR^kNR^k$—, —OC(S)—$NR^kNR^k$—, —OC(NR)—$NR^kNR^k$—, —$NR^kNR^kS(O)_2O$—, —$NR^k$N-$R^kC(S)O$—, —$NR^kNR^kC(NR)O$—, —OP(O)($R^c$)O—, —$NR^kP(O)(R^c)O$—, —OP(O)($R^c$)N($R^k$)—, —$NR^kP(O)(R^c)N(R^k)$—, —P(O)($R^c$)O—, —P(O)($R^c$)$NR^k$—, —$NR^kP(O)(R^c)$—, —OP(O)($R^c$)—, —O-alkyl-heterocyclyl-N($R^c$)—, —$NR^kCHR^gC(O)NR^kCHR^gC(O)$—, —$NR^gCHR^gC(O)$—, —$NR^kC(O)CHR^g$—, —C(O)$NR^kCHR^gC(O)$—, or absent.

13. The compound of claim 6, wherein G is absent.

14. A compound selected from the group consisting of:
(1) Diisopropyl-{4-methoxy-6-[N'-(1-methyl-1H-indol-3-ylmethylene)-hydrazino]-[1,3,5]triazin-2-yl}-amine;
(2) {4-[N'-(1H-Indol-3-ylmethylene)-hydrazino]-6-methoxy-[1,3,5]triazin-2-yl}-diisopropyl-amine;
(3) Diisopropyl-{4-methoxy-6-[N'-(7-methyl-1H-indol-3-ylmethylene)-hydrazino]-[1,3,5]triazin-2-yl}-amine;
(4) {4[N'-(5-Fluoro-1H-indol-3-ylmethylene)-hydrazino]-6-methoxy-[1,3,5]triazin-2-yl}-diisopropylamine;
(5) 1-{3-[(4-Diisopropylamino-6-methoxy-[1,3,5]triazin-2-yl)-hydrazonomethyl]-indol -1-yl}-ethanone;
(6) [4-[N'-(1H-Indol)-3-ylmethylene)-hydrazino]-6-(2-pyridin-2-yl-ethoxy)-[1,3,5]triazin-2-ylamino]-acetic acid methyl ester;
(7) N-{4-[2-(3,4-Dimethoxy-phenyl)-ethoxy]-6-thiazolidin-3-yl[1,3,5]triazin-2-yl}-N'-(1H-indol-3-ylmethylene)-hydrazine;
(8) N-[4-(1,4-Dioxa-8-aza-spiro[4.5]dec-8-yl)-6-(2-pyridin-2-yl-ethoxy)-[1,3,5]triazin-2-yl]-N'-(1H-indol-3-ylmethylene)-hydrazine;
(9) [4-[N'-(1H-Indol-3-ylmethylene)-hydrazino]-6-(2-pyridin-2-yl-ethoxy)-[1,3,5]triazin-2-ylamino]-acetonitrile;
(10) N-(1H-Indol-3-ylmethylene)-N'-[4-(2-pyridin-2-yl-ethoxy)-6-(tetrahydro-pyran-4-yloxy)-[1,3,5]triazin-2-yl]-hydrazine;
(11) 1-[4-[N'-(1H-Indol-3-ylmethylene)-hydrazino]-6-(2-pyridin-2-yl-ethoxy)-[1,3,5]triazin-2-yl]-piperidin-4-one;

(12) N-(3-Methyl-benzylidene)-N'-[6-piperidin-1-yl-2-(2-pyridin-2-yl-ethoxy)-pyrimidin-4-yl]-hydrazine;
(13) Bis-(2-methoxy-ethyl)-[6-[N'-(3-methyl-benzylidene)-hydrazino]-2-(2-pyridin-2-yl-ethoxy)-pyrimidin-4-yl]-amine;
(14) [2-(3,4-Dimethoxy-phenyl)-ethyl]-{4-methyl-6-[N'-(3-methyl-benzylidene)-hydrazino]-pyrimidin-2-yl}-amine;
(15) {2-[2-(3,4-Dimethoxy-phenyl)-ethoxy]-6-[N'-(3-methyl-benzylidene)-hydrazino]-pyrimidin-4-yl}-dimethyl-amine;
(16) {6-[2-(3,4-Dimethoxy-phenyl)-ethoxy]-2-[N'-(3-methyl-benzylidene)-hydrazino]-pyrimidin-4-yl}-dimethyl-amine;
(17) [2-(3,4-Dimethoxy-phenyl)-ethyl]-{4-[N'-(3-methyl-benzylidene)-hydrazino]-pyrimidin-2-yl}-amine;
(18) Dimethyl-[2-[N'-(3-methyl-benzylidene)-hydrazino]-6-(2-morpholin-4-yl-ethoxy)-pyridin-4-yl]-amine;
(19) 2,6-Bis-[N'-(3-methyl-benzylidene)-hydrazino]-pyrimidin-4-ylamine;
(20) N-{4-[2-(3,4-Dimethoxy-phenyl)-ethoxy]-6-thiophen-3-yl-[1,3,5]triazin-2-yl}-N'-isopropylidene-hydrazine;
(21) N-{4-[2-(3,4-Dimethoxy-phenyl)-ethoxy]-6-imidazol-1-yl-[1,3,5]triazin-2-yl}-N'-(3-methyl-benzylidene)-hydrazine;
(22) N-{4-Chloro-6-[2-(3,4-dimethoxy-phenyl)-ethoxy]-[1,3,5]triazin-2-yl}-N'-(3-methyl-benzylidene)-hydrazine;
(23) N-{4-[2-(3,4-Dimethoxy-phenyl)-ethoxy]-6-phenyl-[1,3,5]triazin-2-yl}-N'-(3-methyl-benzylidene)-hydrazine;
(24) N-{4-[2-(3,4-Dimethoxy-phenyl)-ethoxy]-6-thiophen-3-yl-[1,3,5]triazin-2-yl}-N'-(3-methyl-benzylidene)-hydrazine;
(25) N-(3-Methyl-benzylidene)-N'-[2-(2-pyridin-2-yl-ethoxy)-6-pyrrolidin-1-yl-pyrimidin-4-yl]-hydrazine;
(26) N-[6-Azetidin-1-yl-2-(2-pyridin-2-yl-ethoxy)-pyrimidin-4-yl]-N'-(3-methyl-benzylidene)-hydrazine;
(27) 3-{6-Dimethylamino-2-[N'-(3-methyl-benzylidene)-hydrazino]-pyrimidin-4-yl}-propan-1-ol;
(28) (4-Nitro-phenyl)-carbamic acid 3-{6-dimethylamino-2-[N'-(3-methyl-benzylidene)-hydrazino]-pyrimidin-4-yl}-propyl ester;
(29) (4-Trifluoromethyl-phenyl)-carbamic acid 3-{6-dimethylamino-2-[N'-(3-methyl-benzylidene)-hydrazino]-pyrimidin-4-yl}-propyl ester;
(30) Diethyl-[6-[N'-(3-methyl-benzylidene)-hydrazino]-2-(2-morpholin-4-yl-ethoxy)-pyrimidin-4-yl]-amine;
(31) (2-Methoxy-ethyl)-methyl-[6-[N'-(3-methyl-benzylidene)-hydrazino]-2-(2-morpholin-4-yl-ethoxy)-pyrimidin-4-yl]-amine;
(32) 6-(2,3-Dimethyl-1H-indol-5-ylamino)-2-(2-morpholin-4-yl-ethoxy)-pyrimidine-4-carboxylic acid methyl ester;
(33) 6-(2,3-Dimethyl-1H-indol-5-ylamino)-2-(2-morpholin-4-yl-ethoxy)-pyrimidine-4-carboxylic acid dimethylamide;
(34) [6-(2,3-Dimethyl-1H-indol-5-ylamino)-2-(2-morpholin-4-yl-ethoxy)-pyrimidin-4-yl]-morpholin-4-yl-methanone;
(35) 4-(2,3-Dimethyl-1H-indol-5-ylamino)-6-(2-morpholin-4-yl-ethoxy)-pyrimidine-2-carboxylic acid methyl ester;
(36) N-(1H-Indol-3-ylmethylene)-N'-[2-(2-pyridin-2-yl-ethoxy)-6-thiazolidin-3-yl-pyrimidin-4-yl]-hydrazine;
(37) N-(1H-Indol-3-ylmethylene)-N'-[2-(2-morpholin-4-yl-ethoxy)-6-thiazolidin-3-yl-pyrimidin-4-yl]-hydrazine;
(38) N-(3-Methyl-benzylidene)-N'-[2-(2-morpholin-4-yl-ethoxy)-6-thiazolidin-3-yl-pyrimidin-4-yl]-hydrazine;
(39) 3-(2-{4-[N'-(3-Methyl-benzylidene)-hydrazino]-6-thiazolidin-3-yl-pyrimidin-2-yloxy}-ethyl)-oxazolidin-2-one;
(40) 4-Methyl-2-{[2-(2-methylamino-ethoxy)-6-thiazolidin-3-yl-pyrimidin-4-yl]-hydrazonomethyl}-phenol;
(41) N-(3-Methyl-benzylidene)-N'-[6-(2-morpholin-4-yl-ethoxy)-4-thiazolidin-3-yl-pyridin-2-yl]-hydrazine;
(42) N-(3-Methyl-benzylidene)-N'-[2-(2-morpholin-4-yl-ethoxy)-6-thiazolidin-3-yl-pyridin-4-yl]-hydrazine;
(43) (2,3-Dimethyl-1H-indol-6-yl)-[2-(2-morpholin-4-yl-ethoxy)-6-thiazolidin-3-yl-pyrimidin-4-yl]-amine;
(44) 2-(2-Morpholin-4-yl-ethoxy)-6-thiazolidin-3-yl-pyrimidine-4-carboxylic acid (2,3-dimethyl-1H-indol-5-yl)-amide;
(45) 3-(2-{4-Diethylamino-6-[N'-(3-methyl-benzylidene)-hydrazino]-pyrimidin-2-yloxy}-ethyl)-oxazolidin-2-one;
(46) Diethyl-{2-(2-methylamino-ethoxy)-6-[N'-(3-methyl-benzylidene)-hydrazino]-pyrimidin-4-yl}-amine;
(47) 1-{4-Diethylamino-6-[N'-(3-methyl-benzylidene)-hydrazino]-pyrimidin-2-yloxy}-2-methyl-propan-2-ol;
(48) Diethyl-[6[N'-(3-methyl-benzylidene)-hydrazino]-2-(2-pyridin-2-yl-ethoxy)-pyrimidin-4-yl]-amine;
(49) 2-{[6-Diethylamino-2-(2-morpholin-4-yl-ethoxy)-pyrimidin-4-yl]-hydrazonomethyl}-4-methyl-phenol;
(50) Diethyl-[6-[N'-(1H-indol-3-ylmethylene)-hydrazino]-2-(2-morpholin-4-yl-ethoxy)-pyrimidin-4-yl]-amine;
(51) Diethyl-[4-[N'-(3-methyl-benzylidene)-hydrazino]-6-(2-morpholin-4-yl-ethoxy)-[1,3,5]triazin-2-yl]-amine;
(52) Diethyl-[2-[N'-(3-methyl-benzylidene)-hydrazino]-6-(2-morpholin-4-yl-ethoxy)-pyridin-4-yl]-amine;
(53) Diethyl-[6-[N'-(3-methyl-benzylidene)-hydrazino]-4-(2-morpholin-4-yl-ethoxy)-pyridin-2-yl]-amine;
(54) 6-Diethylamino-2-(2-morpholin-4-yl-ethoxy)-pyrimidine-4-carboxylic acid (2,3-imethyl-1H-indol-5-yl)-amide;
(55) 6-Diethylamino-2-(2-morpholin-4-yl-ethoxy)-4-[(2,3-dimethy-1H-indol-5-yl)-amino]-pyrimidine;
(56) 3-(2-{4-[(2-Methoxy-ethyl)-methyl-amino]-6-[N'-(3-methyl-benzylidene)-hydrazino]-pyrimidin-2-yloxyl}-ethyl)-oxazolidin-2-one;
(57) (2-Methoxy-ethyl)-methyl-{2-(2-methylamino-ethoxy)-6-[N'-(3-methyl-benzylidene)-hydrazino]-pyrimidin-4-yl}-amine;
(58) 1-{4-[(2-Methoxy-ethyl)-methyl-amino]-6-[N'-(3-methyl-benzylidene)-hydrazino]-pyrimidin-2-yloxy}-2-methyl-propan-2-ol;
(59) (2-Methoxy-ethyl)-methyl-[4-[N'-(3-methyl-benzylidene)-hydrazino]-6-(2-morpholin-4-yl-ethoxy)-[1,3,5]triazin-2-yl]-amine;
(60) (2-Methoxy-ethyl)-methyl-[2-[N'-(3-methyl-benzylidene)-hydrazino]-6-(2-morpholin-4-yl-ethoxy)-pyridin-4-yl]-amine;
(61) (2-Methoxy-ethyl)-methyl-[6-[N'-(3-methyl-benzylidene)-hydrazino]-4-(2-morpholin-4-yl-ethoxy)-pyridin-2-yl]-amine;
(62) 2-{[6-[(2-Methoxy-ethyl)-methyl-amino]-2-(2-morpholin-4-yl-ethoxy)-pyrimidin-4-yl]-hydrazonomethyl}-4-methyl-phenol;

(63) [6-[N'-(1H-Indol-3-ylmethylene)-hydrazino]-2-(2-morpholin-4-yl-ethoxy)-pyrimidin-4-yl]-(2-methoxy-ethyl)-methyl-amine;
(64) 4-[(2-Methoxy-ethyl)-methyl-amino]-6-(2-morpholin-4-yl-ethoxy)-[1,3,5]triazine-2-carboxylic acid (2,3-dimethyl-1H-indol-5-yl)-amide;
(65) N-(2,3-Dimethyl-1H-indol-5-yl)-N'-(2-methoxy-ethyl)-N'-methyl-6-(2-morpholin-4-yl-ethoxy)-[1,3,5]triazine-2,4-diamine;
(66) Dimethyl-[6-[N'-(3-methyl-benzylidene)-hydrazino]-2-(2-morpholin-4-yl-ethoxy)-pyrimidin-4-yl]-amine;
(67) 3-(2-{4-Dimethylamino-6-[N'-(3-methyl-benzylidene)-hydrazino]-pyrimidin-2-yloxy}-ethyl)-oxazolidin-2-one;
(68) Dimethyl-{2-(2-methylamino-ethoxy)-6-[N'-(3-methyl-benzylidene)-hydrazino]-pyrimidin-4-yl}-amine;
(69) 1-{4-Dimethylamino-6-[N'-(3-methyl-benzylidene)-hydrazino]-pyrimidin-2-yloxy}-2-methyl-propan-2-ol;
(70) Dimethyl-[6[N'-(3-methyl-benzylidene)-hydrazino]-2-(2-pyridin-2-yl-ethoxy)-pyrimidin-4-yl]-amine;
(71) 2-{[6-Dimethylamino-2-(2-morpholin-4-yl-ethoxy)-pyrimidin-4-yl]-hydrazonomethyl}-4-methyl-phenol;
(72) [6-[N'-(2-Amino-5-methyl-benzylidene)-hydrazino]-2-(2-morpholin-4-yl-ethoxy)-pyrimidin-4-yl]-dimethyl-amine;
(73) [6-[N'-(1H-Indol-3-ylmethylene)-hydrazino]-2-(2-morpholin-4-yl-ethoxy)-pyrimidin-4-yl]-dimethyl-amine;
(74) Dimethyl-[4-[N'-(3-methyl-benzylidene)-hydrazino]-6-(2-morpholin-4-yl-ethoxy)-[1,3,5]triazin-2-yl]-amine;
(75) Dimethyl-[6-[N'-(3-methyl-benzylidene)-hydrazino]-4-(2-morpholin-4-yl-ethoxy)-pyridin-2-yl]-amine;
(76) 6-Dimethylamino-2-(2-morpholin-4-yl-ethoxy)-pyrimidine-4-carboxylic acid (2,3-dimethyl-1H-indol-5-yl)-amide;
(77) 6-Dimethylamino-2-(2-morpholin-4-yl-ethoxy)-4-[(2,3-dimethyl-1H-indol-5-yl)-amino] pyrimidine;
(78) 6-[N'-(3-Methyl-benzylidene)-hydrazino]-2-(2-morpholin-4-yl-ethoxy)-pyrimidin-4-ylamine;
(79) 3-(2-{4-Amino-6-[N'-(3-methyl-benzylidene)-hydrazino]-pyrimidin-2-yloxy}-ethyl)-oxazolidin-2-one;
(80) 2-(2-Methylamino-ethoxy)-6-[N'-(3-methyl-benzylidene)-hydrazino]-pyrimidin-4-ylamine;
(81) 6-[N'-(3-Methyl-benzylidene)-hydrazino]-2-(2-pyridin-2-yl-ethoxy)-pyrimidin-4-ylamine;
(82) 2-{[6-Amino-2-(2-morpholin-4-yl-ethoxy)-pyrimidin-4-yl]-hydrazonomethyl}-4-methyl-phenol;
(83) 6-[N'-(2-Amino-5-methyl-benzylidene)-hydrazino]-2-(2-morpholin-4-yl-ethoxy)-pyrimidin-4-ylamine;
(84) 6-[N'-(1H-Indol-3-ylmethylene)-hydrazino]-2-(2-morpholin-4-yl-ethoxy)-pyrimidin-4-ylamine;
(85) 1-{4-Amino-6-[N'-(3-methyl-benzylidene)-hydrazino]-pyrimidin-2-yloxy}-2-methyl-propan-2-ol;
(86) 2-[N'-(3-Methyl-benzylidene)-hydrazino]-6-(2-morpholin-4-yl-ethoxy)-pyridin-4-ylamine;
(87) 6-[N'-(3-Methyl-benzylidene)-hydrazino]-4-(2-morpholin-4-yl-ethoxy)-pyridin-2-ylamine;
(88) 4-[N'-(3-Methyl-benzylidene)-hydrazino]-6-(2-morpholin-4-yl-ethoxy)-[1,3,5]triazin-2-ylamine;
(89) 2-Amino-6-(2-morpholin-4-yl-ethoxy)-pyrimidine-4-carboxylic acid (2,3-dimethyl-1H-indol-5-yl)-amide;
(90) N4-(2,3-Dimethyl-1H-indol-5-yl)-6-(2-morpholin-4-yl-ethoxy)-pyrimidine-2,4-diamine;
(91) N-[4-Imidazol-1-yl-6-(2-morpholin-4-yl-ethoxy)-[1,3,5]triazin-2-yl]-N'-(3-methyl-benzylidene)-hydrazine;
(92) 3-(2-{4-Imidazol-1-yl-6-[N'-(3-methyl-benzylidene)-hydrazino]-pyrimidin-2-yloxy}-ethyl)-oxazolidin-2-one;
(93) (2-{4-Imidazol-1-yl-6-[N'-(3-methyl-benzylidene)-hydrazino]-pyrimidin-2-yloxy}-ethyl)-methyl-amine;
(94) 1-{4-Imidazol-1-yl-6-[N'-(3-methyl-benzylidene)-hydrazino]-pyrimidin-2-yloxy}-2-methyl-propan-2-ol;
(95) N-[4-Imidazol-1-yl-6-(2-morpholin-4-yl-ethoxy)-pyridin-2-yl]-N'-(3-methyl-benzylidene)-hydrazine;
(96) 2-{[6-Imidazol-1-yl-2-(2-morpholin-4-yl-ethoxy)-pyrimidin-4-yl]-hydrazonomethyl}-4-methyl-phenol;
(97) N-[6-Imidazol-1-yl-2-(2-morpholin-4-yl-ethoxy)-pyrimidin-4-yl]-N'-(1H-indol-3-ylmethylene)-hydrazine;
(98) 2-Imidazol-1-yl-6-(2-morpholin-4-yl-ethoxy)-pyrimidine-4-carboxylic acid (2,3-dimethyl-1H-indol-5-yl)-amide;
(99) (2,3-Dimethyl-1H-indol-5-yl)-[2-imidazol-1-yl-6-(2-morpholin-4-yl-ethoxy)-pyrimidin-4-yl]-amine;
(100) 1-[2,4']Bipyridinyl-6-yl-3-indan-5-yl-urea;
(101) 4-(2-Morpholin-4-yl-ethoxy)-[2,4']bipyridinyl-6-carboxylic acid (2,3-dimethyl-1H-indol-5-yl)-amide;
(102) 4-[(2-Methoxy-ethyl)-methyl-amino]-[2,4']bipyridinyl-6-carboxylic acid (2,3-dimethyl-1H-indol-5-yl)-amide;
(103) 3'-Fluoro-[2,4']bipyridinyl-6-carboxylic acid (2,3-dimethyl-1H-indol-5-yl)-amide;
(104) 6-Pyrimidin-5-yl-pyridine-2-carboxylic acid (2,3-dimethyl-1H-indol-5-yl)-amide;
(105) 6-Thiophen-3-yl-pyridine-2-carboxylic acid (2,3-dimethyl-1H-indol-5-yl)-amide;
(106) [2,3']Bipyridinyl-6-carboxylic acid (2,3-dimethyl-1H-indol-5-yl)-amide;
(107) 2'-Fluoro-[2,4']bipyridinyl-6-carboxylic acid (2,3-dimethyl-1H-indol-5-yl)-amide;
(108) 6-(1H-Pyrazol-4-yl)-pyridine-2-carboxylic acid (2,3-dimethyl-1H-indol-5-yl)-amide;
(109) (E)-4-(2-(4-(2-(3-methylbenzylidene)hydrazinyl)-6-(pyridin-4-yl)pyrimidin-2-yloxy)ethyl)morpholine;
(110) (E)-4-methyl-2-((2-(2-(2-morpholinoethoxy)-6-(pyridin-4-yl)pyrimidin-4-yl)hydrazono)methyl)phenol;
(111) (E)-4-(2-(4-(2-(3,4-dimethylbenzylidene)hydrazinyl)-6-(pyridin-4-yl)pyrimidin-2-yloxy)ethyl)morpholine;
(112) (E)-4-(2-(4-(2-((4,5-dimethylthiophen-2-yl)methylene)hydrazinyl)-6-(pyridin-4-yl)pyrimidin-2-yloxy)ethyl)morpholine;
(113) (E)-N-(2-methoxyethyl)-N-methyl-4-(2-(3-methylbenzylidene)hydrazinyl)-6-(pyridin-4-yl)pyrimidin-2-amine;
(114) (E)-2-((2-(2-((2-methoxyethyl)(methyl)amino)-6-(pyridin-4-yl)pyrimidin-4-yl)hydrazono)methyl)-4-methylphenol;
(115) (E)-4-(2-(3,4-dimethylbenzylidene)hydrazinyl)-N-(2-methoxyethyl)-N-methyl-6-(pyridin-4-yl)pyrimidin-2-amine;
(116) (E)-4-(2-((4,5-dimethylthiophen-2-yl)methylene)hydrazinyl)-N-(2-methoxyethyl)-N-methyl-6-(pyridin-4-yl)pyrimidin-2-amine;
(117) (E)-2-(methyl(4-(2-(3-methylbenzylidene)hydrazinyl)-6-(pyridin-4-yl)pyrimidin-2-yl)amino)ethanol;
(118) (E)-2-((4-(2-(3,4-dimethylbenzylidene)hydrazinyl)-6-(pyridin-4-yl)pyrimidin-2-yl)(methyl)amino)ethanol;

(119) (E)-2-((2-(2-((2-hydroxyethyl)(methyl)amino)-6-(pyridin-4-yl)pyrimidin-4-yl)hydrazono)methyl)-4-methylphenol;
(120) (E)-2-((4-(2-((4,5-dimethylthiophen-2-yl)methylene)hydrazinyl)-6-(pyridin-4-yl)pyrimidin-2-yl)(methyl)amino)ethanol;
(121) (E)-O-methyl-N-(4-(2-(3-methylbenzylidene)hydrazinyl)-6-(pyridin-4-yl)pyrimidin-2-yl)hydroxylamine;
(122) (E)-N-(4-(2-(3,4-dimethylbenzylidene)hydrazinyl)-6-(pyridin-4-yl)pyrimidin-2-yl)-O-methylhydroxylamine;
(123) (E)-2-((2-(2-(methoxyamino)-6-(pyridin-4-yl)pyrimidin-4-yl)hydrazono) methyl)-4-methylphenol;
(124) (E)-N-(4-(2-((4,5-dimethylthiophen-2-yl)methylene)hydrazinyl)-6-(pyridin-4-yl)pyrimidin-2-yl)-O-methylhydroxylamine;
(125) (E)-4-(2-(3-methylbenzylidene)hydrazinyl)-2-(2-(pyridin-2-yl)ethoxy)-6-(pyridin-4-yl)pyrimidine;
(126) (E)-4-(2-(3,4-dimethylbenzylidene)hydrazinyl)-2-(2-(pyridin-2-yl)ethoxy)-6-(pyridin-4-yl)pyrimidine;
(127) (E)-4-methyl-2-((2-(2-(2-(pyridin-2-yl)ethoxy)-6-(pyridin-4-yl)pyrimidin-4-yl)hydrazono)methyl)phenol;
(128) (E)-4-(2-((4,5-dimethylthiophen-2-yl)methylene)hydrazinyl)-2-(2-(pyridin-2-yl)ethoxy)-6-(pyridin-4-yl)pyrimidine;
(129) (E)-4-(2-(4-(2-(3-methylbenzylidene)hydrazinyl)-6-(pyridin-4-yl)-1,3,5-triazin-2-yloxy)ethyl)morpholine;
(130) (E)-4-(2-(4-(2-((4,5-dimethylthiophen-2-yl)methylene)hydrazinyl)-6-(pyridin-4-yl)-1,3,5-triazin-2-yloxy)ethyl)morpholine;
(131) (E)-N-(2-methoxyethyl)-N-methyl-4-(2-(3-methylbenzylidene)hydrazinyl)-6-(pyridin-4-yl)-1,3,5-triazin-2-amine;
(132) (E)-4-(2-((4,5-dimethylthiophen-2-yl)methylene)hydrazinyl)-N-(2-methoxyethyl)-N-methyl-6-(pyridin-4-yl)-1,3,5-triazin-2-amine;
(133) (E)-O-methyl-N-(4-(2-(3-methylbenzylidene)hydrazinyl)-6-(pyridin-4-yl)-1,3,5-triazin-2-yl)hydroxylamine;
(134) (E)-N-(4-(2-((4,5-dimethylthiophen-2-yl)methylene)hydrazinyl)-6-(pyridin-4-yl)-1,3,5-triazin-2-yl)-O-methylhydroxylamine;
(135) (E)-4-(2-(6-(2-(3-methylbenzylidene)hydrazinyl)-4,4'-bipyridin-2-yloxy)ethyl)morpholine;
(136) (E)-4-(2-(6-(2-((4,5-dimethylthiophen-2-yl)methylene)hydrazinyl)-4,4'-bipyridin-2-yloxy)ethyl)morpholine;
(137) (E)-2-(methyl(6-(2-(3-methylbenzylidene)hydrazinyl)-4,4'-bipyridin-2-yl)amino)ethanol;
(138) (E)-2-((6-(2-(3,4-dimethylbenzylidene)hydrazinyl)-4,4'-bipyridin-2-yl)(methyl)amino)ethanol;
(139) (E)-6-(2-((4,5-dimethylthiophen-2-yl)methylene)hydrazinyl)-N-(2-methoxyethyl)-N-methyl-4,4'-bipyridin-2-amine;
(140) (E)-6-(2-((4,5-dimethylthiophen-2-yl)methylene)hydrazinyl)-N-(2-methoxyethyl)-N-methyl-4,4'-bipyridin-2-amine;
(141) (E)-4-(2-(6-(2-(3-methylbenzylidene)hydrazinyl)-2-(pyridin-4-yl)pyrimidin-4-yloxy)ethyl)morpholine;
(142) (E)-4-(methoxymethyl)-6-(2-(3-methylbenzylidene)hydrazinyl)-2-(pyridin-4-yl)pyrimidine;
(143) (E)-4-(2-(3-methylbenzylidene)hydrazinyl)-6-(pyridin-3-yl)-1,3,5-triazin-2-amine;
(144) 1-(4-(methylthio)-6-(pyridin-4-yl)-1,3,5-triazin-2-yl)-3-m-tolylurea;
(145) 1-(4-(methylthio)-6-(pyridin-3-yl)-1,3,5-triazin-2-yl)-3-m-tolylurea;
(146) N-(2,3-dimethyl-1H-indol-5-yl)-2,4'-bipyridine-6-carboxamide;
(147) N-(2,3-dimethyl-1H-indol-5-yl)-2-(dimethylamino)-6-(2-morpholino ethylamino) pyrimidine-4-carboxamide; and
(148) N-(2,3-dimethyl-1H-indol-5-yl)-6-(2-morpholinoethylamino)-2-(thiazolidin-3-yl)pyrimidine-4-carboxamide;
or pharmaceutically acceptable salts thereof.

15. A pharmaceutical composition, comprising a pharmaceutically acceptable carrier and a compound of claim 1.

\* \* \* \* \*